(12) United States Patent
Kim et al.

(10) Patent No.: US 10,266,862 B2
(45) Date of Patent: Apr. 23, 2019

(54) METHOD FOR PREPARING PSICOSE

(71) Applicant: INDUSTRY-ACADEMIC COOPERATION FOUNDATION GYEONGSANG NATIONAL UNIVERSITY, Gyeongsangnam-do (KR)

(72) Inventors: Seon-Won Kim, Gyeongsangnam-do (KR); Min-Jin Choi, Gyeongsangnam-do (KR); Seong-Hee Jeong, Gyeongsangnam-do (KR); Dae-Yun Lee, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 25 days.

(21) Appl. No.: 15/524,362

(22) PCT Filed: Nov. 6, 2015

(86) PCT No.: PCT/KR2015/011954
§ 371 (c)(1),
(2) Date: May 4, 2017

(87) PCT Pub. No.: WO2016/072800
PCT Pub. Date: May 12, 2016

(65) Prior Publication Data
US 2018/0273994 A1 Sep. 27, 2018

(30) Foreign Application Priority Data

Nov. 6, 2014 (KR) .................. 10-2014-0153949
Nov. 6, 2015 (KR) .................. 10-2015-0156115

(51) Int. Cl.
*C12P 19/02* (2006.01)
*C13K 13/00* (2006.01)
*C12P 7/18* (2006.01)
*B01D 15/08* (2006.01)

(52) U.S. Cl.
CPC .............. *C12P 19/02* (2013.01); *C12P 7/18* (2013.01); *C12Y 101/01255* (2013.01); *C13K 13/007* (2013.01); *B01D 15/08* (2013.01)

(58) Field of Classification Search
CPC .. C12P 19/02; C12P 19/24; C12P 7/18; C12N 9/90; C12Y 501/03; C12Y 101/01255; Y02P 20/582; C13K 13/007; B01D 15/08
See application file for complete search history.

(56) References Cited

U.S. PATENT DOCUMENTS

| | | | | |
|---|---|---|---|---|
| 8,735,106 B2* | 5/2014 | Hong | ...................... | C12N 9/90 |
| | | | | 435/105 |
| 9,506,087 B2* | 11/2016 | Vroom | ...................... | C12P 7/10 |
| 2005/0239180 A1 | 10/2005 | Sahm et al. | | |

FOREIGN PATENT DOCUMENTS

| | | |
|---|---|---|
| EP | 0302970 A1 | 2/1989 |
| KR | 10-2006-0125971 A | 12/2006 |
| KR | 10-0832339 B1 | 5/2008 |
| KR | 10-2011-0035805 A | 4/2011 |
| KR | 10-2011-0041910 A | 4/2011 |
| KR | 10-2011-0108185 A | 10/2011 |
| KR | 10-1106253 B1 | 1/2012 |
| KR | 10-1203856 B1 | 11/2012 |
| KR | 10-2013-0029754 A | 3/2013 |
| KR | 10-2014-0140215 A | 12/2014 |
| WO | WO 2014-168302 A1 | 10/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Granstom et al., Izumoring: A novel complete strategy for bioproduction of rare sugars. J. Biosci. Bioeng., 2004, vol. 97(2): 89-94. (Year: 2004).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Sheelendra Mangal Bhatt et al., "Challenges in Enzymatic Route of Mannitol Production", ISRN Biotechnology, vol. 2013, pp. 1-13, (2013).
Notice of Allowance dated Jun. 27, 2017 from Korean Patent Office in a counterpart Korean Patent Application No. 10-2015-0156115.
International Search Report for PCT/KR2015/011954, dated May 4, 2017.
Choi, Jin-Geun et al., Improvement in the Thermostability of D-Psicose 3-Epimerase from Agrobacterium tumefaciens by Random and Site-directed Mutagenesis, Applied and Environmental Microbiology, vol. 77, No. 20, pp. 7316-7320, Oct. 2011.

(Continued)

*Primary Examiner* — Ganapathirama Raghu
(74) *Attorney, Agent, or Firm* — The PL Law Group, PLLC

(57) ABSTRACT

A method for obtaining psicose from a mixture of fructose and psicose includes adding a mannitol dehydrogenase to a mixture of fructose and psicose to convert fructose into mannitol, and separating the mannitol from the psicose. Accordingly, the psicose can be more easily isolated from the mannitol with high efficiency by using the method.

17 Claims, 14 Drawing Sheets
Specification includes a Sequence Listing.

(56) References Cited

OTHER PUBLICATIONS

Office action dated Dec. 12, 2016 from Korean Intellectual Property Office in a counterpart Korean Patent Application No. 10-2015-0156115.
Badal C. Saha & F. Michael Racine, Biotechnological production of mannitol and its applications, Applied Microbiology and Biotechnology., vol. 89, p. 879-891, Nov. 2010.

* cited by examiner

FIG. 7

```
                    1                                              50
AtDPE     (1)   ---MKHGIYYSYWEHEWSAKFGPYIEKVAKLGFDIIEVAAHHINEY---SDA
AcDPE     (1)   MKNKFGVDSFIWTESFSKKDLWIIPKAKELGFEVIDFAISNPFTFP------
CbDPE     (1)   ---MKYGIYFAYWTKEWFADYKKYMDKVSALGFDVLEISCAALRDVYTTKE
ChDPE     (1)   ---MKHGIYYAYWEQEWAADYKRYVEKVAKLGFDILEIGAGPLPEY--AEQ
Consensus (1)       MKHGIYYAYWT EWSAKYKKYIEKVAKLGFDIIEIAAA L EY   SD
                   51                                             100
AtDPE     (47)  ELATIRKSAKDNGIILTAGIGPSKTKNLSSEDAAVRAAGKAFFERTLSNV
AcDPE     (47)  -VEKVKAELERVGIDCVCTTTLTPETNPISPDAEIRAAGVKAMKKCVDIC
CbDPE     (49)  QLIELREYAKEKGLVLTAGYGPTKAENLCSEDPEAVRRAMTFFKDLLPEL
ChDPE     (47)  DVKELYKCAQDNGITLTAGYGPTFNHNIGSSDAGVREEALEWYKRLFEVL
Consensus (51)  DL ELKK AKDNGIILTAGYGPTK  NL SEDAEVRAAAL FFKRLLDIL
                  101                                            150
AtDPE     (97)  AKLDIHTIGGALHSYWPIDYSQPVDKAGDYARGVEGINGIADFANDL-GI
AcDPE     (96)  NELGAPILGGVNYAGWGYLTKK-PRTEEEWNWGVECMREVAEYAEQTGDV
CbDPE     (99)  QLMDIHILGGGLYSWPVDFTINNDKQGDPARAVRNLRELSKTAEEC-DV
ChDPE     (97)  AELDIHLIGGALYSYWPVDFAN-ADKTEDWKSVEGMQRLAPAAAKY-DI
Consensus (101) AELDIHI IGGALYSYWPVDFSN  DK  GDWA GVEGMRELADFA  DI
                  151                                            200
AtDPE     (146) NLCIEVLNRFENHVLNTAAEGVAPVKDVGKNNVKVMLDTFHMNIEEDSFG
AcDPE     (145) TICVECVNPFETHPLNIAEDAVAFCKDVGTGNVKVHLDCFHMIREEKSFA
CbDPE     (148) VLGMEVLNRYEGYILNTCEEAIDFVDEIGSSHVKIMLDTFHMNIEETNMA
ChDPE     (145) NLGMEVLNRFESHILNTAEEGVKFVEEVGMDNVKVMLDTFHMNIEEQSIG
Consensus (151) NLGMEVLNRFESHILNTAEEAVAFVKDVGS NVKVMLDTFHMNIEE SFA
                  201                  S213C                     250
AtDPE     (196) DAIRTAG-PLLGHFHTGESNRRVPGKGRMPWHEIGLALRDINYTGAVIME
AcDPE     (195) GAVKTCGKEYLGYIHVNENDRGIPGTGLVPFKEFFNALVEIGYDGPLVIE
CbDPE     (198) DAIREAG-DRLGHLHLGSQNRLVPGKGSLPWAEIGQALRDINYQGAAVME
ChDPE     (195) GAIREAG-KLLGHFHTGFCNRMVPGKGRIPWREIGDALRDIGYDGTAVME
Consensus (201) GAIRTAG DLLGHFHTGENNRLVPGKGRIPWKEIGNALRDINYDGAAVME
                  251                          296
AtDPE     (245) PFVKTGGTIGSDIKVWRDLSGGADIAKMDEDARNALAPSRFVLGG-- (SEQ ID NO: 3)
AcDPE     (245) SFDPSFEELSGNCAIWRKLADTGEELAIEGLKNLKAIAAEI------ (SEQ ID NO: 4)
CbDPE     (247) PFVMQGGTIGSEIKVWRDMVPDLSEEALDRDAKGALEFCRHVFGI-  (SEQ ID NO: 9)
ChDPE     (244) PFVRMGGQVGADIKVWRDISPGADEAQLDDDARRALEFQRYMLEWK (SEQ ID NO: 10)
Consensus (251) PFVKSGGTIGSDIKVWRDLS GADEAALDDDAR ALEFARHVLG   (SEQ ID NO: 53)
```

SEQUENCE LISTING

```
<160> NUMBER OF SEQ ID NOS: 53

<210> SEQ ID NO 1
<211> LENGTH: 870
<212> TYPE: DNA
<213> ORGANISM: Agrobacterium tumefaciens

<400> SEQUENCE: 1
atgaaacacg gcatctatta ttcttactgg gaacatgagt ggagcgccaa gttcggtccc        60
tatatcgaga aggtcgccaa gctcggtttc gacatcatcg aagtcgccgc ccaccatatc       120
aacgaataca gcgacgccga actcgcgacc atcaggaaga gcgcgaagga taacggcatc       180
atcctcaccg ccggcatcgg tccgtcgaaa accaagaacc tgtcgtcgga agatgctgcg       240
gtgcgtgcgg ccggcaaggc gttctttgaa agaacccttt cgaacgtcgc caagctcgat       300
atccacacca tcggcggcgc attgcattcc tattggccaa tcgattattc gcagcccgtc       360
gacaaggcag gcgattatgc gcgcggcgtc gagggtatca acggcattgc cgatttcgcc       420
```

```
aatgatctcg gcatcaacct gtgcatcgaa gtcctcaacc gctttgaaaa ccacgtcctc    480
aacacggcgg cggaaggcgt cgcttttgtg aaggatgtcg gcaagaacaa tgtgaaagtc    540
atgctggata ccttccacat gaacatcgag gaagacagtt tcggtgacgc catccgcacg    600
gccggcccgc ttctggggca cttccatacc ggtgaaagca atcgccgcgt accgggcaag    660
ggcagaatgc cgtggcacga aatcggcctt gcgctgcgtg atatcaacta caccggcgcg    720
gtaatcatgg agcctttcgt caagacaggc ggcaccatcg gctcggatat caaggtgtgg    780
cgcgacctga gcggtggcgc cgacatcgcg aaaatggatg aagatgcccg caatgcgctg    840
gcattctccc gcttcgttct tggtggctaa                                    870

<210> SEQ ID NO 2
<211> LENGTH: 858
<212> TYPE: DNA
<213> ORGANISM: Anaerostipes caccae

<400> SEQUENCE: 2
atgaaaaata aattcggagt tgacagtttt atttggactg aatcctttc taaaaaagat     60 ttatggatca tccccaaggc aaaagaactg ggatttgaag tcatcgactt tgcgatctcc    120
aacccattca cattccctgt agagaaagtg aaggcagagc tagagagagt gggaatcgac    180
tgtgtctgca ctaccacgct gacacctgaa accaatccga tttctccgga tgccgagatc    240
cgtgcggcag gcgtaaaagc catgaaaaaa tgtgtggata tctgcaacga actgggtgca    300
ccgatcttag gcggtgtaaa ttatgcaggc tggggatatc tgacgaagaa gccaaggacc    360
gaggaagagt ggaactgggg cgtagagtgc atgagggaag ttgccgagta cgcaaagcaa    420
accggagatg ttaccatctg tgtggaatgt gtcaacagat ttgaaaccca cttcttaaac    480
attgcggaag atgcagtggc cttctgtaag gatgttggaa caggaaatgt caaggttcat    540
ctcgactgct tccatatgat cagagaagaa aagagctttg caggggcagt aaagacctgc    600
ggcaaagaat atctcggata cattcatgtc aatgaaaacg acagaggtat tcctggaaca    660
gggcttgtac cgtttaaaga attttttcaat gcattagtag gatcgggta tgacggacct    720 ttggtgatcg aatcttttga tccgagcttt gaagaactgt ccggcaactg tgcgatctgg    780
agaaaacttg ccgatactgg agaagaactt gcgattgaag ggctgaaaaa tctgaaagcc    840
atcgctgctg agatataa                                                 858

<210> SEQ ID NO 3
<211> LENGTH: 289
<212> TYPE: PRT
<213> ORGANISM: Agrobacterium tumefaciens

<400> SEQUENCE: 3

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
```

```
            85                  90                  95
Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 4
<211> LENGTH: 285
<212> TYPE: PRT
<213> ORGANISM: Anaerostipes caccae

<400> SEQUENCE: 4

Met Lys Asn Lys Phe Gly Val Asp Ser Phe Ile Trp Thr Glu Ser Phe
1               5                   10                  15

Ser Lys Lys Asp Leu Trp Ile Ile Pro Lys Ala Lys Glu Leu Gly Phe
            20                  25                  30

Glu Val Ile Asp Phe Ala Ile Ser Asn Pro Phe Thr Phe Pro Val Glu
        35                  40                  45

Lys Val Lys Ala Glu Leu Glu Arg Val Gly Ile Asp Cys Val Cys Thr
    50                  55                  60

Thr Thr Leu Thr Pro Glu Thr Asn Pro Ile Ser Pro Asp Ala Glu Ile
65                  70                  75                  80

Arg Ala Ala Gly Val Lys Ala Met Lys Lys Cys Val Asp Ile Cys Asn
                85                  90                  95

Glu Leu Gly Ala Pro Ile Leu Gly Gly Val Asn Tyr Ala Gly Trp Gly
            100                 105                 110

Tyr Leu Thr Lys Lys Pro Arg Thr Glu Glu Glu Trp Asn Trp Gly Val
        115                 120                 125

Glu Cys Met Arg Glu Val Ala Glu Tyr Ala Lys Gln Thr Gly Asp Val
    130                 135                 140

Thr Ile Cys Val Glu Cys Val Asn Arg Phe Glu Thr His Phe Leu Asn
145                 150                 155                 160

Ile Ala Glu Asp Ala Val Ala Phe Cys Lys Asp Val Gly Thr Gly Asn
```

```
                165                 170                 175
Val Lys Val His Leu Asp Cys Phe His Met Ile Arg Glu Glu Lys Ser
            180                 185                 190

Phe Ala Gly Ala Val Lys Thr Cys Gly Lys Glu Tyr Leu Gly Tyr Ile
            195                 200                 205

His Val Asn Glu Asn Asp Arg Gly Ile Pro Gly Thr Gly Leu Val Pro
            210                 215                 220

Phe Lys Glu Phe Phe Asn Ala Leu Val Glu Ile Gly Tyr Asp Gly Pro
225                 230                 235                 240

Leu Val Ile Glu Ser Phe Asp Pro Ser Phe Glu Glu Leu Ser Gly Asn
            245                 250                 255

Cys Ala Ile Trp Arg Lys Leu Ala Asp Thr Gly Glu Glu Leu Ala Ile
            260                 265                 270

Glu Gly Leu Lys Asn Leu Lys Ala Ile Ala Ala Glu Ile
            275                 280                 285

<210> SEQ ID NO 5
<211> LENGTH: 289
<212> TYPE: PRT
<213> ORGANISM: Agrobacterium tumefaciens

<400> SEQUENCE: 5

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Leu Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255
```

-continued

```
Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly
```

<210> SEQ ID NO 6
<211> LENGTH: 269
<212> TYPE: PRT
<213> ORGANISM: Unknown
<220> FEATURE:
<223> OTHER INFORMATION: psicose 3-epimerase

<400> SEQUENCE: 6

```
Met Lys His Gly Ile Tyr Tyr Ala Tyr Trp Thr Glu Trp Ser Ala Lys
1               5                   10                  15

Tyr Lys Lys Tyr Ile Glu Lys Val Ala Lys Leu Gly Phe Asp Ile Ile
            20                  25                  30

Glu Ile Ala Ala Ala Leu Glu Tyr Ser Asp Asp Leu Glu Leu Lys Lys
        35                  40                  45

Ala Lys Asp Asn Gly Ile Ile Leu Thr Ala Gly Tyr Gly Pro Thr Lys
    50                  55                  60

Asn Leu Ser Glu Asp Ala Glu Val Arg Ala Ala Ala Leu Phe Phe Lys
65                  70                  75                  80

Arg Leu Leu Asp Ile Leu Ala Glu Leu Asp Ile His Ile Ile Gly Gly
                85                  90                  95

Ala Leu Tyr Ser Tyr Trp Pro Val Asp Phe Ser Asn Asp Lys Gly Asp
            100                 105                 110

Trp Ala Trp Gly Val Glu Gly Met Arg Glu Leu Ala Asp Phe Ala Asp
        115                 120                 125

Asp Ile Asn Leu Gly Met Glu Val Leu Asn Arg Phe Glu Ser His Ile
    130                 135                 140

Leu Asn Thr Ala Glu Glu Ala Val Ala Phe Val Lys Asp Val Gly Ser
145                 150                 155                 160

Asn Val Lys Val Met Leu Asp Thr Phe His Met Asn Ile Glu Glu Ser
                165                 170                 175

Phe Ala Gly Ala Ile Arg Thr Ala Gly Asp Leu Leu Gly His Phe His
            180                 185                 190

Thr Gly Glu Asn Asn Arg Leu Val Pro Gly Lys Gly Arg Ile Pro Trp
        195                 200                 205

Lys Glu Ile Gly Asn Ala Leu Arg Asp Ile Asn Tyr Asp Gly Ala Ala
    210                 215                 220

Val Met Glu Pro Phe Val Lys Ser Gly Gly Thr Ile Gly Ser Asp Ile
225                 230                 235                 240

Lys Val Trp Arg Asp Leu Ser Gly Ala Asp Glu Ala Ala Leu Asp Asp
                245                 250                 255

Asp Ala Arg Ala Leu Glu Phe Ala Arg His Val Leu Gly
            260                 265
```

<210> SEQ ID NO 7
<211> LENGTH: 876
<212> TYPE: DNA
<213> ORGANISM: Clostridium bolteae

<400> SEQUENCE: 7

```
atgaaatatg gtatttattt tgcttattgg acgaaggaat ggtttgctga ttataagaag     60
```

```
tatatggata aggtgtctgc tttggggttt gatgtcctgg aaatttcctg tgcagccctc    120
agagatgtat acacaaccaa ggaacagctg attgagctac gtaatacgc caaagaaaaa     180 gggcttgttc taacagctgg ttatggacct actaaagcag aaaatctgtg ttcagaagac    240
ccggaggcag tgagacgggc catgacattc ttcaaggacc tgcttccaaa gctgcagtta    300
atggatatcc atatcctggg agggggatta tattcctact ggcccgtgga ttttaccatt    360
aataatgaca agcagggaga ccgggccagg gctgtcagga atctgaggga attgtccaaa    420
acagcggagg aatgtgacgt ggtgcttgga atggaggtac tgaaccgcta tgagggtat     480 attcttaata cctgtgaaga ggcaattgat tttgtcgatg agattggaag cagccatgta    540
aaaatcatgc tggatacttt ccatatgaat attgaagaga caaatatggc tgatgcaatc    600
cgcaaggcgg gagacaggct gggacatctc catctgggag aacagaaccg cctggtgccg    660
ggaaaaggca gcctgccatg ggctgagata gggcaggcgc tccgtgatat taactatcag    720
ggagccgctg tcatggaacc ttttgtcatg cagggaggga ccatcggttc tgagataaag    780
gtatggagag acatggtgcc ggatcttct gaggaagcac tggacaggga tgcaaagggt    840
gcgctggaat tctgcaggca tgtgtttggt atctaa                               876

<210> SEQ ID NO 8
<211> LENGTH: 870
<212> TYPE: DNA
<213> ORGANISM: Clostridium hylemonae

<400> SEQUENCE: 8
atgaaacatg gtatctatta tgcatactgg gaacaagaat gggcggccga ctacaagcgc     60
tatgttgaaa aggtggcaaa gcttgggttt gacattctgg atcggcgc tgggccgctg     120 ccggaatacg cagagcagga tgtgaaggaa ctgaagaaat gtgcgcagga caatgggatc    180
acgctgacgg ccggatatgg tccgacgttc aaccacaata tcggttcttc agacgccggg    240
gtaagggaag aggcgctgga atggtataag aggttatttg aagtgctggc agagcttgat    300
atccacctga tcggaggggc gctctattct tactggcctg tcgattttgc aaacgccgat    360
aaaacggaag actggaagtg gagtgtagag ggcatgcaga ggctggcgcc ggccgcggcc    420
aaatatgaca tcaacctggg catggaagtt ctgaaccggt ttgagagcca tatcctgaat    480
acagccgagg aaggtgtgaa gtttgtagag gaagtcggca tggacaacgt aaaggtcatg    540
ctggatacat tccatatgaa tatagaagag caaagcatag gcggcgcgat ccgccgggca    600
ggaaaactgc tcgggcattt ccacaccgga gaatgcaacc gcatggtgcc gggaagggga    660
cgtattccat ggcgtgagat aggggatgct ctccgtgata tcggatatga cggaactgct    720
gtaatggagc cgttcgttcg catgggagga caggtcggcg ctgatatcaa ggtgtgggaga    780 gacataagcc gtgagcaga cgaggcacag cttgacgatg acgcgcgccg tgcgctggag    840
ttccagagat atatgctgga gtggaagtaa                                      870

<210> SEQ ID NO 9
<211> LENGTH: 291
<212> TYPE: PRT
<213> ORGANISM: Clostridium bolteae

<400> SEQUENCE: 9

Met Lys Tyr Gly Ile Tyr Phe Ala Tyr Trp Thr Lys Glu Trp Phe Ala
1               5                   10                  15

Asp Tyr Lys Lys Tyr Met Asp Lys Val Ser Ala Leu Gly Phe Asp Val
            20                  25                  30
```

```
Leu Glu Ile Ser Cys Ala Ala Leu Arg Asp Val Tyr Thr Thr Lys Glu
            35                  40                  45

Gln Leu Ile Glu Leu Arg Glu Tyr Ala Lys Glu Lys Gly Leu Val Leu
 50                  55                  60

Thr Ala Gly Tyr Gly Pro Thr Lys Ala Glu Asn Leu Cys Ser Glu Asp
 65                  70                  75                  80

Pro Glu Ala Val Arg Arg Ala Met Thr Phe Phe Lys Asp Leu Leu Pro
                 85                  90                  95

Lys Leu Gln Leu Met Asp Ile His Ile Leu Gly Gly Leu Tyr Ser
            100                 105                 110

Tyr Trp Pro Val Asp Phe Thr Ile Asn Asn Asp Lys Gln Gly Asp Arg
            115                 120                 125

Ala Arg Ala Val Arg Asn Leu Arg Glu Leu Ser Lys Thr Ala Glu Glu
            130                 135                 140

Cys Asp Val Val Leu Gly Met Glu Val Leu Asn Arg Tyr Glu Gly Tyr
145                 150                 155                 160

Ile Leu Asn Thr Cys Glu Ala Ile Asp Phe Val Asp Glu Ile Gly
                165                 170                 175

Ser Ser His Val Lys Ile Met Leu Asp Thr Phe His Met Asn Ile Glu
            180                 185                 190

Glu Thr Asn Met Ala Asp Ala Ile Arg Lys Ala Gly Asp Arg Leu Gly
            195                 200                 205

His Leu His Leu Gly Glu Gln Asn Arg Leu Val Pro Gly Lys Gly Ser
210                 215                 220

Leu Pro Trp Ala Glu Ile Gly Gln Ala Leu Arg Asp Ile Asn Tyr Gln
225                 230                 235                 240

Gly Ala Ala Val Met Glu Pro Phe Val Met Gln Gly Gly Thr Ile Gly
                245                 250                 255

Ser Glu Ile Lys Val Trp Arg Asp Met Val Pro Asp Leu Ser Glu Glu
            260                 265                 270

Ala Leu Asp Arg Asp Ala Lys Gly Ala Leu Glu Phe Cys Arg His Val
            275                 280                 285

Phe Gly Ile
    290

<210> SEQ ID NO 10
<211> LENGTH: 289
<212> TYPE: PRT
<213> ORGANISM: Clostridium hylemonae

<400> SEQUENCE: 10

Met Lys His Gly Ile Tyr Tyr Ala Tyr Trp Glu Gln Glu Trp Ala Ala
1               5                   10                  15

Asp Tyr Lys Arg Tyr Val Glu Lys Val Ala Lys Leu Gly Phe Asp Ile
            20                  25                  30

Leu Glu Ile Gly Ala Gly Pro Leu Pro Glu Tyr Ala Glu Gln Asp Val
            35                  40                  45

Lys Glu Leu Lys Lys Cys Ala Gln Asp Asn Gly Ile Thr Leu Thr Ala
 50                  55                  60

Gly Tyr Gly Pro Thr Phe Asn His Asn Ile Gly Ser Ser Asp Ala Gly
 65                  70                  75                  80

Val Arg Glu Glu Ala Leu Glu Trp Tyr Lys Arg Leu Phe Glu Val Leu
                 85                  90                  95

Ala Glu Leu Asp Ile His Leu Ile Gly Gly Ala Leu Tyr Ser Tyr Trp
```

|  | 100 |  |  |  | 105 |  |  |  | 110 |  |  |  |
|---|---|---|---|---|---|---|---|---|---|---|---|---|

Pro Val Asp Phe Ala Asn Ala Asp Lys Thr Glu Asp Trp Lys Trp Ser
    115                      120                      125

Val Glu Gly Met Gln Arg Leu Ala Pro Ala Ala Ala Lys Tyr Asp Ile
 130                         135                      140

Asn Leu Gly Met Glu Val Leu Asn Arg Phe Glu Ser His Ile Leu Asn
145                      150                      155                      160

Thr Ala Glu Glu Gly Val Lys Phe Val Glu Glu Val Gly Met Asp Asn
            165                      170                      175

Val Lys Val Met Leu Asp Thr Phe His Met Asn Ile Glu Glu Gln Ser
         180                       185                      190

Ile Gly Gly Ala Ile Arg Arg Ala Gly Lys Leu Leu Gly His Phe His
               195                      200                      205

Thr Gly Glu Cys Asn Arg Met Val Pro Gly Lys Gly Arg Ile Pro Trp
 210                         215                      220

Arg Glu Ile Gly Asp Ala Leu Arg Asp Ile Gly Tyr Asp Gly Thr Ala
225                    230                      235                      240

Val Met Glu Pro Phe Val Arg Met Gly Gly Gln Val Gly Ala Asp Ile
             245                      250                      255

Lys Val Trp Arg Asp Ile Ser Arg Gly Ala Asp Glu Ala Gln Leu Asp
         260                       265                      270

Asp Asp Ala Arg Arg Ala Leu Glu Phe Gln Arg Tyr Met Leu Glu Trp
               275                      280                      285

Lys

<210> SEQ ID NO 11
<211> LENGTH: 963
<212> TYPE: DNA
<213> ORGANISM: Escherichia coli

<400> SEQUENCE: 11

| atgattaaga | aaatcggtgt | gttgacaagc | ggcggtgatg | cgccaggcat | gaacgccgca | 60 |
| attcgcgggg | ttgttcgttc | tgcgctgaca | gaaggtctgg | aagtaatggg | tatttatgac | 120 |
| ggctatctgg | gtctgtatga | agaccgtatg | gtacagctag | accgttacag | cgtgtctgac | 180 |
| atgatcaacc | gtggcggtac | gttcctcggt | tctgcgcgtt | tcccggaatt | ccgcgacgag | 240 |
| aacatccgcg | ccgtggctat | cgaaaacctg | aaaaaacgtg | gtatcgacgc | gctggtggtt | 300 |
| atcggcggtg | acggttccta | catgggtgca | atgcgtctga | ccgaaatggg | cttcccgtgc | 360 |
| atcggtctgc | cgggcactat | cgacaacgac | atcaaaggca | ctgactacac | tatcggtttc | 420 |
| ttcactgcgc | tgagcaccgt | tgtagaagcg | atcgaccgtc | tgcgtgacac | ctcttcttct | 480 |
| caccagcgta | tttccgtggt | ggaagtgatg | ggccgttatt | gtggagatct | gacgttggct | 540 |
| gcggccattg | ccggtggctg | tgaattcgtt | gtggttccgg | aagttgaatt | cagccgtgaa | 600 |
| gacctggtaa | acgaaatcaa | agcgggtatc | gcgaaaggta | aaaaacacgc | gatcgtggcg | 660 |
| attaccgaac | atatgtgtga | tgttgacgaa | ctggcgcatt | tcatcgagaa | agaaaccggt | 720 |
| cgtgaaaccc | gcgcaactgt | gctgggccac | atccagcgcg | gtggttctcc | ggtgccttac | 780 |
| gaccgtattc | tggcttcccg | tatgggcgct | tacgctatcg | atctgctgct | ggcaggttac | 840 |
| ggcggtcgtt | gtgtaggtat | ccagaacgaa | cagctggttc | accacgacat | catcgacgct | 900 |
| atcgaaaaca | tgaagcgtcc | gttcaaaggt | gactggctgg | actgcgcgaa | aaactgtat | 960 |
| taa | | | | | | 963 |

<210> SEQ ID NO 12
<211> LENGTH: 320
<212> TYPE: PRT
<213> ORGANISM: Escherichia coli

<400> SEQUENCE: 12

```
Met Ile Lys Lys Ile Gly Val Leu Thr Ser Gly Gly Asp Ala Pro Gly
1               5                   10                  15

Met Asn Ala Ala Ile Arg Gly Val Val Arg Ser Ala Leu Thr Glu Gly
            20                  25                  30

Leu Glu Val Met Gly Ile Tyr Asp Gly Tyr Leu Gly Leu Tyr Glu Asp
        35                  40                  45

Arg Met Val Gln Leu Asp Arg Tyr Ser Val Ser Asp Met Ile Asn Arg
    50                  55                  60

Gly Gly Thr Phe Leu Gly Ser Ala Arg Phe Pro Glu Phe Arg Asp Glu
65                  70                  75                  80

Asn Ile Arg Ala Val Ala Ile Glu Asn Leu Lys Lys Arg Gly Ile Asp
                85                  90                  95

Ala Leu Val Val Ile Gly Gly Asp Gly Ser Tyr Met Gly Ala Met Arg
            100                 105                 110

Leu Thr Glu Met Gly Phe Pro Cys Ile Gly Leu Pro Gly Thr Ile Asp
        115                 120                 125

Asn Asp Ile Lys Gly Thr Asp Tyr Thr Ile Gly Phe Phe Thr Ala Leu
    130                 135                 140

Ser Thr Val Val Glu Ala Ile Asp Arg Leu Arg Asp Thr Ser Ser Ser
145                 150                 155                 160

His Gln Arg Ile Ser Val Val Glu Val Met Gly Arg Tyr Cys Gly Asp
                165                 170                 175

Leu Thr Leu Ala Ala Ala Ile Ala Gly Gly Cys Glu Phe Val Val Val
            180                 185                 190

Pro Glu Val Glu Phe Ser Arg Glu Asp Leu Val Asn Glu Ile Lys Ala
        195                 200                 205

Gly Ile Ala Lys Gly Lys Lys His Ala Ile Val Ala Ile Thr Glu His
    210                 215                 220

Met Cys Asp Val Asp Glu Leu Ala His Phe Ile Glu Lys Glu Thr Gly
225                 230                 235                 240

Arg Glu Thr Arg Ala Thr Val Leu Gly His Ile Gln Arg Gly Gly Ser
                245                 250                 255

Pro Val Pro Tyr Asp Arg Ile Leu Ala Ser Arg Met Gly Ala Tyr Ala
            260                 265                 270

Ile Asp Leu Leu Leu Ala Gly Tyr Gly Gly Arg Cys Val Gly Ile Gln
        275                 280                 285

Asn Glu Gln Leu Val His His Asp Ile Ile Asp Ala Ile Glu Asn Met
    290                 295                 300

Lys Arg Pro Phe Lys Gly Asp Trp Leu Asp Cys Ala Lys Lys Leu Tyr
305                 310                 315                 320
```

<210> SEQ ID NO 13
<211> LENGTH: 450
<212> TYPE: DNA
<213> ORGANISM: Escherichia coli

<400> SEQUENCE: 13

```
atgaaaaaga ttgcatttgg ctgtgatcat gtcggtttca ttttaaaaca tgaaatagtg    60
gcacatttag ttgagcgtgg cgttgaagtg attgataaag gaacctggtc gtcagagcgt   120
```

| | |
|---|---|
| actgattatc cacattacgc cagtcaagtc gcactggctg ttgctggcgg agaggttgat | 180 |
| ggcgggattt tgatttgtgg tactggcgtc ggtatttcga tagcggcgaa caagtttgcc | 240 |
| ggaattcgcg cggtcgtctg tagcgaacct tattccgcgc aactttcgcg gcagcataac | 300 |
| gacaccaacg tgctggcttt tggttcacga gtggttggcc tcgaactggc aaaaatgatt | 360 |
| gtggatgcgt ggctgggcgc acagtacgaa ggcggtcgtc atcaacaacg cgtggaggcg | 420 |
| attacggcaa tagagcagcg gagaaattga | 450 |

<210> SEQ ID NO 14
<211> LENGTH: 891
<212> TYPE: DNA
<213> ORGANISM: Escherichia coli

<400> SEQUENCE: 14

| | |
|---|---|
| atgagccagt cagagtttga ttcagcgctt ccgaacggta tagggttagc gccttacctg | 60 |
| cgaatgaagc aggaaggaat gacagaaaat gaaagccgca tcgtggagtg gttactcaaa | 120 |
| cccggtaacc tgagttgtgc acccgcaatt aaagatgtcg cagaagctct ggcggtatct | 180 |
| gaagcgatga tagttaaggt atcaaagctg ctggggttta gcggctttcg taacttacgc | 240 |
| agtgcgctgg aagattattt ttctcagtca gaacaggtat tgccttccga gttggctttt | 300 |
| gatgaagcgc gcaggatgt ggtgaataag gtatttaaca tcactttacg caccattatg | 360 |
| gaaggtcagt cgatcgtcaa cgttgatgag atccaccgtg ccgcccgctt tttctatcag | 420 |
| gccagacagc gggatttgta cggtgccgga ggatcaaatg ctatctgtgc tgatgtacag | 480 |
| cacaagttct tgcgcattgg cgtacgctgt caggcctatc ctgatgctca catcatgatg | 540 |
| atgtccgctt cgttgttaca ggaaggagat gttgtgctgg tagtgaccca ttccgggcga | 600 |
| accagtgatg taaaagcggc cgtagaactg gcaaaaaaga cggggcaaa gattatttgt | 660 |
| ataacccata gctaccattc accgatagcg aaactggccg attatattat ttgctcacca | 720 |
| gccccggaaa cgccgttatt aggtcgtaat gcctcggcaa gaatattaca actaactttg | 780 |
| ctggacgctt tttttgtctc tgtcgcccag ctcaacattg aacaagctaa tattaatatg | 840 |
| caaaaaaccg gcgcaattgt tgatttcttc tcaccaggcg cgctgaaata a | 891 |

<210> SEQ ID NO 15
<211> LENGTH: 936
<212> TYPE: DNA
<213> ORGANISM: Escherichia coli

<400> SEQUENCE: 15

| | |
|---|---|
| atgaataaat atctgaaata tttcagcggc acactcgtgg gcttaatgtt gtcaaccagc | 60 |
| gcttttgctg ccgccgaata tgctgtcgta ttgaaaaccc tctccaaccc attttgggta | 120 |
| gatatgaaaa aaggcattga agatgaagca aaaacactgg gcgtcagcgt tgatattttt | 180 |
| gcctctcctt cagaaggcga ttttcaatct caattgcagt tatttgaaga tctcagtaat | 240 |
| aaaaattaca aggtatcgc cttcgctcca ttatcctcag tgaatctggt catgcctgtc | 300 |
| gcccgcgcat ggaaaaaagg catttatctg gttaatctcg atgaaaaaat cgacatggat | 360 |
| aatctgaaaa aagctggcgg caatgtgaa gcttttgtca ccaccgataa cgttgctgtc | 420 |
| ggggcgaaag gcgcgtcgtt cattattgac aaattgggcg ctgaaggtgg tgaagtcgca | 480 |
| atcattgagg gtaaagccgg taacgcctcc ggtgaagcgc gtcgtaatgg tgccaccgaa | 540 |
| gccttcaaaa aagcaagcca gatcaagctt gtcgccagcc agcctgccga ctgggaccgc | 600 |

```
attaaagcac tggatgtcgc cactaacgtg ttgcaacgta atccgaatat taaagcgatc    660
tattgcgcga atgacacgat ggcaatgggt gttgctcagg cagtcgcaaa cgccggaaaa    720
acgggaaaag tgctggtcgt cggtacagat ggcattccgg aagcccgcaa aatggtggaa    780
gccggacaaa tgaccgcgac ggttgcccag aacccggcgg atatcggcgc aacgggtctg    840
aagctgatgg ttgacgctga gaaatccggc aaggttatcc cgctggataa agcaccggaa    900
tttaaactgg tcgattcaat cctggtcact caataa                              936
```

<210> SEQ ID NO 16
<211> LENGTH: 1533
<212> TYPE: DNA
<213> ORGANISM: Escherichia coli

<400> SEQUENCE: 16

```
atggccacgc catatatatc gatggcgggg atcggcaagt cctttggtcc ggttcacgca     60
ttaaagtcgg ttaatttaac ggtttatcct ggtgaaatac atgcattact aggagaaaat    120
ggcgcgggta atccacgct aatgaaagtt ttatccggaa tacatgagcc gaccaaaggc    180
accattacca ttaataacat tagctataac aagctggatc ataaattagc ggcacaactc    240
ggtatcggga ttatttatca ggaactcagc gttattgatg aattaaccgt actggaaaat    300
ttatatattg gtcgtcatct gacgaaaaaa atctgtggcg tcaatattat cgactggcga    360
gaaatgcgtg tccgcgccgc catgatgtta ttacgcgtgg gcttgaaagt tgatctagat    420
gagaaagtgg cgaatttatc tatcagccac aagcagatgc tagaaattgc caaaacgctg    480
atgctcgatg ccaaagtcat catcatggat gaacccacct cctcactcac caataaagag    540
gtggactatc tgtttctgat catgaatcag ttgcgtaaag agggtacggc catcgtctat    600
atctcgcata agttggcgga aattcgccgt atttgcgacc gctatacggt gatgaaagac    660
ggcagcagcg tttgcagcgg catagtaagc gatgtgtcaa atgacgatat cgtccgtctg    720
atggtaggcc gcgaactgca aaaccgtttt aacgcgatga aggagaatgt cagcaacctt    780
gcgcacgaaa cggttttga ggtgcggaac gtcaccagtc gtgacagaaa aaaggtccgg    840
gatatctcat ttagcgtctg ccggggagaa atattaggct ttgccggact ggtcggttcc    900
ggacgtactg aactgatgaa ttgtctgttt ggcgtggata acgcgctgg cggagaaatc    960 cgtcttaatg gcaaagatat ctctccacgt tcacccctgg atgccgtgaa aaagggatg    1020 gcttacatca ctgaaagccg ccgggataac ggttttttcc ccaactttc catcgctcag    1080 aacatggcga tcagccgcag tctgaaagac ggcggctata aaggcgcgat gggcttgttt    1140
catgaagttg acgagcaacg taccgctgaa aatcaacgcg aactgctggc gctgaaatgt    1200
cattcggtaa accagaatat caccgaactc tccgggggaa atcagcagaa agtcctgatc    1260
tccaaatggc tgtgctgttg cccggaagtg attattttcg atgaacctac ccgcggcatc    1320
gacgttggcg cgaaagccga aatttacaaa gtgatgcgcc aactggcgga cgacggaaaa    1380
gtcatcctga tggtgtcatc tgaactacct gaaattatca ccgtctgcga ccgcatcgcc    1440
gtgttctgcg aaggacgact gacgcaaatc ctgacgaatc gcgatgacat gagcgaagag    1500
gagattatgg catgggcttt accacaagag taa                                 1533
```

<210> SEQ ID NO 17
<211> LENGTH: 981
<212> TYPE: DNA
<213> ORGANISM: Escherichia coli

<400> SEQUENCE: 17

```
atgggcttta ccacaagagt aaaaagcgaa gcgagcgaga agaaaccgtt caactttgcg      60
ctgttctggg ataaatacgg cacctttttt atcctggcga tcatcgtcgc catctttggt     120
tcgctgtcac cagaatattt tctgaccacc aataatatta cccagatttt tgttcaaagc     180
tccgtgacgg tattgatcgg catgggcgag ttttcgcta tcctggtcgc tggtatcgac      240
ctctcggttg gcgcgattct ggcgctttcc ggtatggtga ccgccaaact gatgttggca     300
ggtgttgacc cgtttctcgc agcgatgatt ggcggtgtac tggttggcgg cgcactgggg     360
gcgatcaacg gctgcctggt caactggacg gggctacacc cgttcatcat caccccttggc   420
accaacgcga ttttccgtgg gatcacgctg gtgatctccg atgccaactc ggtatacggc     480
ttctcatttg acttcgtgaa cttctttgcc gccagcgtaa ttgggatacc tgtccccgtt     540
atcttctcac taattgtcgc gctcatcctt tggtttctga caacgcgtat gcggctcggg     600
cgcaacatct acgcactggg cggcaacaaa aattcggcgt tctattccgg gattgacgtg     660
aaattccaca tcctggtggt gtttatcatc tccggtgttt gtgcaggtct ggcaggcgtc     720
gtctcaactg cacgactcgg tgccgcagaa ccgcttgccg gtatgggttt tgaaacctat     780
gccattgcca gcgccatcat tggcggcacc agtttcttcg gcggcaaggg gcgcattttc     840
tctgtggtga ttggcgggtt gatcatcggc accatcaaca acggtctgaa tattttgcag     900
gtacaaacct attaccaact ggtggtgatg ggcggattaa ttatcgcggc tgtcgccctt     960
gaccgtctta tcagtaagta a                                               981

<210> SEQ ID NO 18
<211> LENGTH: 696
<212> TYPE: DNA
<213> ORGANISM: Escherichia coli

<400> SEQUENCE: 18
atgaaaatct cccctcgtt aatgtgtatg gatctgctga aatttaaaga acagatcgaa       60
tttatcgaca gccatgccga ttacttccac atcgatatca tggacggtca ctttgtcccc    120
aatctgacac tctcaccgtt cttcgtaagt caggttaaaa aactggcaac taaaccgctc    180
gactgtcatc tgatggtgac gcggccgcag gattacattg ctcaactggc gcgtgcggga    240
gcagatttca tcactctgca tccggaaacc atcaacggcc aggcgttccg cctgattgat    300
gaaatccgcc gtcatgacat gaagtgggg ctgatcctta acccgagac gccagttgag     360
gccatgaaat actatatcca taaggccgat aaaattacgg tcatgactgt cgatcccggc    420
tttgccggac aaccgttcat tcctgaaatg ctggataaac ttgccgaact gaaggcatgg    480
cgtgaacgag aaggtctgga gtacgaaatt gaggtggacg gttcctgcaa ccaggcaact    540
tacgaaaaac tgatggcggc aggggcggat gtctttatcg tcggcacttc cggcctgttt    600
aatcatgcgg aaaatatcga cgaagcatgg agaattatga ccgcgcagat tctggctgca    660
aaaagcgagg tacagcctca tgcaaaaaca gcataa                              696

<210> SEQ ID NO 19
<211> LENGTH: 930
<212> TYPE: DNA
<213> ORGANISM: Escherichia coli

<400> SEQUENCE: 19
atgcaaaaac agcataacgt cgtagcgggc gtggatatgg gggcaacgca tatccgcttt      60
tgtctgcgga cagcagaagg tgaaacgcta cactgcgaaa aaagcggac cgcagaagtc    120
```

-continued

```
attgctcccg gcctggtgtc gggtatcggc gaaatgattg acgagcaact caggcgcttt      180
aacgctcgct gtcatggtct ggtgatggga tttccggcgc tggtcagtaa agataaacgc      240
accattattt ctacgcctaa cctgccgtta acagccggcgg atttatatga tctcgccgat     300
aagctcgaaa atacgctgaa ttgtccggtt gagttttccc gcgacgttaa cctgcaactc      360
tcctgggacg tagtagaaaa ccgccttacg caacaactgg ttctggcggc ctatctcggt      420
acggggatgg ggttcgcagt gtggatgaac ggtgcgccgt ggacgggtgc acacggtgtg      480
gcaggcgaac tgggtcatat cccctggga gatatgaccc aacactgcgc gtgtggcaat       540
cctgggtgcc tggaaaccaa ttgctctgga atggcgctaa acgctggta cgaacaacag       600 ccccgaaatt acccattgcg cgatcttttc gtccatgcgg aaaacgcccc tttcgtccag      660
agtctgcttg aaaacgcggc acgggccatt gccaccagca ttaatctgtt cgatcccgat      720
gcggtgatcc tgggcggtgg cgtgatggat atgcccgcct tcccacgcga gactctcgtt      780
gccatgaccc aaaagtacct gcgccgtcca ctgccgcatc aggtcgtgcg ctttattgcc      840
gcctcatctt ctgactttaa tggcgctcag ggtgcagcaa tattggcgca tcaacgtttt      900
ttgccacagt tctgtgctaa agccccatga                                       930
```

<210> SEQ ID NO 20
<211> LENGTH: 149
<212> TYPE: PRT
<213> ORGANISM: Escherichia coli

<400> SEQUENCE: 20

Met Lys Lys Ile Ala Phe Gly Cys Asp His Val Gly Phe Ile Leu Lys
1               5                   10                  15

His Glu Ile Val Ala His Leu Val Glu Arg Gly Val Glu Val Ile Asp
                20                  25                  30

Lys Gly Thr Trp Ser Ser Glu Arg Thr Asp Tyr Pro His Tyr Ala Ser
            35                  40                  45

Gln Val Ala Leu Ala Val Ala Gly Gly Glu Val Asp Gly Gly Ile Leu
        50                  55                  60

Ile Cys Gly Thr Gly Val Gly Ile Ser Ile Ala Ala Asn Lys Phe Ala
65                  70                  75                  80

Gly Ile Arg Ala Val Val Cys Ser Glu Pro Tyr Ser Ala Gln Leu Ser
                85                  90                  95

Arg Gln His Asn Asp Thr Asn Val Leu Ala Phe Gly Ser Arg Val Val
                100                 105                 110

Gly Leu Glu Leu Ala Lys Met Ile Val Asp Ala Trp Leu Gly Ala Gln
            115                 120                 125

Tyr Glu Gly Gly Arg His Gln Gln Arg Val Glu Ala Ile Thr Ala Ile
        130                 135                 140

Glu Gln Arg Arg Asn
145

<210> SEQ ID NO 21
<211> LENGTH: 296
<212> TYPE: PRT
<213> ORGANISM: Escherichia coli

<400> SEQUENCE: 21

Met Ser Gln Ser Glu Phe Asp Ser Ala Leu Pro Asn Gly Ile Gly Leu
1               5                   10                  15

Ala Pro Tyr Leu Arg Met Lys Gln Glu Gly Met Thr Glu Asn Glu Ser
                20                  25                  30

Arg Ile Val Glu Trp Leu Leu Lys Pro Gly Asn Leu Ser Cys Ala Pro
            35                  40                  45

Ala Ile Lys Asp Val Ala Glu Ala Leu Ala Val Ser Glu Ala Met Ile
    50                  55                  60

Val Lys Val Ser Lys Leu Leu Gly Phe Ser Gly Phe Arg Asn Leu Arg
65                  70                  75                  80

Ser Ala Leu Glu Asp Tyr Phe Ser Gln Ser Glu Gln Val Leu Pro Ser
                85                  90                  95

Glu Leu Ala Phe Asp Glu Ala Pro Gln Asp Val Val Asn Lys Val Phe
            100                 105                 110

Asn Ile Thr Leu Arg Thr Ile Met Glu Gly Gln Ser Ile Val Asn Val
            115                 120                 125

Asp Glu Ile His Arg Ala Ala Arg Phe Phe Tyr Gln Ala Arg Gln Arg
130                 135                 140

Asp Leu Tyr Gly Ala Gly Gly Ser Asn Ala Ile Cys Ala Asp Val Gln
145                 150                 155                 160

His Lys Phe Leu Arg Ile Gly Val Arg Cys Gln Ala Tyr Pro Asp Ala
                165                 170                 175

His Ile Met Met Met Ser Ala Ser Leu Leu Gln Glu Gly Asp Val Val
            180                 185                 190

Leu Val Val Thr His Ser Gly Arg Thr Ser Asp Val Lys Ala Ala Val
            195                 200                 205

Glu Leu Ala Lys Lys Asn Gly Ala Lys Ile Ile Cys Ile Thr His Ser
    210                 215                 220

Tyr His Ser Pro Ile Ala Lys Leu Ala Asp Tyr Ile Ile Cys Ser Pro
225                 230                 235                 240

Ala Pro Glu Thr Pro Leu Leu Gly Arg Asn Ala Ser Ala Arg Ile Leu
                245                 250                 255

Gln Leu Thr Leu Leu Asp Ala Phe Phe Val Ser Val Ala Gln Leu Asn
            260                 265                 270

Ile Glu Gln Ala Asn Ile Asn Met Gln Lys Thr Gly Ala Ile Val Asp
            275                 280                 285

Phe Phe Ser Pro Gly Ala Leu Lys
            290                 295

<210> SEQ ID NO 22
<211> LENGTH: 311
<212> TYPE: PRT
<213> ORGANISM: Escherichia coli

<400> SEQUENCE: 22

Met Asn Lys Tyr Leu Lys Tyr Phe Ser Gly Thr Leu Val Gly Leu Met
1               5                   10                  15

Leu Ser Thr Ser Ala Phe Ala Ala Glu Tyr Ala Val Val Leu Lys
                20                  25                  30

Thr Leu Ser Asn Pro Phe Trp Val Asp Met Lys Lys Gly Ile Glu Asp
            35                  40                  45

Glu Ala Lys Thr Leu Gly Val Ser Val Asp Ile Phe Ala Ser Pro Ser
    50                  55                  60

Glu Gly Asp Phe Gln Ser Gln Leu Gln Leu Phe Glu Asp Leu Ser Asn
65                  70                  75                  80

Lys Asn Tyr Lys Gly Ile Ala Phe Ala Pro Leu Ser Ser Val Asn Leu
                85                  90                  95

Val Met Pro Val Ala Arg Ala Trp Lys Lys Gly Ile Tyr Leu Val Asn

```
            100                 105                 110
Leu Asp Glu Lys Ile Asp Met Asp Asn Leu Lys Lys Ala Gly Gly Asn
            115                 120                 125

Val Glu Ala Phe Val Thr Thr Asp Asn Val Ala Val Gly Ala Lys Gly
            130                 135                 140

Ala Ser Phe Ile Ile Asp Lys Leu Gly Ala Glu Gly Glu Val Ala
145                 150                 155                 160

Ile Ile Glu Gly Lys Ala Gly Asn Ala Ser Gly Glu Ala Arg Arg Asn
            165                 170                 175

Gly Ala Thr Glu Ala Phe Lys Lys Ala Ser Gln Ile Lys Leu Val Ala
            180                 185                 190

Ser Gln Pro Ala Asp Trp Asp Arg Ile Lys Ala Leu Asp Val Ala Thr
            195                 200                 205

Asn Val Leu Gln Arg Asn Pro Asn Ile Lys Ala Ile Tyr Cys Ala Asn
            210                 215                 220

Asp Thr Met Ala Met Gly Val Ala Gln Ala Val Ala Asn Ala Gly Lys
225                 230                 235                 240

Thr Gly Lys Val Leu Val Val Gly Thr Asp Gly Ile Pro Glu Ala Arg
            245                 250                 255

Lys Met Val Glu Ala Gly Gln Met Thr Ala Thr Val Ala Gln Asn Pro
            260                 265                 270

Ala Asp Ile Gly Ala Thr Gly Leu Lys Leu Met Val Asp Ala Glu Lys
            275                 280                 285

Ser Gly Lys Val Ile Pro Leu Asp Lys Ala Pro Glu Phe Lys Leu Val
            290                 295                 300

Asp Ser Ile Leu Val Thr Gln
305                 310

<210> SEQ ID NO 23
<211> LENGTH: 326
<212> TYPE: PRT
<213> ORGANISM: Escherichia coli

<400> SEQUENCE: 23

Met Gly Phe Thr Thr Arg Val Lys Ser Glu Ala Ser Glu Lys Lys Pro
1               5                   10                  15

Phe Asn Phe Ala Leu Phe Trp Asp Lys Tyr Gly Thr Phe Phe Ile Leu
            20                  25                  30

Ala Ile Ile Val Ala Ile Phe Gly Ser Leu Ser Pro Glu Tyr Phe Leu
            35                  40                  45

Thr Thr Asn Asn Ile Thr Gln Ile Phe Val Gln Ser Ser Val Thr Val
            50                  55                  60

Leu Ile Gly Met Gly Glu Phe Phe Ala Ile Leu Val Ala Gly Ile Asp
65                  70                  75                  80

Leu Ser Val Gly Ala Ile Leu Ala Leu Ser Gly Met Val Thr Ala Lys
            85                  90                  95

Leu Met Leu Ala Gly Val Asp Pro Phe Leu Ala Ala Met Ile Gly Gly
            100                 105                 110

Val Leu Val Gly Gly Ala Leu Gly Ala Ile Asn Gly Cys Leu Val Asn
            115                 120                 125

Trp Thr Gly Leu His Pro Phe Ile Ile Thr Leu Gly Thr Asn Ala Ile
            130                 135                 140

Phe Arg Gly Ile Thr Leu Val Ile Ser Asp Ala Asn Ser Val Tyr Gly
145                 150                 155                 160
```

```
Phe Ser Phe Asp Phe Val Asn Phe Ala Ala Ser Val Ile Gly Ile
            165                 170                 175

Pro Val Pro Val Ile Phe Ser Leu Ile Val Ala Leu Ile Leu Trp Phe
            180                 185                 190

Leu Thr Thr Arg Met Arg Leu Gly Arg Asn Ile Tyr Ala Leu Gly Gly
            195                 200                 205

Asn Lys Asn Ser Ala Phe Tyr Ser Gly Ile Asp Val Lys Phe His Ile
            210                 215                 220

Leu Val Val Phe Ile Ile Ser Gly Val Cys Ala Gly Leu Ala Gly Val
225                 230                 235                 240

Val Ser Thr Ala Arg Leu Gly Ala Ala Glu Pro Leu Ala Gly Met Gly
            245                 250                 255

Phe Glu Thr Tyr Ala Ile Ala Ser Ala Ile Ile Gly Gly Thr Ser Phe
            260                 265                 270

Phe Gly Gly Lys Gly Arg Ile Phe Ser Val Val Ile Gly Gly Leu Ile
            275                 280                 285

Ile Gly Thr Ile Asn Asn Gly Leu Asn Ile Leu Gln Val Gln Thr Tyr
            290                 295                 300

Tyr Gln Leu Val Val Met Gly Gly Leu Ile Ile Ala Ala Val Ala Leu
305                 310                 315                 320

Asp Arg Leu Ile Ser Lys
            325

<210> SEQ ID NO 24
<211> LENGTH: 326
<212> TYPE: PRT
<213> ORGANISM: Escherichia coli

<400> SEQUENCE: 24

Met Gly Phe Thr Thr Arg Val Lys Ser Glu Ala Ser Glu Lys Lys Pro
1               5                   10                  15

Phe Asn Phe Ala Leu Phe Trp Asp Lys Tyr Gly Thr Phe Phe Ile Leu
            20                  25                  30

Ala Ile Ile Val Ala Ile Phe Gly Ser Leu Ser Pro Glu Tyr Phe Leu
            35                  40                  45

Thr Thr Asn Asn Ile Thr Gln Ile Phe Val Gln Ser Ser Val Thr Val
        50                  55                  60

Leu Ile Gly Met Gly Glu Phe Ala Ile Leu Val Ala Gly Ile Asp
65                  70                  75                  80

Leu Ser Val Gly Ala Ile Leu Ala Leu Ser Gly Met Val Thr Ala Lys
            85                  90                  95

Leu Met Leu Ala Gly Val Asp Pro Phe Leu Ala Ala Met Ile Gly Gly
            100                 105                 110

Val Leu Val Gly Gly Ala Leu Gly Ala Ile Asn Gly Cys Leu Val Asn
            115                 120                 125

Trp Thr Gly Leu His Pro Phe Ile Ile Thr Leu Gly Thr Asn Ala Ile
            130                 135                 140

Phe Arg Gly Ile Thr Leu Val Ile Ser Asp Ala Asn Ser Val Tyr Gly
145                 150                 155                 160

Phe Ser Phe Asp Phe Val Asn Phe Ala Ala Ser Val Ile Gly Ile
            165                 170                 175

Pro Val Pro Val Ile Phe Ser Leu Ile Val Ala Leu Ile Leu Trp Phe
            180                 185                 190

Leu Thr Thr Arg Met Arg Leu Gly Arg Asn Ile Tyr Ala Leu Gly Gly
            195                 200                 205
```

```
Asn Lys Asn Ser Ala Phe Tyr Ser Gly Ile Asp Val Lys Phe His Ile
        210                 215                 220

Leu Val Val Phe Ile Ile Ser Gly Val Cys Ala Gly Leu Ala Gly Val
225                 230                 235                 240

Val Ser Thr Ala Arg Leu Gly Ala Ala Glu Pro Leu Ala Gly Met Gly
                245                 250                 255

Phe Glu Thr Tyr Ala Ile Ala Ser Ala Ile Gly Gly Thr Ser Phe
                260                 265                 270

Phe Gly Gly Lys Gly Arg Ile Phe Ser Val Val Ile Gly Gly Leu Ile
                275                 280                 285

Ile Gly Thr Ile Asn Asn Gly Leu Asn Ile Leu Gln Val Gln Thr Tyr
            290                 295                 300

Tyr Gln Leu Val Val Met Gly Gly Leu Ile Ile Ala Ala Val Ala Leu
305                 310                 315                 320

Asp Arg Leu Ile Ser Lys
                325

<210> SEQ ID NO 25
<211> LENGTH: 309
<212> TYPE: PRT
<213> ORGANISM: Escherichia coli

<400> SEQUENCE: 25

Met Gln Lys Gln His Asn Val Val Ala Gly Val Asp Met Gly Ala Thr
1               5                   10                  15

His Ile Arg Phe Cys Leu Arg Thr Ala Glu Gly Glu Thr Leu His Cys
            20                  25                  30

Glu Lys Lys Arg Thr Ala Glu Val Ile Ala Pro Gly Leu Val Ser Gly
        35                  40                  45

Ile Gly Glu Met Ile Asp Glu Gln Leu Arg Arg Phe Asn Ala Arg Cys
    50                  55                  60

His Gly Leu Val Met Gly Phe Pro Ala Leu Val Ser Lys Asp Lys Arg
65                  70                  75                  80

Thr Ile Ile Ser Thr Pro Asn Leu Pro Leu Thr Ala Ala Asp Leu Tyr
                85                  90                  95

Asp Leu Ala Asp Lys Leu Glu Asn Thr Leu Asn Cys Pro Val Glu Phe
            100                 105                 110

Ser Arg Asp Val Asn Leu Gln Leu Ser Trp Asp Val Val Glu Asn Arg
        115                 120                 125

Leu Thr Gln Gln Leu Val Leu Ala Ala Tyr Leu Gly Thr Gly Met Gly
    130                 135                 140

Phe Ala Val Trp Met Asn Gly Ala Pro Trp Thr Gly Ala His Gly Val
145                 150                 155                 160

Ala Gly Glu Leu Gly His Ile Pro Leu Gly Asp Met Thr Gln His Cys
                165                 170                 175

Ala Cys Gly Asn Pro Gly Cys Leu Glu Thr Asn Cys Ser Gly Met Ala
            180                 185                 190

Leu Arg Arg Trp Tyr Glu Gln Gln Pro Arg Asn Tyr Pro Leu Arg Asp
        195                 200                 205

Leu Phe Val His Ala Glu Asn Ala Pro Phe Val Gln Ser Leu Leu Glu
    210                 215                 220

Asn Ala Ala Arg Ala Ile Ala Thr Ser Ile Asn Leu Phe Asp Pro Asp
225                 230                 235                 240

Ala Val Ile Leu Gly Gly Gly Val Met Asp Met Pro Ala Phe Pro Arg
```

```
                245                 250                 255
Glu Thr Leu Val Ala Met Thr Gln Lys Tyr Leu Arg Arg Pro Leu Pro
            260                 265                 270

His Gln Val Val Arg Phe Ile Ala Ala Ser Ser Asp Phe Asn Gly
        275                 280                 285

Ala Gln Gly Ala Ala Ile Leu Ala His Gln Arg Phe Leu Pro Gln Phe
    290                 295                 300

Cys Ala Lys Ala Pro
305

<210> SEQ ID NO 26
<211> LENGTH: 309
<212> TYPE: PRT
<213> ORGANISM: Escherichia coli

<400> SEQUENCE: 26

Met Gln Lys Gln His Asn Val Val Ala Gly Val Asp Met Gly Ala Thr
1               5                   10                  15

His Ile Arg Phe Cys Leu Arg Thr Ala Glu Gly Glu Thr Leu His Cys
            20                  25                  30

Glu Lys Lys Arg Thr Ala Glu Val Ile Ala Pro Gly Leu Val Ser Gly
        35                  40                  45

Ile Gly Glu Met Ile Asp Glu Gln Leu Arg Arg Phe Asn Ala Arg Cys
    50                  55                  60

His Gly Leu Val Met Gly Phe Pro Ala Leu Val Ser Lys Asp Lys Arg
65              70                  75                  80

Thr Ile Ile Ser Thr Pro Asn Leu Pro Leu Thr Ala Ala Asp Leu Tyr
            85                  90                  95

Asp Leu Ala Asp Lys Leu Glu Asn Thr Leu Asn Cys Pro Val Glu Phe
        100                 105                 110

Ser Arg Asp Val Asn Leu Gln Leu Ser Trp Asp Val Val Glu Asn Arg
    115                 120                 125

Leu Thr Gln Gln Leu Val Leu Ala Ala Tyr Leu Gly Thr Gly Met Gly
130                 135                 140

Phe Ala Val Trp Met Asn Gly Ala Pro Trp Thr Gly Ala His Gly Val
145                 150                 155                 160

Ala Gly Glu Leu Gly His Ile Pro Leu Gly Asp Met Thr Gln His Cys
            165                 170                 175

Ala Cys Gly Asn Pro Gly Cys Leu Glu Thr Asn Cys Ser Gly Met Ala
        180                 185                 190

Leu Arg Arg Trp Tyr Glu Gln Gln Pro Arg Asn Tyr Pro Leu Arg Asp
    195                 200                 205

Leu Phe Val His Ala Glu Asn Ala Pro Phe Val Gln Ser Leu Leu Glu
210                 215                 220

Asn Ala Ala Arg Ala Ile Ala Thr Ser Ile Asn Leu Phe Asp Pro Asp
225                 230                 235                 240

Ala Val Ile Leu Gly Gly Gly Val Met Asp Met Pro Ala Phe Pro Arg
            245                 250                 255

Glu Thr Leu Val Ala Met Thr Gln Lys Tyr Leu Arg Arg Pro Leu Pro
        260                 265                 270

His Gln Val Val Arg Phe Ile Ala Ala Ser Ser Asp Phe Asn Gly
    275                 280                 285

Ala Gln Gly Ala Ala Ile Leu Ala His Gln Arg Phe Leu Pro Gln Phe
    290                 295                 300
```

Cys Ala Lys Ala Pro
305

<210> SEQ ID NO 27
<211> LENGTH: 2067
<212> TYPE: DNA
<213> ORGANISM: corynebacterium

<400> SEQUENCE: 27

| | | | | | |
|---|---|---|---|---|---|
| atgaatagcg | taaataattc | ctcgcttgtc | cggctggatg | tcgatttcgg | cgactccacc | 60 |
| acggatgtca | tcaacaacct | tgccactgtt | attttcgacg | ctggccgagc | ttcctccgcc | 120 |
| gacgcccttg | ccaaagacgc | gctggatcgt | gaagcaaagt | ccggcaccgg | cgttcctggt | 180 |
| caagttgcta | tccccactg | ccgttccgaa | gccgtatctg | tccctacctt | gggctttgct | 240 |
| cgcctgagca | agggtgtgga | cttcagcgga | cctgatggcg | atgccaactt | ggtgttcctc | 300 |
| attgcagcac | ctgctggcgg | cggcaaagag | cacctgaaga | tcctgtccaa | gcttgctcgc | 360 |
| tccttggtga | agaaggattt | catcaaggct | ctgcaggaag | ccaccaccga | gcaggaaatc | 420 |
| gtcgacgttg | tcgatgccgt | gctcaaccca | gcaccaaaaa | ccaccgagcc | agctgcagct | 480 |
| ccggctgcgg | cggcggttgc | tgagagtggg | gcggcgtcga | caagcgttac | tcgtatcgtg | 540 |
| gcaatcaccg | catgcccaac | cggtatcgca | cacacctaca | tggctgcgga | ttccctgacg | 600 |
| caaaacgcgg | aaggccgcga | tgatgtgaa | ctcgttgtgg | agactcaggg | ctcttccgct | 660 |
| gtcaccccag | tcgatccgaa | gatcatcgaa | gctgccgacg | ccgtcatctt | cgccaccgac | 720 |
| gtgggagtta | agaccgcga | gcgtttcgct | ggcaagccag | tcattgaatc | cggcgtcaag | 780 |
| cgcgcgatca | atgagccagc | caagatgatc | gacgaggcca | tcgcagcctc | caagaaccca | 840 |
| aacgcccgca | aggtttccgg | ttccggtgtc | gcggcatctg | ctgaaaccac | cggcgagaag | 900 |
| ctcggctggg | gcaagcgcat | ccagcaggca | gtcatgaccg | gcgtgtccta | catggttcca | 960 |
| ttcgtagctg | ccggcggcct | cctgttggct | ctcggcttcg | cattcggtgg | atacgacatg | 1020 |
| gcgaacggct | ggcaagcaat | cgccacccag | ttctctctga | ccaacctgcc | aggcaacacc | 1080 |
| gtcgatgttg | acggcgtggc | catgaccttc | gagcgttcag | gcttcctgtt | gtacttcggc | 1140 |
| gcagtcctgt | tcgccaccgg | ccaagcagcc | atgggcttca | tcgtggcagc | cctgtctggc | 1200 |
| tacaccgcat | acgcacttgc | tggacgccca | ggcatcgcgc | cgggcttcgt | cggtggcgcc | 1260 |
| atctccgtca | ccatcggcgc | tggcttcatt | ggtggtctgg | ttaccggtat | cttggctggt | 1320 |
| ctcattgccc | tgtggattgg | ctcctggaag | gtgccacgcg | tggtgcagtc | actgatgcct | 1380 |
| gtggtcatca | tcccgctact | tacctcagtg | ttgttggtc | tcgtcatgta | cctcctgctg | 1440 |
| ggtcgcccac | tcgcatccat | catgactggt | ttgcaggact | ggctatcgtc | aatgtccgga | 1500 |
| agctccgcca | tcttgctggg | tatcatcttg | gcctcatga | tgtgtttcga | cctcggcgga | 1560 |
| ccagtaaaca | aggcagccta | cctctttggt | accgcaggcc | tgtctaccgg | cgaccaagct | 1620 |
| tccatggaaa | tcatggccgc | gatcatgca | gctggcatgg | tcccaccaat | cgcgttgtcc | 1680 |
| attgctaccc | tgctgcgcaa | gaagctgttc | accccagcag | agcaagaaaa | cggcaagtct | 1740 |
| tcctggctgc | ttggcctggc | attcgtctcc | gaaggtgcca | tcccattcgc | cgcagctgac | 1800 |
| ccattccgtg | tgatcccagc | aatgatggct | ggcggtgcaa | ccactggtgc | aatctccatg | 1860 |
| gcactgggcg | tcggctctcg | ggctccacac | ggcggtatct | tcgtggtctg | gcaatcgaa | 1920 |
| ccatggtggg | gctggctcat | cgcacttgca | gcaggcacca | tcgtgtccac | catcgttgtc | 1980 |
| atcgcactga | agcagttctg | gccaaacaag | gccgtcgctg | cagaagtcgc | gaagcaagaa | 2040 | gcacaacaag cagctgtaaa cgcataa 2067

<210> SEQ ID NO 28
<211> LENGTH: 688
<212> TYPE: PRT
<213> ORGANISM: corynebacterium

<400> SEQUENCE: 28

```
Met Asn Ser Val Asn Ser Ser Leu Val Arg Leu Asp Val Asp Phe
1               5                   10                  15

Gly Asp Ser Thr Thr Asp Val Ile Asn Asn Leu Ala Thr Val Ile Phe
            20                  25                  30

Asp Ala Gly Arg Ala Ser Ser Ala Asp Ala Leu Ala Lys Asp Ala Leu
                35                  40                  45

Asp Arg Glu Ala Lys Ser Gly Thr Gly Val Pro Gly Gln Val Ala Ile
50                  55                  60

Pro His Cys Arg Ser Glu Ala Val Ser Val Pro Thr Leu Gly Phe Ala
65                  70                  75                  80

Arg Leu Ser Lys Gly Val Asp Phe Ser Gly Pro Asp Gly Asp Ala Asn
                85                  90                  95

Leu Val Phe Leu Ile Ala Ala Pro Ala Gly Gly Gly Lys Glu His Leu
            100                 105                 110

Lys Ile Leu Ser Lys Leu Ala Arg Ser Leu Val Lys Lys Asp Phe Ile
        115                 120                 125

Lys Ala Leu Gln Glu Ala Thr Thr Glu Gln Glu Ile Val Asp Val Val
130                 135                 140

Asp Ala Val Leu Asn Pro Ala Pro Lys Thr Thr Glu Pro Ala Ala Ala
145                 150                 155                 160

Pro Ala Ala Ala Val Ala Glu Ser Gly Ala Ala Ser Thr Ser Val
                165                 170                 175

Thr Arg Ile Val Ala Ile Thr Ala Cys Pro Thr Gly Ile Ala His Thr
            180                 185                 190

Tyr Met Ala Ala Asp Ser Leu Thr Gln Asn Ala Glu Gly Arg Asp Asp
        195                 200                 205

Val Glu Leu Val Val Glu Thr Gln Gly Ser Ser Ala Val Thr Pro Val
210                 215                 220

Asp Pro Lys Ile Ile Glu Ala Ala Asp Ala Val Ile Phe Ala Thr Asp
225                 230                 235                 240

Val Gly Val Lys Asp Arg Glu Arg Phe Ala Gly Lys Pro Val Ile Glu
                245                 250                 255

Ser Gly Val Lys Arg Ala Ile Asn Glu Pro Ala Lys Met Ile Asp Glu
            260                 265                 270

Ala Ile Ala Ala Ser Lys Asn Pro Asn Ala Arg Lys Val Ser Gly Ser
        275                 280                 285

Gly Val Ala Ala Ser Ala Glu Thr Thr Gly Glu Lys Leu Gly Trp Gly
290                 295                 300

Lys Arg Ile Gln Gln Ala Val Met Thr Gly Val Ser Tyr Met Val Pro
305                 310                 315                 320

Phe Val Ala Ala Gly Gly Leu Leu Leu Ala Leu Gly Phe Ala Phe Gly
                325                 330                 335

Gly Tyr Asp Met Ala Asn Gly Trp Gln Ala Ile Ala Thr Gln Phe Ser
            340                 345                 350

Leu Thr Asn Leu Pro Gly Asn Thr Val Asp Val Asp Gly Val Ala Met
        355                 360                 365
```

Thr Phe Glu Arg Ser Gly Phe Leu Leu Tyr Phe Gly Ala Val Leu Phe
370                 375                 380

Ala Thr Gly Gln Ala Ala Met Gly Phe Ile Val Ala Ala Leu Ser Gly
385                 390                 395                 400

Tyr Thr Ala Tyr Ala Leu Ala Gly Arg Pro Gly Ile Ala Pro Gly Phe
            405                 410                 415

Val Gly Gly Ala Ile Ser Val Thr Ile Gly Ala Gly Phe Ile Gly Gly
            420                 425                 430

Leu Val Thr Gly Ile Leu Ala Gly Leu Ile Ala Leu Trp Ile Gly Ser
            435                 440                 445

Trp Lys Val Pro Arg Val Val Gln Ser Leu Met Pro Val Val Ile Ile
450                 455                 460

Pro Leu Leu Thr Ser Val Val Gly Leu Val Met Tyr Leu Leu Leu
465                 470                 475                 480

Gly Arg Pro Leu Ala Ser Ile Met Thr Gly Leu Gln Asp Trp Leu Ser
            485                 490                 495

Ser Met Ser Gly Ser Ser Ala Ile Leu Leu Gly Ile Ile Leu Gly Leu
            500                 505                 510

Met Met Cys Phe Asp Leu Gly Gly Pro Val Asn Lys Ala Ala Tyr Leu
            515                 520                 525

Phe Gly Thr Ala Gly Leu Ser Thr Gly Asp Gln Ala Ser Met Glu Ile
530                 535                 540

Met Ala Ala Ile Met Ala Ala Gly Met Val Pro Pro Ile Ala Leu Ser
545                 550                 555                 560

Ile Ala Thr Leu Leu Arg Lys Lys Leu Phe Thr Pro Ala Glu Gln Glu
            565                 570                 575

Asn Gly Lys Ser Ser Trp Leu Leu Gly Leu Ala Phe Val Ser Glu Gly
            580                 585                 590

Ala Ile Pro Phe Ala Ala Ala Asp Pro Phe Arg Val Ile Pro Ala Met
            595                 600                 605

Met Ala Gly Gly Ala Thr Thr Gly Ala Ile Ser Met Ala Leu Gly Val
            610                 615                 620

Gly Ser Arg Ala Pro His Gly Gly Ile Phe Val Val Trp Ala Ile Glu
625                 630                 635                 640

Pro Trp Trp Gly Trp Leu Ile Ala Leu Ala Ala Gly Thr Ile Val Ser
            645                 650                 655

Thr Ile Val Val Ile Ala Leu Lys Gln Phe Trp Pro Asn Lys Ala Val
            660                 665                 670

Ala Ala Glu Val Ala Lys Gln Glu Ala Gln Gln Ala Ala Val Asn Ala
            675                 680                 685

<210> SEQ ID NO 29
<211> LENGTH: 1512
<212> TYPE: DNA
<213> ORGANISM: corynebacterium

<400> SEQUENCE: 29
atgaacaccc cactccagct caacactgaa aacctgcagg aaatcgcttc gacttccgga      60
gtgcagatcc cagcgttcaa ccgcgctgac gtcgccccgg gcattgtcca cttcggtgtt     120
ggcggattcc atcgcgctca ccaagcgatg tacctcaatg aattgatgaa tgagggcaag     180
gccttggatt gggcatcat cggcatgggt gtcatgcctt ccgatgtgcg catgcgcgat     240
gccctggcca gccaagatca cctttatacc ctgaccacta agctcctga tggaactctt     300 gatcaaaaaa tcatcggatc catcattgac tacgtgttcg ctcccgagga cccagcacgg     360

-continued

```
gccgttgcaa ccctcgcgca ggactccatc cgcattgttt ccctcacggt gactgaaggc    420
ggatacaaca tcgatccggc gacagaagat ttcgaccaca ccaaccctcg aatcgttgct    480
gaccgcgaag ccctgcaggc gggcgatact tccactttgc agaccttctt tgggttgatc    540
actgccgcat tgatttcccg aaaagaatca ggatctacgc catttaccat catgagctgc    600
gataacatcc aaggcaacgg cgatctggct aagcgtttct tcctcgcctt cgcacattcc    660
gtgtcttctg agctcggcga atgggtggaa acaacgtgg ccttcccaa ctccatggtg      720 gaccgcatca cccctgaaac caccgacggc gaccgcgatg acatcaagga aatcggctac    780
atcgatgcgt ggccagtggt ttctgaagat ttcacccaat gggtcctcga ggatgccttc    840
acccagggcc gccccgcgta cgaggaggtt ggcgtgcagg tcgtctccga cgtggagcct    900
tatgaattaa tgaagctgcg cctgctcaac gcctcccacc agggactttg ctacttcggc    960
cacttggctg ccaccacat ggtccacgac gtcatggcgg ataccgctt ccaggatttc     1020 ctcctggctt acatggagcg cgaagccacc cctaccctca aggaacttcc aggtgtcgat   1080
ctagatgctt atcgacgcca actcatcgcg cgattcggca acgccgcagt caaagacacc   1140
gtaccgcgcc tgtgtgcgga atcctccgac cgcattccaa agtggctgtt gccagtcgta   1200
cgcgaaaacc tcgcagcagg ccgcgacgtc acactttctg cagccatcgt cgcatcctgg   1260
gcgcgctacg cagaaggcac cgacgagcag ggcaacccaa taagattgt tgaccgtttg    1320 agtgagcgcg tccaagaaaa cgcatcagga aatcgcaccg atattttgtc attcatccgc   1380
gaccgtggaa tcttcggaga cttggtcgat gctgaaccat tcaccaaggc atactccgag   1440
acactgtcct cccttcatga ccgtggcgcg gaagcaacca tcgatgcact tcttacgcag   1500
gtaactgtct aa                                                       1512
```

<210> SEQ ID NO 30
<211> LENGTH: 503
<212> TYPE: PRT
<213> ORGANISM: corynebacterium

<400> SEQUENCE: 30

```
Met Asn Thr Pro Leu Gln Leu Asn Thr Glu Asn Leu Gln Glu Ile Ala
1               5                   10                  15

Ser Thr Ser Gly Val Gln Ile Pro Ala Phe Asn Arg Ala Asp Val Ala
            20                  25                  30

Pro Gly Ile Val His Phe Gly Val Gly Gly Phe His Arg Ala His Gln
        35                  40                  45

Ala Met Tyr Leu Asn Glu Leu Met Asn Glu Gly Lys Ala Leu Asp Trp
    50                  55                  60

Gly Ile Ile Gly Met Gly Val Met Pro Ser Asp Val Arg Met Arg Asp
65                  70                  75                  80

Ala Leu Ala Ser Gln Asp His Leu Tyr Thr Leu Thr Lys Ala Pro
            85                  90                  95

Asp Gly Thr Leu Asp Gln Lys Ile Ile Gly Ser Ile Ile Asp Tyr Val
            100                 105                 110

Phe Ala Pro Glu Asp Pro Ala Arg Ala Val Ala Thr Leu Ala Gln Asp
        115                 120                 125

Ser Ile Arg Ile Val Ser Leu Thr Val Thr Glu Gly Gly Tyr Asn Ile
    130                 135                 140

Asp Pro Ala Thr Glu Asp Phe Asp His Thr Asn Pro Arg Ile Val Ala
145                 150                 155                 160
```

Asp Arg Glu Ala Leu Gln Ala Gly Asp Thr Ser Thr Leu Gln Thr Phe
            165                 170                 175

Phe Gly Leu Ile Thr Ala Ala Leu Ile Ser Arg Lys Glu Ser Gly Ser
        180                 185                 190

Thr Pro Phe Thr Ile Met Ser Cys Asp Asn Ile Gln Gly Asn Gly Asp
    195                 200                 205

Leu Ala Lys Arg Phe Phe Leu Ala Phe Ala His Ser Val Ser Ser Glu
210                 215                 220

Leu Gly Glu Trp Val Glu Asn Asn Val Ala Phe Pro Asn Ser Met Val
225                 230                 235                 240

Asp Arg Ile Thr Pro Glu Thr Thr Asp Gly Asp Arg Asp Asp Ile Lys
            245                 250                 255

Glu Ile Gly Tyr Ile Asp Ala Trp Pro Val Val Ser Glu Asp Phe Thr
        260                 265                 270

Gln Trp Val Leu Glu Asp Ala Phe Thr Gln Gly Arg Pro Ala Tyr Glu
    275                 280                 285

Glu Val Gly Val Gln Val Val Ser Asp Val Glu Pro Tyr Glu Leu Met
290                 295                 300

Lys Leu Arg Leu Leu Asn Ala Ser His Gln Gly Leu Cys Tyr Phe Gly
305                 310                 315                 320

His Leu Ala Gly His His Met Val His Asp Val Met Ala Asp Thr Arg
            325                 330                 335

Phe Gln Asp Phe Leu Leu Ala Tyr Met Glu Arg Glu Ala Thr Pro Thr
        340                 345                 350

Leu Lys Glu Leu Pro Gly Val Asp Leu Asp Ala Tyr Arg Arg Gln Leu
    355                 360                 365

Ile Ala Arg Phe Gly Asn Ala Ala Val Lys Asp Thr Val Pro Arg Leu
370                 375                 380

Cys Ala Glu Ser Ser Asp Arg Ile Pro Lys Trp Leu Leu Pro Val Val
385                 390                 395                 400

Arg Glu Asn Leu Ala Ala Gly Arg Asp Val Thr Leu Ser Ala Ala Ile
            405                 410                 415

Val Ala Ser Trp Ala Arg Tyr Ala Glu Gly Thr Asp Glu Gln Gly Asn
        420                 425                 430

Pro Ile Lys Ile Val Asp Arg Leu Ser Glu Arg Val Gln Glu Asn Ala
    435                 440                 445

Ser Gly Asn Arg Thr Asp Ile Leu Ser Phe Ile Arg Asp Arg Gly Ile
450                 455                 460

Phe Gly Asp Leu Val Asp Ala Glu Pro Phe Thr Lys Ala Tyr Ser Glu
465                 470                 475                 480

Thr Leu Ser Ser Leu His Asp Arg Gly Ala Glu Ala Thr Ile Asp Ala
            485                 490                 495

Leu Leu Thr Gln Val Thr Val
            500

<210> SEQ ID NO 31
<211> LENGTH: 53
<212> TYPE: DNA
<213> ORGANISM: Artificial Sequence
<220> FEATURE:
<223> OTHER INFORMATION: primer

<400> SEQUENCE: 31
gcaggtacca ggaggtaata aatatgaaac acggcatcta ttattcttac tgg        53

<210> SEQ ID NO 32
<211> LENGTH: 32
<212> TYPE: DNA
<213> ORGANISM: Artificial Sequence
<220> FEATURE:
<223> OTHER INFORMATION: primer

<400> SEQUENCE: 32
gctggatcct tagccaccaa gaacgaagcg gg                          32

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
ccacggaact tcggctgtt ttg                                     23

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
cttccgtagg tgccacaata tc                                     22

<210> SEQ ID NO 35
<211> LENGTH: 44
<212> TYPE: DNA
<213> ORGANISM: Artificial Sequence
<220> FEATURE:
<223> OTHER INFORMATION: primer

<400> SEQUENCE: 35
cgaggatcca ggaggtaata atatgaaaaa taaattcgga gttg             44

<210> SEQ ID NO 36
<211> LENGTH: 28
<212> TYPE: DNA
<213> ORGANISM: Artificial Sequence
<220> FEATURE:
<223> OTHER INFORMATION: primer

<400> SEQUENCE: 36
gtctagatta tatctcagca gcgatggc                               28

<210> SEQ ID NO 37
<211> LENGTH: 53
<212> TYPE: DNA
<213> ORGANISM: Artificial Sequence
<220> FEATURE:
<223> OTHER INFORMATION: primer

<400> SEQUENCE: 37
cggtaccagg aggtaataat atgaaatatg gtatttattt tgcttattgg acg   53

<210> SEQ ID NO 38
<211> LENGTH: 32
<212> TYPE: DNA
<213> ORGANISM: Artificial Sequence
<220> FEATURE:
<223> OTHER INFORMATION: primer -continued

```
<400> SEQUENCE: 38
ctctagatta gataccaaac acatgcctgc ag                                32

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
cggactatct gaacgaactg acgg                                         24

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
ctccataagc atcctcctca tcc                                          23

<210> SEQ ID NO 41
<211> LENGTH: 45
<212> TYPE: DNA
<213> ORGANISM: Artificial Sequence
<220> FEATURE:
<223> OTHER INFORMATION: primer

<400> SEQUENCE: 41
cgaggatcca ggaggtaata atatgaaaca tggtatctat tatgc                  45

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
gtctagatta cttccactcc agcatat                                      27

<210> SEQ ID NO 43
<211> LENGTH: 338
<212> TYPE: PRT
<213> ORGANISM: Leuconostoc pseudomesenteroides ATCC 12291

<400> SEQUENCE: 43

Met Glu Ala Leu Val Leu Thr Gly Thr Lys Lys Leu Glu Val Glu Asn
1               5                   10                  15

Ile Glu Gln Pro Glu Val Lys Pro Asn Glu Val Leu Ile His Thr Ala
            20                  25                  30

Phe Ala Gly Ile Cys Gly Thr Asp His Ala Leu Tyr Ala Gly Leu Pro
        35                  40                  45

Gly Ser Ala Asp Ala Val Pro Pro Ile Val Leu Gly His Glu Asn Ser
    50                  55                  60

Gly Val Val Ala Glu Ile Gly Ser Asp Val Thr Asn Val Ala Val Gly
65                  70                  75                  80

Asp Arg Val Thr Ile Asp Pro Asn Ile Tyr Cys Gly Gln Cys Lys Tyr
                85                  90                  95

Cys Arg Thr Ala Arg Pro Glu Leu Cys Glu Asn Leu Ser Ala Val Gly
```

```
            100                 105                 110
Val Thr Arg Asn Gly Gly Phe Glu Glu Tyr Phe Thr Ala Pro Ala Ser
            115                 120                 125

Val Val Tyr Gln Ile Pro Asp Asn Val Ser Leu Lys Ser Ala Ala Val
            130                 135                 140

Val Glu Pro Ile Ser Cys Ala Val His Gly Ile Gln Leu Leu Lys Val
145                 150                 155                 160

Thr Pro Tyr Gln Lys Ala Leu Val Ile Gly Asp Gly Phe Met Gly Glu
            165                 170                 175

Leu Phe Val Gln Ile Leu Gln Ala Tyr Gly Ile His Gln Val Asp Leu
            180                 185                 190

Ala Gly Ile Val Pro Glu Lys Leu Ala Met Asn Lys Glu Lys Phe Gly
            195                 200                 205

Val Lys Asn Thr Tyr Asn Thr Lys Asp Gly Asp Lys Ile Pro Glu Gly
            210                 215                 220

Thr Tyr Asp Val Val Glu Ala Val Gly Leu Pro Gln Thr Gln Glu
225                 230                 235                 240

Ala Ala Ile Glu Ala Ser Ala Arg Gly Ala Gln Val Leu Met Phe Gly
            245                 250                 255

Val Gly Gly Pro Asp Ala Lys Phe Gln Met Asn Thr Tyr Glu Val Phe
            260                 265                 270

Gln Lys Gln Leu Thr Ile Gln Gly Ser Phe Ile Asn Pro Asn Ala Phe
            275                 280                 285

Glu Asp Ser Leu Ala Leu Leu Ser Ser Gly Lys Leu Asp Val Glu Ser
            290                 295                 300

Leu Met Ser His Glu Leu Asp Tyr Gln Thr Val Asp Asp Phe Val Asn
305                 310                 315                 320

Gly Lys Leu Gly Val Val Ser Lys Ala Val Val Lys Val Gly Gly Glu
            325                 330                 335

Glu Ala

<210> SEQ ID NO 44
<211> LENGTH: 338
<212> TYPE: PRT
<213> ORGANISM: Leuconostoc mesenteroides

<400> SEQUENCE: 44

Met Glu Ala Leu Val Leu Thr Gly Thr Lys Lys Leu Glu Val Lys Asp
1               5                   10                  15

Ile Asp Arg Pro Lys Val Leu Pro Asn Glu Val Leu Ile His Thr Ala
            20                  25                  30

Phe Ala Gly Ile Cys Gly Thr Asp His Ala Leu Tyr Ala Gly Leu Pro
            35                  40                  45

Gly Ser Ala Asp Ala Val Pro Pro Ile Val Leu Gly His Glu Asn Ser
            50                  55                  60

Gly Val Val Ala Glu Val Gly Ser Ala Val Thr Asn Val Lys Val Gly
65                  70                  75                  80

Asp Arg Val Thr Val Asp Pro Asn Ile Tyr Cys Gly Gln Cys Lys Tyr
            85                  90                  95

Cys Arg Thr Ala Arg Pro Glu Leu Cys Glu Asn Leu Ser Ala Val Gly
            100                 105                 110

Val Thr Arg Asp Gly Gly Phe Glu Glu Phe Thr Ala Pro Ala Ser
            115                 120                 125

Val Val Tyr Pro Ile Pro Asp Asn Val Ser Leu Lys Ser Ala Ala Val
```

```
            130                 135                 140
Val Glu Pro Ile Ser Cys Ala Val His Gly Ile Gln Leu Leu Lys Val
145                 150                 155                 160

Thr Pro Tyr Gln Lys Ala Leu Val Ile Gly Asp Gly Phe Met Gly Glu
                165                 170                 175

Leu Phe Val Gln Ile Leu Gln Ala Tyr Gly Ile His Gln Val Asp Leu
                180                 185                 190

Ala Gly Ile Val Asp Glu Lys Leu Ala Met Asn Lys Glu Lys Phe Gly
                195                 200                 205

Val Lys Asn Thr Tyr Asn Thr Met Lys Gly Asp Lys Ile Pro Glu Gly
                210                 215                 220

Lys Tyr Asp Val Ile Ile Glu Ala Val Gly Leu Pro Gln Thr Gln Glu
225                 230                 235                 240

Ala Ala Ile Glu Ala Ser Ala Arg Gly Ala Gln Val Leu Met Phe Gly
                245                 250                 255

Val Gly Gly Pro Asp Ala Lys Phe Gln Met Asn Thr Tyr Glu Val Phe
                260                 265                 270

Gln Lys Gln Leu Thr Ile Gln Gly Ser Phe Ile Asn Pro Asn Ala Phe
                275                 280                 285

Glu Asp Ser Leu Ala Leu Leu Ser Ser Gly Lys Leu Asn Val Glu Ala
                290                 295                 300

Leu Met Ser His Glu Leu Asp Tyr Lys Thr Val Asp Asp Phe Val Asn
305                 310                 315                 320

Gly Lys Leu Gly Val Val Ser Lys Ala Val Lys Val Gly Gly Glu
                325                 330                 335

Glu Ala

<210> SEQ ID NO 45
<211> LENGTH: 477
<212> TYPE: PRT
<213> ORGANISM: Rhodobacter sphaeroides

<400> SEQUENCE: 45

Met Thr Arg Ser Val Thr Arg Pro Ser Tyr Asp Arg Lys Ala Leu Thr
1               5                   10                  15

Pro Gly Ile Val His Ile Gly Val Gly Asn Phe His Arg Ala His Gln
                20                  25                  30

Ala Val Tyr Leu Asp Asp Leu Phe Ala Leu Gly Glu Gly His Asp Trp
                35                  40                  45

Ala Ile Leu Gly Ala Gly Val Arg Pro Thr Asp Ala Arg Met Arg Glu
50                  55                  60

Ala Leu Ala Ala Gln Asp Asn Leu Ser Thr Val Ile Glu Leu Asp Pro
65                  70                  75                  80

Ala Gly His Arg Ala Arg Gln Val Gly Ala Met Val Gly Phe Leu Pro
                85                  90                  95

Val Glu Ala Asp Asn Ala Ala Leu Ile Glu Ala Met Ser Asp Pro Arg
                100                 105                 110

Ile Arg Ile Val Ser Leu Thr Val Thr Glu Gly Gly Tyr Tyr Val Asp
                115                 120                 125

Ala Ser Gly Ala Phe Asp Pro Thr His Pro Asp Ile Val Ala Asp Ala
                130                 135                 140

Ala His Pro Ala Arg Pro Ala Thr Ala Phe Gly Ala Ile Leu Ala Ala
145                 150                 155                 160

Leu Arg Ala Arg Arg Asp Ala Gly Val Thr Pro Phe Thr Val Met Ser
```

-continued

```
                165                 170                 175
    Cys Asp Asn Leu Pro Gly Asn Gly His Val Thr Arg Asn Ala Val
                    180                 185                 190
    Gly Leu Ala Glu Leu Tyr Asp Ala Glu Leu Ala Gly Trp Val Lys Ala
                    195                 200                 205
    Gln Val Ala Phe Pro Asn Gly Met Val Asp Arg Ile Thr Pro Ala Thr
                210                 215                 220
    Gly Pro His Glu Arg Glu Leu Ala Gln Gly Phe Gly Leu Ala Asp Pro
    225                 230                 235                 240
    Val Pro Val Thr Cys Glu Pro Phe Arg Gln Trp Val Ile Glu Asp His
                    245                 250                 255
    Phe Pro Ala Gly Arg Pro Ala Leu Glu Lys Val Gly Val Thr Phe Thr
                    260                 265                 270
    Pro His Val His Ala Tyr Glu Ala Met Lys Ile Arg Ile Leu Asn Gly
                    275                 280                 285
    Gly His Ala Val Ile Ala Tyr Pro Ser Ala Leu Met Asp Ile Gln Leu
                    290                 295                 300
    Val His Ala Ala Met Ala His Pro Leu Ile Ala Ala Phe Leu His Lys
    305                 310                 315                 320
    Val Glu Val Glu Glu Ile Leu Pro His Val Pro Pro Val Pro Asp Thr
                    325                 330                 335
    Ser Ile Pro Asp Tyr Leu Thr Leu Ile Glu Ser Arg Phe Ser Asn Pro
                    340                 345                 350
    Glu Ile Ala Asp Thr Thr Arg Arg Leu Cys Leu Asp Gly Ser Asn Arg
                    355                 360                 365
    Gln Pro Lys Phe Ile Val Pro Ser Leu Arg Asp Asn Leu Ala Ala Gly
                    370                 375                 380
    Thr Val Pro Lys Gly Leu Val Leu Ser Ala Leu Trp Cys Arg Tyr
    385                 390                 395                 400
    Cys Phe Gly Thr Thr Asp Ser Gly Val Val Glu Pro Asn Asp Pro
                    405                 410                 415
    Asn Trp Thr Ala Leu Gln Asp Arg Ala Arg Arg Ala Lys Glu Thr Pro
                    420                 425                 430
    Ala Glu Trp Leu Ala Met Thr Glu Val Tyr Gly Asp Leu Ala Gln Asn
                    435                 440                 445
    Asp Leu Leu Ala Ala Glu Phe Ala Ala Ala Leu Glu Ala Val Trp Arg
                    450                 455                 460
    Asp Gly Ala Glu Ala Val Leu Arg Arg Phe Leu Ala Ala
    465                 470                 475

<210> SEQ ID NO 46
<211> LENGTH: 493
<212> TYPE: PRT
<213> ORGANISM: Pseudomonas fluorescens DSM 50106

<400> SEQUENCE: 46

Met Lys Leu Asn Lys Gln Asn Leu Thr Gln Leu Ala Pro Glu Val Lys
1               5                   10                  15

Leu Pro Ala Tyr Thr Leu Ala Asp Thr Arg Gln Gly Ile Ala His Ile
                20                  25                  30

Gly Val Gly Gly Phe His Arg Ala His Gln Ala Tyr Tyr Thr Asp Ala
            35                  40                  45

Leu Met Asn Thr Gly Glu Gly Leu Asp Trp Ser Ile Cys Gly Val Gly
        50                  55                  60
```

```
Leu Arg Ser Glu Asp Arg Lys Ala Arg Asp Asp Leu Ala Gly Gln Asp
 65                  70                  75                  80

Tyr Leu Phe Thr Leu Tyr Glu Leu Gly Asp Thr Asp Thr Glu Val
             85                  90                  95

Arg Val Ile Gly Ser Ile Ser Asp Met Leu Leu Ala Glu Asp Ser Ala
                100                 105                 110

Gln Ala Leu Ile Asp Lys Leu Ala Ser Pro Glu Ile Arg Ile Val Ser
            115                 120                 125

Leu Thr Ile Thr Glu Gly Gly Tyr Cys Ile Asp Asp Ser Asn Gly Glu
        130                 135                 140

Phe Met Ala His Leu Pro Gln Ile Gln His Asp Leu Ala His Pro Ser
145                 150                 155                 160

Ser Pro Lys Thr Val Phe Gly Phe Ile Cys Ala Ala Leu Thr Gln Arg
                165                 170                 175

Arg Ala Ala Gly Ile Pro Ala Phe Thr Val Met Ser Cys Asp Asn Leu
            180                 185                 190

Pro His Asn Gly Ala Val Thr Arg Lys Ala Leu Leu Ala Phe Ala Ala
        195                 200                 205

Leu His Asn Ala Glu Leu His Asp Trp Ile Lys Ala His Val Ser Phe
210                 215                 220

Pro Asn Ala Met Val Asp Arg Ile Thr Pro Met Thr Ser Thr Ala His
225                 230                 235                 240

Arg Leu Gln Leu His Asp Glu His Gly Ile Asp Asp Ala Trp Pro Val
                245                 250                 255

Val Cys Glu Pro Phe Val Gln Trp Val Leu Glu Asp Lys Phe Val Asn
            260                 265                 270

Gly Arg Pro Ala Trp Glu Lys Val Gly Val Gln Phe Thr Asp Asp Val
        275                 280                 285

Thr Pro Tyr Glu Glu Met Lys Ile Gly Leu Leu Asn Gly Ser His Leu
        290                 295                 300

Ala Leu Thr Tyr Leu Gly Phe Leu Lys Gly Tyr Arg Phe Val His Glu
305                 310                 315                 320

Thr Met Asn Asp Pro Leu Phe Val Ala Tyr Met Arg Ala Tyr Met Asp
                325                 330                 335

Leu Asp Val Thr Pro Asn Leu Ala Pro Val Pro Gly Ile Asp Leu Thr
            340                 345                 350

Asp Tyr Lys Gln Thr Leu Val Asp Arg Phe Ser Asn Gln Ala Ile Ala
        355                 360                 365

Asp Gln Leu Glu Arg Val Cys Ser Asp Gly Ser Ser Lys Phe Pro Lys
370                 375                 380

Phe Thr Val Pro Thr Ile Asn Arg Leu Ile Ala Asp Gly Arg Glu Thr
385                 390                 395                 400

Glu Arg Ala Ala Leu Val Val Ala Ala Trp Ala Leu Tyr Leu Lys Gly
                405                 410                 415

Val Asp Glu Asn Gly Val Ser Tyr Thr Ile Pro Asp Pro Arg Ala Glu
            420                 425                 430

Phe Cys Gln Gly Leu Val Ser Asp Ala Leu Ile Ser Gln Arg Leu
        435                 440                 445

Leu Ala Val Glu Glu Ile Phe Gly Thr Ala Ile Pro Asn Ser Pro Glu
450                 455                 460

Phe Val Ala Ala Phe Glu Arg Cys Tyr Gly Ser Leu Arg Asp Asn Gly
465                 470                 475                 480

Val Thr Thr Thr Leu Lys His Leu Leu Lys Lys Pro Val
```

<210> SEQ ID NO 47
<211> LENGTH: 45
<212> TYPE: DNA
<213> ORGANISM: Artificial Sequence
<220> FEATURE:
<223> OTHER INFORMATION: forward primer

<400> SEQUENCE: 47
gcggtaccag gaggaggtag atatggaagc acttgtgtta actgg    45

<210> SEQ ID NO 48
<211> LENGTH: 31
<212> TYPE: DNA
<213> ORGANISM: Artificial Sequence
<220> FEATURE:
<223> OTHER INFORMATION: reverse primer

<400> SEQUENCE: 48
gctggatcct tatgcctctt cgccaccaac c    31

<210> SEQ ID NO 49
<211> LENGTH: 401
<212> TYPE: PRT
<213> ORGANISM: Mycobacterium vaccae N10

<400> SEQUENCE: 49

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240
```

```
Thr Arg Glu Asp Met Tyr Pro Val Cys Asp Val Val Thr Leu Asn Cys
                245                 250                 255

Pro Leu His Pro Glu Thr Glu His Met Ile Asn Asp Gly Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val

<210> SEQ ID NO 50
<211> LENGTH: 473
<212> TYPE: PRT
<213> ORGANISM: Zymomonas mobilis subsp. mobilis ZM4

<400> SEQUENCE: 50

Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
            20                  25                  30

Ala Ile Gly Thr Pro Val Asp Ile His Phe Ile Ala Pro Arg His Leu
        35                  40                  45

Ser Ala Thr Ala Ala Ala Ser Leu Ser Gly Met Val Val Ala Val
    50                  55                  60

Leu Val Gly Cys Val Thr Gly Ser Leu Leu Ser Gly Trp Ile Gly Ile
65                  70                  75                  80

Arg Phe Gly Arg Arg Gly Gly Leu Leu Met Ser Ser Ile Cys Phe Val
                85                  90                  95

Ala Ala Gly Phe Gly Ala Ala Leu Thr Glu Lys Leu Phe Gly Thr Gly
            100                 105                 110

Gly Ser Ala Leu Gln Ile Phe Cys Phe Phe Arg Phe Leu Ala Gly Leu
        115                 120                 125

Gly Ile Gly Val Val Ser Thr Leu Thr Pro Thr Tyr Ile Ala Glu Ile
    130                 135                 140

Arg Pro Pro Asp Lys Arg Gly Gln Met Val Ser Gly Gln Gln Met Ala
145                 150                 155                 160

Ile Val Thr Gly Ala Leu Thr Gly Tyr Ile Phe Thr Trp Leu Leu Ala
                165                 170                 175

His Phe Gly Ser Ile Asp Trp Val Asn Ala Ser Gly Trp Cys Trp Ser
            180                 185                 190

Pro Ala Ser Glu Gly Leu Ile Gly Ile Ala Phe Leu Leu Leu Leu Leu
        195                 200                 205
```

-continued

```
Thr Ala Pro Asp Thr Pro His Trp Leu Val Met Lys Gly Arg His Ser
    210                 215                 220
Glu Ala Ser Lys Ile Leu Ala Arg Leu Glu Pro Gln Ala Asp Pro Asn
225                 230                 235                 240
Leu Thr Ile Gln Lys Ile Lys Ala Gly Phe Asp Lys Ala Met Asp Lys
                245                 250                 255
Ser Ser Ala Gly Leu Phe Ala Phe Gly Ile Thr Val Val Phe Ala Gly
            260                 265                 270
Val Ser Val Ala Ala Phe Gln Gln Leu Val Gly Ile Asn Ala Val Leu
    275                 280                 285
Tyr Tyr Ala Pro Gln Met Phe Gln Asn Leu Gly Phe Gly Ala Asp Thr
290                 295                 300
Ala Leu Leu Gln Thr Ile Ser Ile Gly Val Val Asn Phe Ile Phe Thr
305                 310                 315                 320
Met Ile Ala Ser Arg Val Val Asp Arg Phe Gly Arg Lys Pro Leu Leu
                325                 330                 335
Ile Trp Gly Ala Leu Gly Met Ala Ala Met Met Ala Val Leu Gly Cys
            340                 345                 350
Cys Phe Trp Phe Lys Val Gly Gly Val Leu Pro Leu Ala Ser Val Leu
    355                 360                 365
Leu Tyr Ile Ala Val Phe Gly Met Ser Trp Gly Pro Val Cys Trp Val
370                 375                 380
Val Leu Ser Glu Met Phe Pro Ser Ser Ile Lys Gly Ala Ala Met Pro
385                 390                 395                 400
Ile Ala Val Thr Gly Gln Trp Leu Ala Asn Ile Leu Val Asn Phe Leu
                405                 410                 415
Phe Lys Val Ala Asp Gly Ser Pro Ala Leu Asn Gln Thr Phe Asn His
            420                 425                 430
Gly Phe Ser Tyr Leu Val Phe Ala Ala Leu Ser Ile Leu Gly Gly Leu
    435                 440                 445
Ile Val Ala Arg Phe Val Pro Glu Thr Lys Gly Arg Ser Leu Asp Glu
    450                 455                 460
Ile Glu Glu Met Trp Arg Ser Gln Lys
465                 470

<210> SEQ ID NO 51
<211> LENGTH: 45
<212> TYPE: DNA
<213> ORGANISM: Artificial Sequence
<220> FEATURE:
<223> OTHER INFORMATION: forward primer

<400> SEQUENCE: 51
cgaggatcca ggaggtaata atatgagttc tgaaagtagt caggg            45

<210> SEQ ID NO 52
<211> LENGTH: 29
<212> TYPE: DNA
<213> ORGANISM: Artificial Sequence
<220> FEATURE:
<223> OTHER INFORMATION: reverse primer

<400> SEQUENCE: 52
gtctagatta cttctgggag cgccacatc                              29

<210> SEQ ID NO 53
<211> LENGTH: 269
<212> TYPE: PRT
```

```
<213> ORGANISM: Artificial Sequence
<220> FEATURE:
<223> OTHER INFORMATION: Consensus among SEQ ID NOS: 3, 4, 9 and 10

<400> SEQUENCE: 53

Met Lys His Gly Ile Tyr Tyr Ala Tyr Trp Thr Glu Trp Ser Ala Lys
1               5                   10                  15

Tyr Lys Lys Tyr Ile Glu Lys Val Ala Lys Leu Gly Phe Asp Ile Ile
            20                  25                  30

Glu Ile Ala Ala Ala Leu Glu Tyr Ser Asp Asp Leu Glu Leu Lys Lys
        35                  40                  45

Ala Lys Asp Asn Gly Ile Ile Leu Thr Ala Gly Tyr Gly Pro Thr Lys
    50                  55                  60

Asn Leu Ser Glu Asp Ala Glu Val Arg Ala Ala Leu Phe Phe Lys
65                  70                  75                  80

Arg Leu Leu Asp Ile Leu Ala Glu Leu Asp Ile His Ile Ile Gly Gly
                85                  90                  95

Ala Leu Tyr Ser Tyr Trp Pro Val Asp Phe Ser Asn Asp Lys Gly Asp
                100                 105                 110

Trp Ala Trp Gly Val Glu Gly Met Arg Glu Leu Ala Asp Phe Ala Asp
            115                 120                 125

Asp Ile Asn Leu Gly Met Glu Val Leu Asn Arg Phe Glu Ser His Ile
        130                 135                 140

Leu Asn Thr Ala Glu Glu Ala Val Ala Phe Val Lys Asp Val Gly Ser
145                 150                 155                 160

Asn Val Lys Val Met Leu Asp Thr Phe His Met Asn Ile Glu Glu Ser
                165                 170                 175

Phe Ala Gly Ala Ile Arg Thr Ala Gly Asp Leu Leu Gly His Phe His
                180                 185                 190

Thr Gly Glu Asn Asn Arg Leu Val Pro Gly Lys Gly Arg Ile Pro Trp
            195                 200                 205

Lys Glu Ile Gly Asn Ala Leu Arg Asp Ile Asn Tyr Asp Gly Ala Ala
            210                 215                 220

Val Met Glu Pro Phe Val Lys Ser Gly Gly Thr Ile Gly Ser Asp Ile
225                 230                 235                 240

Lys Val Trp Arg Asp Leu Ser Gly Ala Asp Glu Ala Ala Leu Asp Asp
                245                 250                 255

Asp Ala Arg Ala Leu Glu Phe Ala Arg His Val Leu Gly
                260                 265
```

US 10,266,862 B2

METHOD FOR PREPARING PSICOSE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/011954, filed on Nov. 6, 2015, which claims priority to the benefit of Korean Patent Application No. 10-2014-0153949 filed on Nov. 6, 2014 and 10-2015-0156115 filed on Nov. 6, 2015 in the Korean Intellectual Property Office, the entire contents of which are incorporated herein by reference.

TECHNICAL FIELD

The present invention relates to a method for preparing psicose at a high purity.

BACKGROUND ART

Psicose (D-psicose) is an epimer of the third carbon of fructose (D-fructose), and a functional saccharide which has sweetness like common saccharides but has almost zero calorie since it is not metabolized in the human body, and is thus able to be used as a functional sweetener which can replace sucrose for diabetic and obese patients. In addition, psicose serves to reduce abdominal obesity by controlling enzyme activity involved in lipid synthesis in the liver, and is currently being studied as therapeutic agents for diabetes and arteriosclerosis.

As such, psicose has attracted attention as a sweetener, and in a food industry field, a need for developing a method for efficiently producing psicose gradually arises. Since a small quantity of psicose is present in natural substances during molasses treatment or glucose isomerization, conventional psicose production has been generally carried out through a chemical process. Bilik et al. developed a technique for producing psicose from fructose by utilizing catalysis of molybdic acid ions. McDonald produced psicose in a three-step chemical treatment process from 1,2:4,5-di-o-isopropylidene-beta-D-fructopyranose. In addition, Doner produced psicose by a method of heating fructose with ethanol and triethylamine. However, the psicose production by such a chemical method requires high costs, but has low production efficiency and large quantities of by products.

According to a method for producing psicose by a biological method, Ken Izumori et al. suggested that psicose can be produced from galacitol, D-tagatose or D-talitol by utilizing microbial cell responses. However, these substrates are also relatively rare sucroses or sucrose alcohols present in nature, and thus prime costs thereof are high.

As an enzyme conversion method, there is a method for enzymatically converting fructose into psicose by producing D-tagatose-3-epimerase of a separated microorganism, for example, *Pseudomonas cichorii* ST-24, in recombinant *E. coli* and purifying the enzyme, and Ken Izumori et al. has produced psicose at a conversion ratio of approximately 25% using a reaction system for immobilizing D-tagatose-3-epimerase.

According to such a conventional art, to produce psicose from fructose, studies have been conducted to increase psicose productivity by purifying an enzyme and immobilizing the purified enzyme. It is true that the process for purifying an enzyme have needed much time and cost.

Meanwhile, even when piscose is produced, due to similar physical properties to fructose, it is difficult to separate psicose from fructose.

Therefore, there is a demand for a method for producing psicose, which has a high efficiency and can easily isolates psicose.

SUMMURY

The present invention is directed to providing a method for producing psicose, which can isolate psicose at a high purity.

The present invention is also directed to providing a method for preparing psicose, which is improved in production capacity of psicose.

In one aspect, the present invention provides a method for preparing psicose, which includes adding a mannitol dehydrogenase to a mixture of fructose and psicose to convert the fructose into mannitol; and isolating the mannitol from the mixture.

Representative methods for preparing psicose may include a chemical method for converting fructose into psicose using a catalyst, and a biological method for converting fructose into psicose by introducing a gene encoding an enzyme that catalyzes the conversion of fructose into psicose into a microorganism.

These methods have the use of fructose as a substrate in common, and have difficulty in isolating psicose from a reaction mixture because fructose has similar physical properties to psicose.

However, the inventors completed the present invention based on the ideas in which a mixture of fructose and psicose reacts with mannitol dehydrogenase to convert the fructose into mannitol and isolate the psicose from the mannitol, thereby more easily isolating the psicose with high efficiency.

Hereinafter, the present invention will be described in detail.

According to an exemplary embodiment of the present invention, first, a mannitol dehydrogenase is added to a mixture of fructose and psicose to convert the fructose into mannitol.

The mixture of fructose and psicose is a mixture of psicose, which has been obtained by the conversion from fructose by a chemical or biological method, and unconverted fructose.

Therefore, the present invention may further include preparing the mixture of fructose and psicose by a reaction between fructose as a substrate and an epimerase thereof.

The epimerase may be psicose-3-epimerase, and specifically, an *Agrobacterium tumefaciens*-derived psicose-3-epimerase or *Anaerostipes caccae*-derived psicose-3-epimerase.

A gene encoding the epimerase may be a gene encoding an *Agrobacterium tumefaciens*-derived psicose-3-epimerase of SEQ ID NO: 1, or a gene encoding an *Anaerostipes caccae*-derived psicose-3-epimerase of SEQ ID NO: 2.

The *Agrobacterium tumefaciens*-derived psicose-3-epimerase may have an amino acid sequence of SEQ ID NO: 3, and the *Anaerostipes caccae*-derived psicose-3-epimerase may have an amino acid sequence of SEQ ID NO: 4.

Preferably, the gene encoding the epimerase may be a gene encoding an amino acid sequence of a psicose-3-epimerase of SEQ ID NO: 5 since the epimerase has a more excellent high temperature stability.

The amino acid sequence of SEQ ID NO: 5 is a sequence in which the amino acid at position 33 is substituted with leucine, and the amino acid at position 213 is substituted with cysteine in an amino acid sequence of the *Agrobacterium tumefaciens*-derived psicose-3-epimerase, and has excellent thermal stability.

The inventors confirmed that a *Clostridium*-derived psicose-3-epimerase has excellent thermal stability, and referring to FIG. 7, it was confirmed that the *Clostridium*-derived psicose-3-epimerase having high thermal stability has a sequence corresponding to one or both of the above-mentioned substitutions.

Therefore, it was confirmed that as well as the *Agrobacterium tumefaciens*-derived psicose-3-epimerase, even for psicose-3-epimerases derived from other strains, an amino acid sequence corresponding to the amino acids nos. 33 and 213 of the amino acid sequence of the *Agrobacterium tumefaciens*-derived psicose-3-epimerase is a significant sequence for enhancing thermal stability.

A specific example of such an amino acid sequence may be a sequence in which the amino acid at position 32 is substituted with leucine, or the amino acid at position 196 is substituted with cysteine in an amino acid sequence of SEQ ID NO: 6. SEQ ID NO: 6 represents a sequence shown in the box of FIG. 7, and a common base sequence between *Agrobacterium tumefaciens*-, *Anaerostipes caccae*-, *Clostridium bolteae*-, *Clostridium hylemonae*-derived psicose-3-epimerase amino acid sequences (SEQ ID NOs: 3, 4, 9, and 10) used in the present invention. Accordingly, the microorganism may be substituted with a gene encoding the amino acid sequence, but the present invention is not limited thereto.

In addition, likewise, in terms of excellent high temperature stability and psicose production capacity, the epimerase may be a *Clostridium*-derived psicose-3-epimerase, and a gene encoding the epimerase may be a gene encoding the *Clostridium bolteae*-derived psicose-3-epimerase of SEQ ID NO: 7, or a gene encoding the *Clostridium hylemonae*-derived psicose-3-epimerase of SEQ ID NO: 8. To maximize the high temperature stability, the gene is preferably a gene encoding the *Clostridium hylemonae*-derived psicose-3-epimerase of SEQ ID NO: 8.

The *Clostridium bolteae*-derived psicose-3-epimerase may have an amino acid sequence of SEQ ID NO: 9, and the *Clostridium hylemonae*-derived psicose-3-epimerase may have an amino acid sequence of SEQ ID NO: 10.

Among the above-described psicose-3-epimerases, in the *Anaerostipes caccae*-derived psicose-3-epimerase, the psicose-3-epimerase having a sequence in which the amino acid at position 32 is substituted with leucine, or the amino acid at position 196 is substituted with cysteine in the amino acid sequence of SEQ ID NO: 6, the *Clostridium bolteae*-derived psicose-3-epimerase and the *Clostridium hylemonae*-derived psicose-3-epimerase, a pH exhibiting the optimal activity is low as 7 or less.

A reaction between the fructose and the epimerase may be performed at 20 to 90° C., and to maximize psicose production capacity, preferably 40 to 90° C. Specifically, the reaction may be performed at, for example, 40 to 50° C., 40 to 60° C., 40 to 70° C., 40 to 80° C., 40 to 90° C., 45 to 60° C., 45 to 70° C., 45 to 80° C., 45 to 90° C., 50 to 70° C., 50 to 80° C., 50 to 90° C., 55 to 60° C., 55 to 70° C., 55 to 80° C., 55 to 90° C., 60 to 70° C., 60 to 80° C., 60 to 90° C., 70 to 80° C., 70 to 90° C., 75 to 80° C., 75 to 90° C., or 80 to 90° C. When the reaction temperature exceeds more than 90° C., the epimerase or a microorganism to be described later may be thermally damaged or denatured.

When the reaction is performed at 40° C. or higher, the epimerase may be thermally damaged or denatured, and therefore the reaction is preferably performed in a microorganism. As the reaction temperature increases, the psicose production capacity further increases, and therefore, the reaction might be difficult to be realized due to thermal denaturation of the epimerase. However, in the reaction performed in a microorganism, since the epimerase is protected by the microorganism, the reaction can be carried out at a high temperature.

The term "microorganism" used herein may be a cell that can be cultured in a liquid medium.

The microorganism may express the epimerase endogenously or by transformation. In this case, the epimerase is generated in the microorganism, and therefore the production of psicose may be continuously performed by the reaction between the fructose and the epimerase in the microorganism.

When the microorganism is transformed with a gene encoding an epimerase and expresses the epimerase, the gene encoding the epimerase may be a gene encoding the *Agrobacterium tumefaciens*-derived psicose-3-epimerase of SEQ ID NO: 1, or a gene encoding the *Anaerostipes caccae*-derived psicose-3-epimerase of SEQ ID NO: 2.

Since the epimerase has more excellent high temperature stability, the gene encoding the epimerase is preferably a gene encoding an amino acid sequence of a psicose-3-epimerase of SEQ ID NO: 5.

In addition, likewise, in terms of excellent high temperature stability and psicose production capacity, the gene encoding the epimerase may be the gene encoding the *Clostridium bolteae*-derived psicose-3-epimerase of SEQ ID NO: 7, or the gene encoding the *Clostridium hylemonae*-derived psicose-3-epimerase of SEQ ID NO: 8.

The microorganism may be a prokaryotic or eukaryotic cell, which can be cultured in a liquid medium, and can be cultured at a high temperature as exemplified above. The microorganism may be, for example, a bacterium, fungus, or a combination thereof. Bacteria may be Gram-positive bacteria, Gram-negative bacteria, or a combination thereof, and to increase psicose production capacity, bacteria may be Gram-positive bacteria. Gram-negative bacteria may include the genus *Escherichia*. Gram-positive bacteria may be the genus *Bascillus*, the genus *Corynebacterium*, the genus *Actinomyces*, the genus *Lactobacillus* or a combination thereof. Fungi may be yeast, the genus *Kluyveromyces* or a combination thereof.

In the method for producing psicose of the present invention, when the reaction between the fructose and the epimerase is performed at 40° C. or higher, the microorganism may be a thermophile with high thermal stability. For example, the microorganism is preferably the genus *Corynebacterium* or *Actinomyces*, and more preferably *Corynebacterium glutamicum*, and most preferably *Corynebacterium glutamicum* ATCC 13032 into which the above-described epimerase-coding gene is introduced.

A microorganism in the genus *Escherichia* may be *E. coli*, and specifically, the gene encoding the epimerase may be introduced into DH5a, MG1655, BL21 (DE), S17-1, XL1-Blue, BW25113 or a combination thereof.

In addition, in the *E. coli*, one region comprising a gene encoding an endogenous 6-phosphofructokinase and an allose metabolic operon may be inactivated.

The gene encoding the 6-phosphofructokinase may have, for example, a nucleotide sequence of SEQ ID NO: 11, and the 6-phosphofructokinase may have an amino acid sequence of SEQ ID NO: 12.

Genes constituting the allose metabolic operon are rpiB, alsR, alsB, alsA, alsC, alsE and alsK, and one or more of these genes may be inactivated.

The rpiB, alsR, alsB, alsA, alsC, alsE and alsK genes may have, for example, nucleotide sequences of SEQ ID NOs: 13, 14, 15, 16, 17, 18 and 19, respectively.

The rpiB, alsR, alsB, alsA, alsC, alsE and alsK genes may encode amino acid sequences of SEQ ID NOs: 20, 21, 22, 23, 24, 25 and 26, respectively.

The term "inactivation" means that the gene expression is reduced or does not occur. The "inactivation" may be performed by a method known in the art. For example, the gene may be inactivated by homologous recombination. The homologous recombination may be mediated by, for example, transposon mutagenesis or P1 transduction.

A microorganism in the genus *Corynebacterium* may be *Corynebacterium glutamicum*, and is specifically *Corynebacterium glutamicum* ATCC 13032 into which the gene encoding the epimerase is introduced.

In the microorganism of the genus *Corynebacterium*, a gene of ptsF ($EII^{Fru}$, fruA, NCgl1861, GI: 19553141, EC 2.7.1.69), which is a PTS transport system for converting endogenous D-fructose into D-fructose 1-phosphate and transporting it to bacterial cells, may be deleted or inactivated.

The ptsF gene may have a nucleotide sequence of SEQ ID NO: 27, and encode an amino acid sequence of SEQ ID NO: 28.

Since psicose is generated from D-fructose, phosphorylation of the fructose may be inhibited by deleting or inactivating the gene, and therefore production efficiency of the psicose may be considerably improved.

Alternatively, in the microorganism of the genus *Corynebacterium*, an mtlD (NCgl0108, GI: 19551360, EC 1.1.1.67) gene encoding mannitol 2-dehydrogenase may be deleted or inactivated.

The mtlD gene may have a nucleotide sequence of SEQ ID NO: 29, and encode an amino acid sequence of SEQ ID NO: 30.

When the reaction between the fructose and the epimerase is performed in a microorganism, the microorganism may be cultured in a medium containing fructose.

The medium may be a nutrition medium containing a yeast extract and a nitrogen source, such as a 2YT medium, an LB medium or a TB medium.

A fructose concentration in the medium is not particularly limited, but may be in a range from, for example, 1% (w/v) to 80% (w/v). In the above range, the concentration range may be, for example, 1% (w/v) to 35% (w/v), 10% (w/v) to 80% (w/v), 20% (w/v) to 80% (w/v), 30% (w/v) to 80% (w/v), 40% (w/v) to 80% (w/v) or the like. The concentration range is preferably 1% (w/v) to 50% (w/v).

Alternatively, the medium may be a defined medium conventionally used in a saccharide field, which contains a carbon source such as glucose, glycerol, or the like; a nitrogen source such as ammonia, urea or the like; an essential metal ion such as sodium, potassium, calcium, magnesium, manganese, cobalt, or the like; a vitamin, etc.

The culture may be continuous, semi-continuous or batch culture.

The microorganism may be seeded in a fructose-containing medium at a cell turbidity (the value of absorbance at 600 nm, hereinafter, referred to as $OD_{600}$) of 0.01 to 300, for example, 1 to 300, 10 to 300, 20 to 300, 5 to 300, or 40 to 300. By using such microbial cells containing the enzyme at a high concentration, the fructose may be efficiently converted into psicose in a medium containing fructose at a high concentration among various media.

The culture may be performed by further adding a substance inducing the expression of an epimerase-coding gene.

The substance inducing gene expression may be, but is not particularly limited to, a substance conventionally used in the art.

In the method for producing psicose of the present invention, the production of psicose may be performed in a medium only containing fructose as a substrate and an inorganic salt for providing a cofactor. The reaction may be performed in a medium only containing fructose as a substrate and an inorganic salt for providing a cofactor. The inorganic salt may be, for example, a manganese salt or a cobalt salt. To exhibit a more improved psicose production rate, the inorganic salt may be a cobalt salt, and to safely use the produced psicose as food, the inorganic salt may be a manganese salt.

The medium containing only fructose and an inorganic salt may be a liquid medium in which fructose and an inorganic salt are dissolved in a solvent. The solvent may be, for example, water.

In the production of psicose using microorganisms, since metabolites such as an organic acid or the like of the microorganisms as well as psicose are generated in the medium, the medium may be gradually acidified. Since the medium containing only fructose and an inorganic salt according to the present invention does not contain a buffer solution, in this case, it is preferable to use a psicose-3-epimerase with a low pH exhibiting the optimal activity (e.g., pH 7 or less).

The method for producing psicose of the present invention may further include culturing the microorganisms in a fructose-free medium before the reaction between the fructose and the epimerase so as to induce the microorganisms to have resting cells.

The induction to have resting cells may be performed by culturing the microorganisms in a fructose-free medium until a stationary phase.

In the specification, the resting cells refer to cultured cells which are not grown any more. In the specification, the stationary phase refers to a phase in cell culture in which, after the exponential phase, cell division and proliferation stop and thus cell counts no longer increase, and therefore the synthesis and degradation of cell components are in equilibrium.

Therefore, the resting cells according to the present invention refer to cells in which the expression of an epimerase is sufficiently performed therein after the cell growth stops. When microorganisms are induced to have the resting cells, the epimerase expression reaches the highest level, and thus the psicose production may be maximized.

The fructose-free medium may be a medium which is the same as that containing fructose described above, except fructose is not contained.

In addition, the present invention may further include recovering the microorganisms after the reaction between the fructose and the epimerase thereof to be reused in conversion of a different substrate into psicose.

In the present invention, since the reaction between the fructose and the epimerase thereof is performed in microorganisms, even when the microorganisms are exposed to a high temperature, the epimerase still exhibits enzyme activity because it is protected by the microorganisms, and therefore the microorganisms can be reused.

That is, after the reaction, the microorganisms are recovered to be reused in the conversion of another substrate into psicose.

When the reaction is performed in an environment in which the growth of the separated microorganisms is maintained, the reuse number is not limited, and may be over several hundred to thousand times.

When the method further includes reusing the microorganisms, since the microorganisms are exposed to a high temperature multiple times, the use of thermophiles having high thermal stability is preferable to increase enzyme activity in reuse.

Among the above examples, the above-described epimerase-coding gene may be introduced into, preferably, the genus *Corynebacterium* or *Actinomyces*, more preferably, *Corynebacterium glutamicum*, and most preferably, *Corynebacterium glutamicum* ATCC 13032.

In the present invention, the mixture of fructose and psicose reacts with mannitol dehydrogenase to convert fructose that does not react with an epimerase into mannitol.

When the conversion of fructose into psicose is performed in microorganisms, the reaction mixture may be a supernatant obtained by isolating the mixture of fructose and psicose from the microorganisms.

The mannitol dehydrogenase may be mannitol-2-dehydrogenase. Specifically, *Leuconostoc pseudomesenteroides* ATCC 12291-derived mannitol-2-dehydrogenase (GenBank: CAD31644.1, GI: 28865823), *Leuconostoc mesenteroides*-derived mannitol-2-dehydrogenase (GenBank: ACT22631.1, GI: 253317413), *Rhodobacter sphaeroides*-derived mannitol-2-dehydrogenase (GenBank: AAC45771.1, GI: 2338764) or *Pseudomonas fluorescens* DSM 50106-derived mannitol-2-dehydrogenase (GenBank: AAC04472.1, GI: 2293418), and in terms of a conversion ratio of fructose into mannitol, the mannitol dehydrogenase is preferably *Leuconostoc pseudomesenteroides* ATCC 12291-derived mannitol-2-dehydrogenase.

The *Leuconostoc pseudomesenteroides* ATCC 12291-derived mannitol-2-dehydrogenase may have an amino acid sequence of SEQ ID NO: 43, the *Leuconostoc mesenteroides*-derived mannitol-2-dehydrogenase may have an amino acid sequence of SEQ ID NO: 44, the *Rhodobacter sphaeroides*-derived mannitol-2-dehydrogenase may have an amino acid sequence of SEQ ID NO: 45, and the *Pseudomonas fluorescens* DSM 50106-derived mannitol-2-dehydrogenase may have an amino acid sequence of SEQ ID NO: 46.

As needed, a reaction between the mixture of fructose and psicose and the mannitol dehydrogenase may be performed in the presence of a source of NADH (the reduced form of nicotinamide adenine dinucleotide (NAD)).

NADH is a coenzyme of a mannitol dehydrogenase, and may considerably increase the conversion ratio of fructose into mannitol when NADH is provided to the mannitol dehydrogenase. Therefore, fructose may be reduced from a reaction solution to more easily isolate psicose.

The NADH sources may include any one that is known in the art without limitation, and may include, for example, formic acid and a formate dehydrogenase. The formate dehydrogenase may be any formate dehydrogenase known in the art without limitation, and for example, *Mycobacterium vaccae* N10-derived formate dehydrogenase (FDH, GenBank: AB072394.1, GI: 15982576).

The *Mycobacterium vaccae* N10-derived formate dehydrogenase may have an amino acid sequence of SEQ ID NO: 49.

Likewise, the reaction between the reaction mixture and the mannitol dehydrogenase may be performed in microorganisms.

The microorganisms may be prokaryotic or eukaryotic cells, which are cultured in a liquid medium, and can be cultured at a high temperature as described above. The microorganisms may be, for example, bacteria, fungi or a combination thereof. The bacteria may be Gram-positive bacteria, Gram-negative bacteria or a combination thereof, and to increase psicose productivity, the bacteria are preferably Gram-positive bacteria. The Gram-negative bacteria may be the genus *Escherichia*. The Gram-positive bacteria may be the genus *Bascillus*, the genus *Corynebacterium*, the genus *Actinomyces*, the genus *Lactobacillus* or a combination thereof. Fungi may be yeast, the genus *Kluyveromyces* or a combination thereof.

Psicose is a functional sweetener, which can replace sucrose, and is used in food, and the microorganisms may be strains registered as generally recognized as safe (GRAS). For example, the microorganisms may be the genus *Corynebacterium*, more preferably, *Corynebacterium glutamicum*, and most preferably, *Corynebacterium glutamicum* ATCC 13032.

The microorganisms may express the mannitol dehydrogenase endogenously or by transformation. In such a case, the mannitol dehydrogenase may be generated in the microorganisms, and therefore mannitol production may be continuously performed by the reaction between the reaction mixture and the mannitol dehydrogenase in the microorganisms.

When the microorganisms are transformed with a gene encoding the mannitol dehydrogenase to express the mannitol dehydrogenase, the microorganisms may express the *Leuconostoc pseudomesenteroides* KCTC 3652-derived mannitol-2-dehydrogenase (GenBank: CAD31644.1, GI: 28865823), the *Leuconostoc mesenteroides*-derived mannitol-2-dehydrogenase (GenBank: ACT22631.1, GI: 253317413), the *Rhodobacter sphaeroides*-derived mannitol-2-dehydrogenase (GenBank: AAC45771.1, GI: 2338764) or the *Pseudomonas fluorescens* DSM 50106-derived mannitol-2-dehydrogenase (GenBank: AAC04472.1, GI: 2293418).

In addition, the microorganisms may express a formate dehydrogenase endogenously or by transformation. In such a case, the formate dehydrogenase is generated in the microorganisms to generate NADH from formic acid. Therefore, the generated NADH may serve as a coenzyme of the mannitol dehydrogenase to considerably increase the conversion ratio of fructose into mannitol.

The formate dehydrogenase may be, for example, *Mycobacterium vaccae* N10-derived formate dehydrogenase (FDH, GenBank: AB072394.1, GI: 15982576).

In addition, the microorganisms may express a glucose transport protein (GLF) endogenously or by transformation. In such a case, as the uptake of fructose, which is a substrate, into the microorganisms is increased, mannitol production may be increased. Therefore, as the fructose in the reaction solution is reduced, psicose may be more easily separated.

The glucose transport protein may be any one known in the art without limitation, and may be, for example, *Zymomonas mobilis* (*Zymomonas mobilis* subsp. *mobilis* ZM4, ATCC 31821 or KCTC 1534)-derived glucose transport protein (GenBank: AAG29864.1; GI: 11095424).

The *Zymomonas mobilis* (*Zymomonas mobilis* subsp. *mobilis* ZM4, ATCC 31821 or KCTC 1534)-derived glucose transport protein may have an amino acid sequence of SEQ ID NO: 50.

When the reaction between fructose and the epimerase thereof is performed in the microorganisms, the microorganisms may be cultured in the above-described medium.

When the microorganisms express the formate dehydrogenase endogenously or by transformation, the medium may further include formic acid.

In this case, the medium may have pH 6 to 7.5, and more preferably, pH 6.5 to 7.0. When the pH is in the above range, due to excellent mannitol productivity, psicose can be more easily separated. The above pH range may be obtained by using sodium acetate or PIPES as a solvent for a liquid medium, or a sodium phosphate buffer solution, or water.

In addition, when the microorganisms express the formate dehydrogenase endogenously or by transformation, the conversion of fructose into mannitol may be performed in an open reaction system. In such a case, $CO_2$ generated by the reaction between formic acid and the formate dehydrogenase is released, and thus an action of the formate dehydrogenase may be actively maintained. However, as the pH of the medium is increased by the consumption of the formic acid, the medium may contain a buffer solution, and more preferably, a PIPES buffer solution as a liquid solvent.

The method for producing psicose of the present invention may further include culturing the microorganisms in a fructose-free medium before the reaction between the reaction mixture and the mannitol dehydrogenase, such that the microorganisms are induced to have resting cells.

In addition, the present invention may further include, after the reaction between the reaction mixture and the mannitol dehydrogenase, recovering the microorganisms to be reused in conversion into a different substrate into mannitol.

Afterwards, the mannitol is separated from the mixture.

While fructose and psicose are difficult to be separated, because they have similar physical properties, mannitol has different physical properties from psicose, and therefore the psicose may be easily separated from the mannitol.

The separation method may be, but is not particularly limited to, for example, a method such as centrifugation, filtration, crystallization, ion exchange chromatography or the like, and since the mannitol and the psicose have a large difference in solubility for a solvent, the psicose may be separated from mannitol by crystallization according to the difference in solubility for a solvent. For example, such separation may be performed by a method for crystallizing mannitol by adding a first solvent and a second solvent that is different from the first solvent in a reaction solution containing the first solvent, or crystallizing mannitol by thermally concentrating a solvent in a reaction solution.

The solvent may be, but is not particularly limited to, for example, water, a salt aqueous solution, ethanol, hexane, or acetone. These solvents may be used individually or a mixture of two or more thereof.

In addition, the mannitol and the psicose may be separated by liquid chromatography. Since the psicose and the fructose have similar physical properties, they have a similar retention time in a column of the liquid chromatography, and thus the peak areas overlap. However, since the psicose and the mannitol have different physical properties and thus are separated into peaks, the psicose may be easily separated from the mannitol.

In addition, in one aspect of the present invention, the present invention provides a method for preparing psicose, which includes adding a mannitol dehydrogenase to a mixture of fructose and psicose to convert the fructose into mannitol.

The step of adding mannitol dehydrogenase to a mixture of fructose and psicose to convert the fructose into mannitol may be performed by converting fructose into psicose by a chemical or biological method as described above, and then adding a mannitol dehydrogenase to a mixture of the converted psicose and non-converted fructose so as to convert the fructose into mannitol.

As described above, a reaction between the reaction mixture and the mannitol dehydrogenase may be performed in microorganisms. A specific method is the same as described above.

Since psicose is a C3 epimer of fructose, which has sweetness like general saccharides, and has almost zero calorie since it is not metabolized in the human body, it may be used as a functional sweetener replacing sucrose for diabetic and obese patients. However, the fructose has high calories and is reduced in insulin sensitivity in hyperingestion, and therefore can be a main cause for diabetes.

However, mannitol is a polysaccharide which has low calories, is not easily absorbed in the body and requires a long-term metabolism, compared to the fructose, and a component used as a sweetener for diabetic patients.

Accordingly, when the mannitol dehydrogenase is applied to the mixture of fructose and psicose to convert the fructose into mannitol, even when psicose and mannitol are used as a sweetener in the form of a mixture without separation, the psicose may be used as a functional sweetener replacing sucrose, which reduces possibility of causing a metabolic syndrome such as diabetes, obesity or the like.

In addition, the present invention may further include preparing the mixture of fructose and psicose by a reaction between fructose as a substrate and an epimerase thereof.

The step of preparing the mixture of fructose and psicose by a reaction between fructose as a substrate and an epimerase thereof may be performed according to the above-described method.

In addition, the present invention may further include, after the reaction between the fructose and the epimerase thereof, recovering the microorganisms to be reused in conversion of another substrate into psicose, and such recovery may also be performed by the above-described method.

According to a method of the present invention, psicose can be separated at a high purity, and a production yield of the psicose is considerably improved.

According to the method of the present invention, a production amount and a production rate of the psicose are improved.

BRIEF DESCRIPTION OF THE DRWAINGS

FIG. 7 shows the comparison of amino acid sequences of psicose-3-epimerases derived from various strains.

Figure 9:
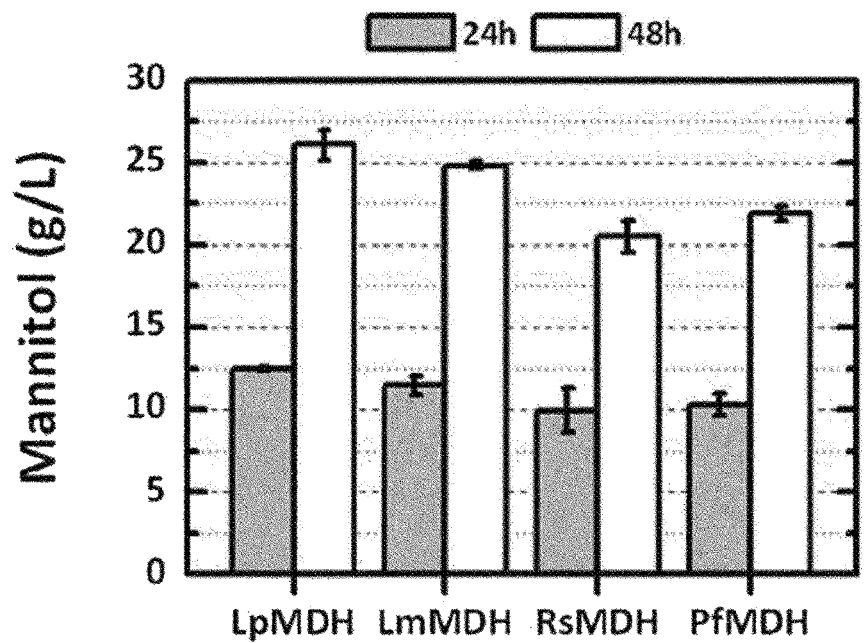

FIG. 9 is a diagram showing the mannitol production produced using *Corynebacterium* recombinant strains into which mannitol dehydrogenases and formate dehydrogenases are derived from various strains are introduced. LpMDH is *Leuconostoc pseudomesenteroides*-derived mannitol dehydrogenase, LmMDH is *Leuconostoc mesenteroides*-derived mannitol dehydrogenase, RsMDH is *Rhodobacter sphaeroides*-derived mannitol dehydrogenase, and PfMDH is *Pseudomonas fluorescens*-derived mannitol dehydrogenase.

Figure 10A:
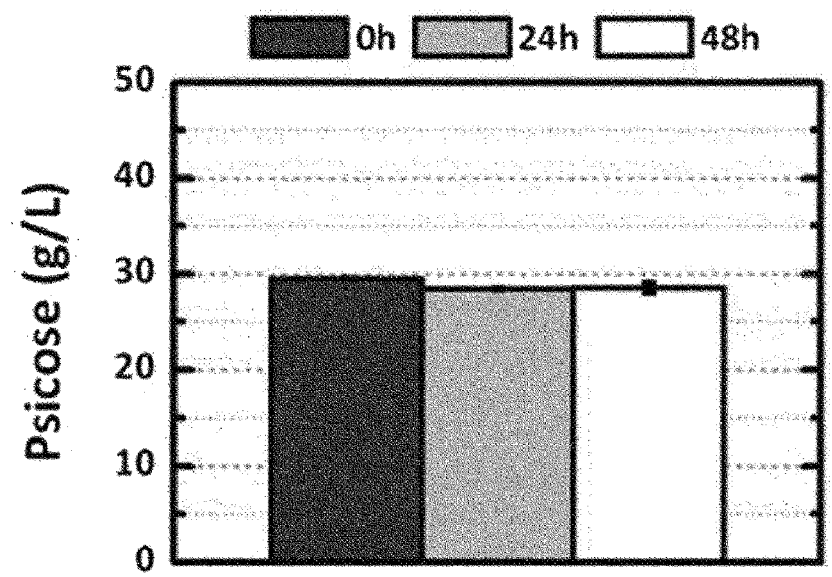
Figure 10B:
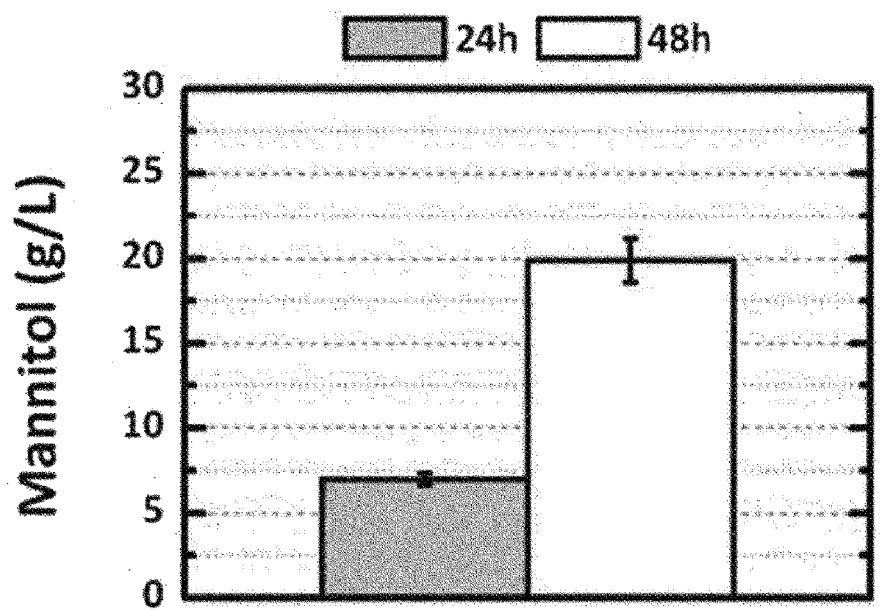

FIGS. 10(A) and 10(B) are diagrams showing an amount of psicose remaining without a reaction by a mannitol dehydrogenase and a production amount of mannitol converted from fructose, when mixed saccharides including psicose and fructose were provided as substrates.

Figure 11A:
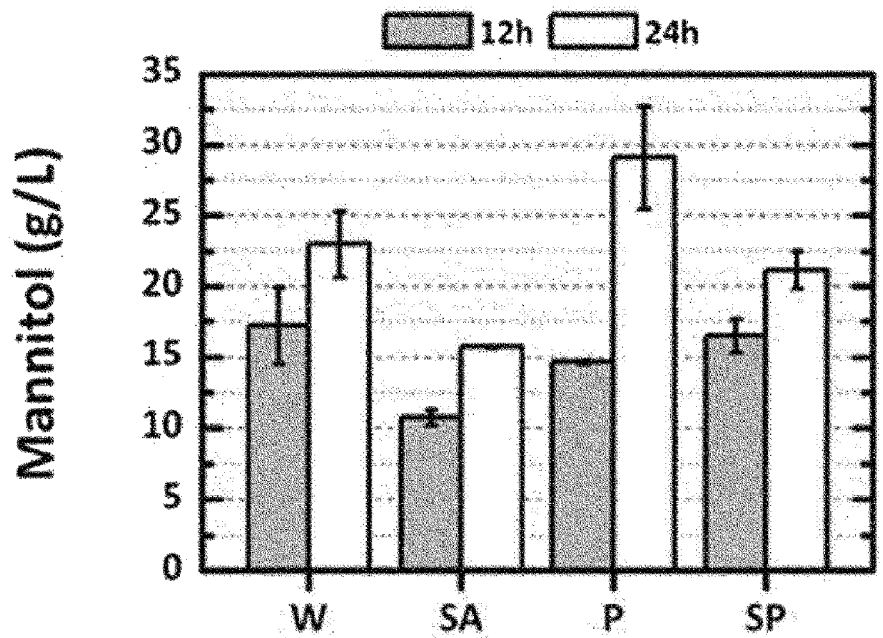
Figure 11B:
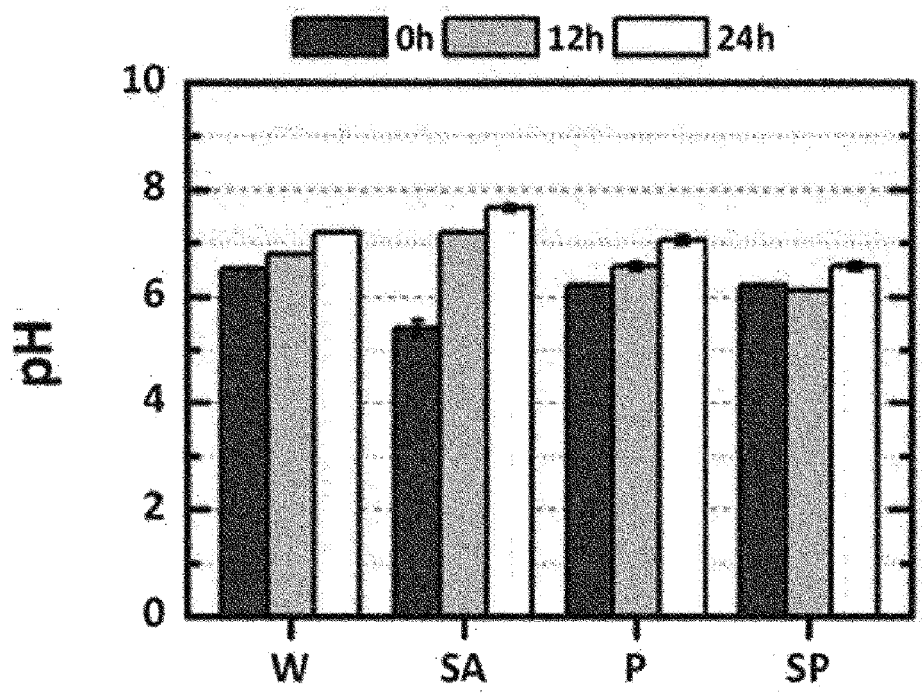

FIGS. 11(A) and 11(B) are diagrams showing a mannitol production amount and a pH change when a conversion medium containing buffer solutions with different pHs is used and when a conversion medium containing water without a buffer solution. W uses water without a buffer solution, SA uses a sodium acetate buffer solution with pH 5, P uses a PIPES buffer solution with pH 6, and SP uses a sodium phosphate buffer solution with pH 6.5 used as conversion media.

Figure 12A:
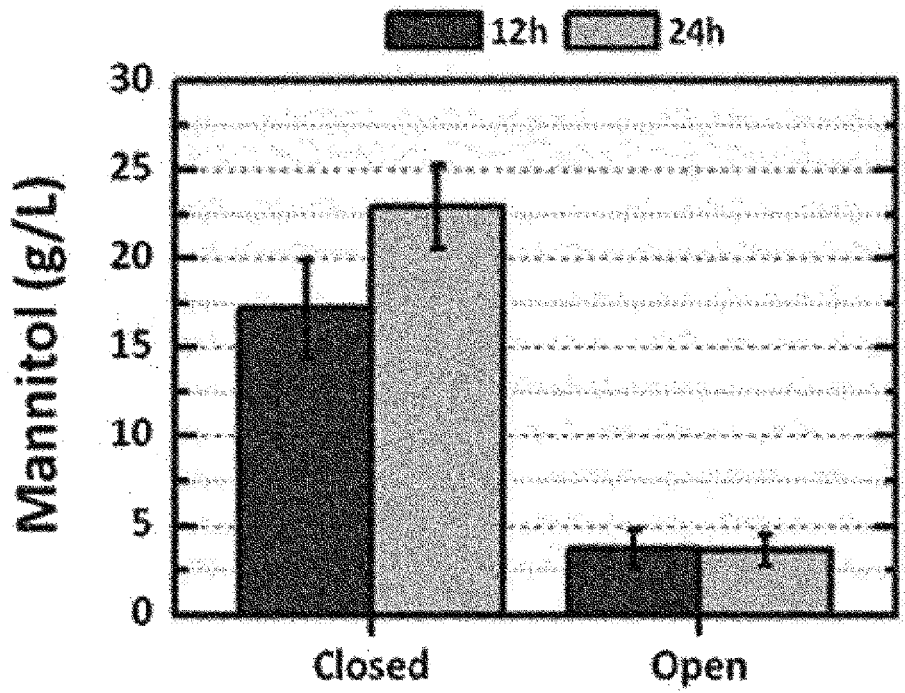
Figure 12B:
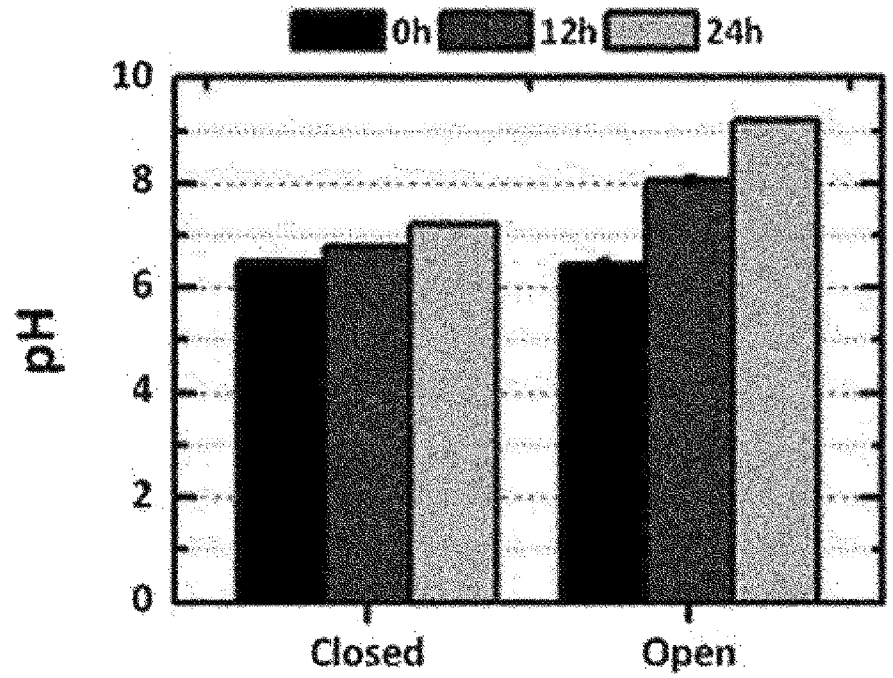

FIGS. 12(A) and 12(B) are diagrams comparing a mannitol production amount and a pH change according to the use of a conical tube, which is a closed reaction vessel, and a test tube, which is an open reaction vessel.

Figure 13:
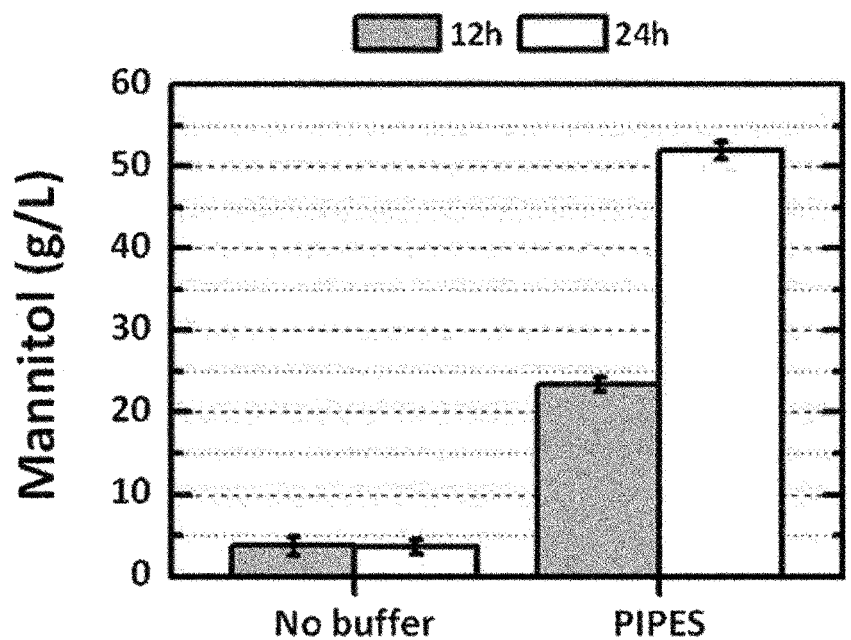

FIG. 13 is a diagram showing a mannitol production amount when water or a PIPES buffer solution with pH 6 is used as a conversion medium in a test tube, which is an open reaction vessel.

Figure 14:
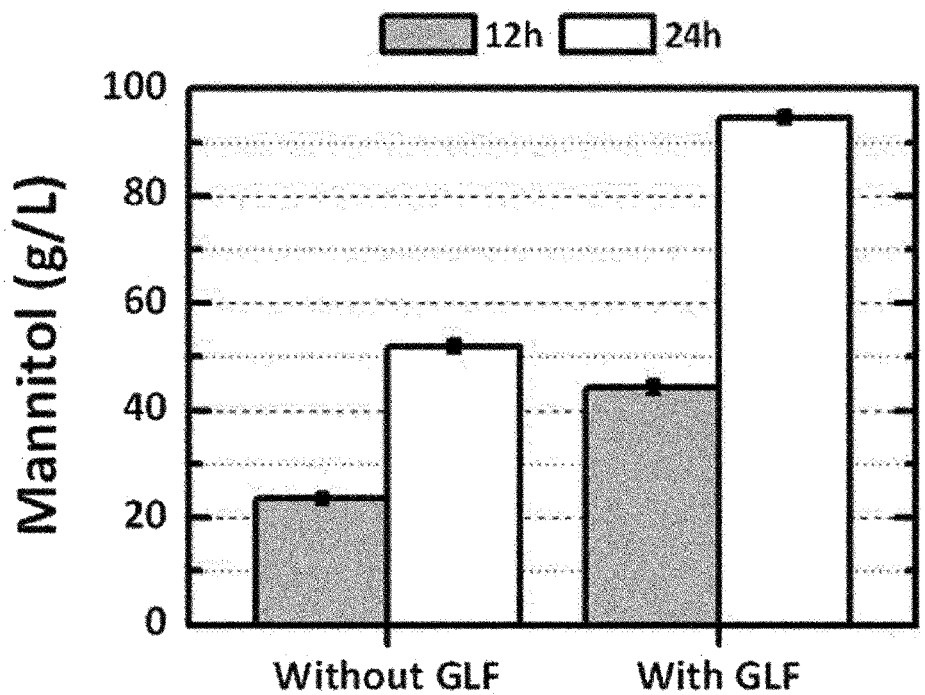

FIG. 14 is a diagram comparing a mannitol production amount according to whether or not a glucose transport protein (GLF) is introduced.

Figure 15:
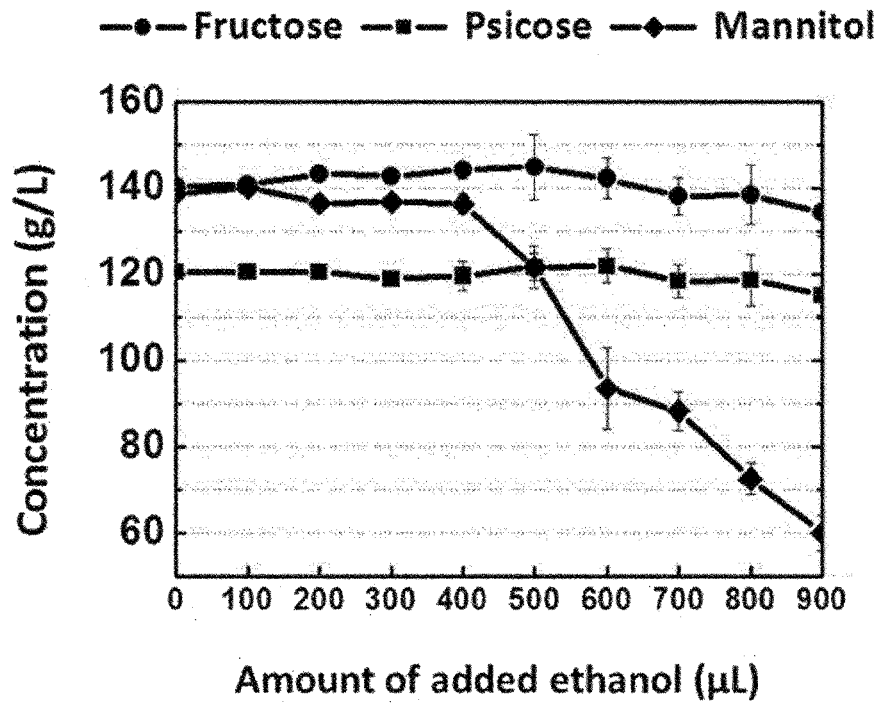

FIG. 15 is a diagram showing the concentrations of fructose, mannitol and psicose after crystallized mannitol is separated from a mixed saccharide solution for a mannitol conversion reaction according to an amount of added ethanol.

Figure 16:
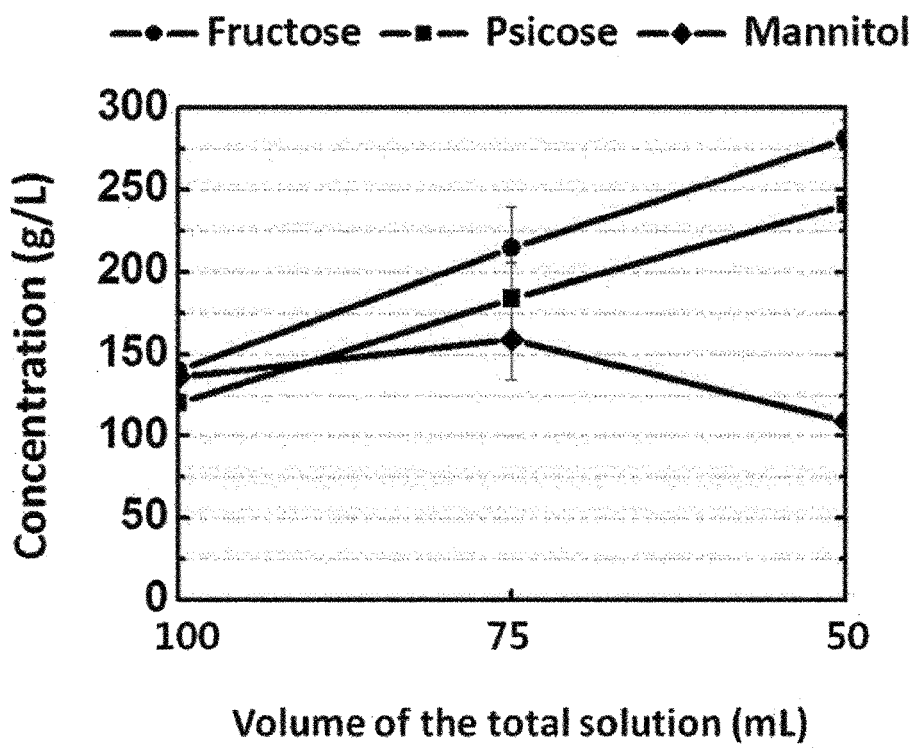

FIG. 16 is a diagram showing the concentrations of fructose, mannitol and psicose after crystallized mannitol is separated as the volume of a mixed saccharide solution for a mannitol conversion reaction is reduced by evaporation.

Figure 17A:
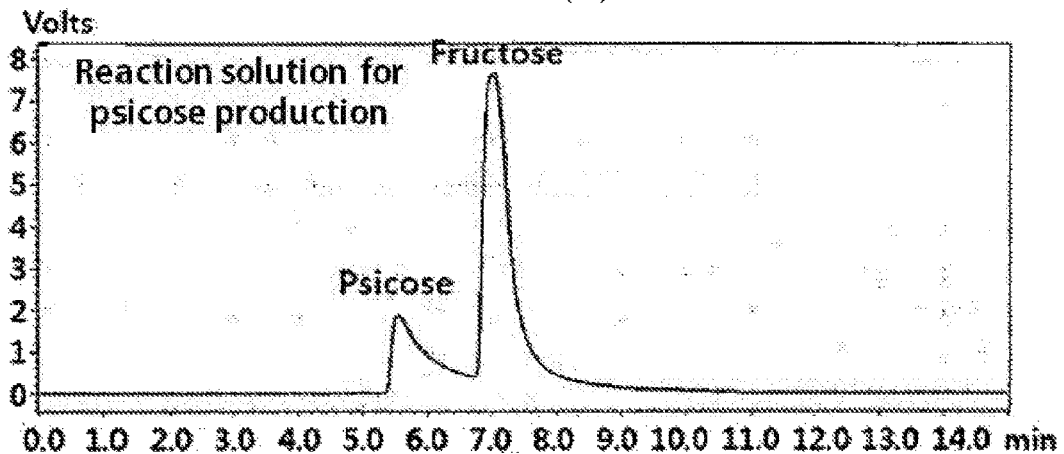
Figure 17B:
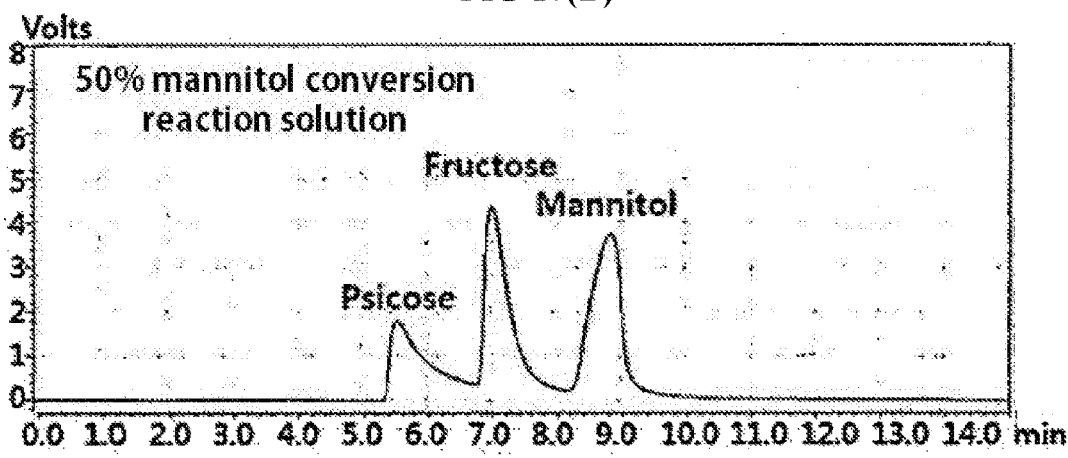
Figure 17C:
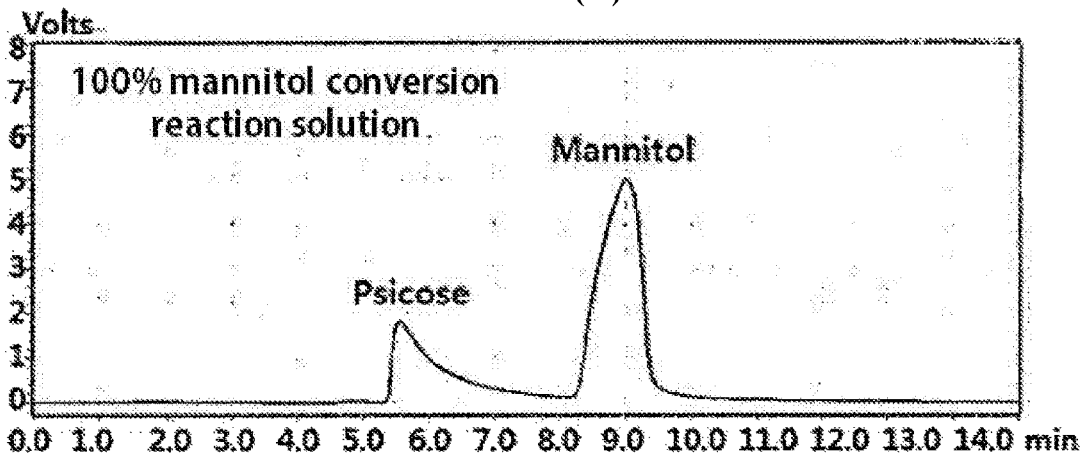

FIGS. 17(A) to 17(C) are diagrams comparing a resolution patterns of high performance liquid chromatography (HPLC) for mixed saccharides in a reaction solution depending on an additional mannitol conversion reaction after a psicose production process.

DETAILED DESCRIPTION

Hereinafter, the present invention will be fully described in detail with reference to examples.

EXAMPLES

1. Change in Psicose Production Rate and Production Amount According to Temperature in Process of Producing Psicose from Fructose Using *Corynebacterium glutamicum* Strain (1) Preparation of Recombinant Strain A pSGT208 shuttle vector into which a terminator and a lac prompter were inserted was constructed by modifying an *E. coli*-*Corynebacterium* shuttle vector, pCES208 (*J. Microbiol. Biotechnol.*, 18:639-647, 2008).

To produce psicose in *Corynebacterium glutamicum*, a psicose-3-epimerase was prepared by introducing a dpe gene (AGR_L_260, GI:15890243, SEQ ID NO: 1) of *Agrobacterium tumefaciens* (*Agrobacterium tumefaciens* str. C58; taxid:176299; GenBank NID: NC_003062, ATCC33970) into the constructed pSGT208 shuttle vector.

In detail, the dpe gene was amplified from the *Agrobacterium tumefaciens* genome using a primer 1 of SEQ ID NO: 31 and a primer 2 of SEQ ID NO: 32, cleaved with restriction enzymes KpnI and BamHI to be inserted into the same site of the pSGT208 shuttle vector, thereby constructing a pS208-dpe recombinant shuttle vector including psicose-3-epimerase.

Afterward, to increase the expression level of a psicose-3-epimerase in *Corynebacterium glutamicum*, in pS208-dpe, a lac promoter was substituted with a trc promoter derived from pTrc99a, and thus the resulting vector was named pS208cT-dpe.

Recombinant vectors pS208-dpe and pS208cT-dpe including the constructed psicose-3-epimerase and a pSGT208 vector, which was a negative control thereof, were introduced into wild-type *Corynebacterium glutamicum* ATCC 13032 for transformation, and thus were used in production of psicose from fructose. The transformation was performed by a method specified in the Handbook of *Corynebacterium glutamicum* (Lothar Eggeling et al., ISBN 0-8493-1821-1, 2005 by CRC press).

(2) Culture of Recombinant Strain and Production of Psicose Using the Strain

To ensure a high concentration of bacterial cells, the prepared *Corynebacterium glutamicum* transformant was seeded into 5 ml of a LB medium (Difco) containing 20 μg/ml of kanamycin to perform seed culture at 30° C. and 250 rpm, and then the cultured cells were seeded into a minimal medium (per liter, 1 g $K_2HPO_4$, 10 g $(NH_4)_2SO_4$, 0.4 g $MgSO_4 7H_2O$, 20 mg $FeSO_4 7H_2O$, 20 mg $MnSO_4 5H_2O$, 50 mg NaCl, 2 g urea, 0.1 mg biotin, 0.1 mg thiamine) containing 10 g/L glucose and 20 μg/ml of kanamycin to perform main culture. For the main culture, the transformants were cultured in a 500 ml Erlenmeyer flask with markings to have a volume of 100 ml at 37° C. and 180 rpm for 12 hours, thereby leading to a sufficient cell mass and sufficient expression of a protein.

The obtained culture solution was centrifuged to remove the supernatant and recover the cells, and the cells were resuspended in the above-mentioned minimal medium containing 40% (w/v) fructose as a substrate to have a cell concentration of 40 at $OD_{600}$, followed by a resting cell conversion reaction at 25, 30, 37, 50, 60 or 70° C. and 180 rpm.

Concentrations of fructose and psicose were measured using HPLC. For HPLC, SCL-10A (Shimadzu, Japan) equipped with a Kromasil $5NH_2$ column (4.6 mm×250 mm) was used, and separation was performed by adding 75% acetonitrile as a mobile phase at 1.5 mL/min and 40° C., and analysis was performed using a reflective index (RI) detector. A retention time of fructose under the above conditions was 5.5 minutes, and a retention time of psicose was 4.6 minutes.

Figure 1:
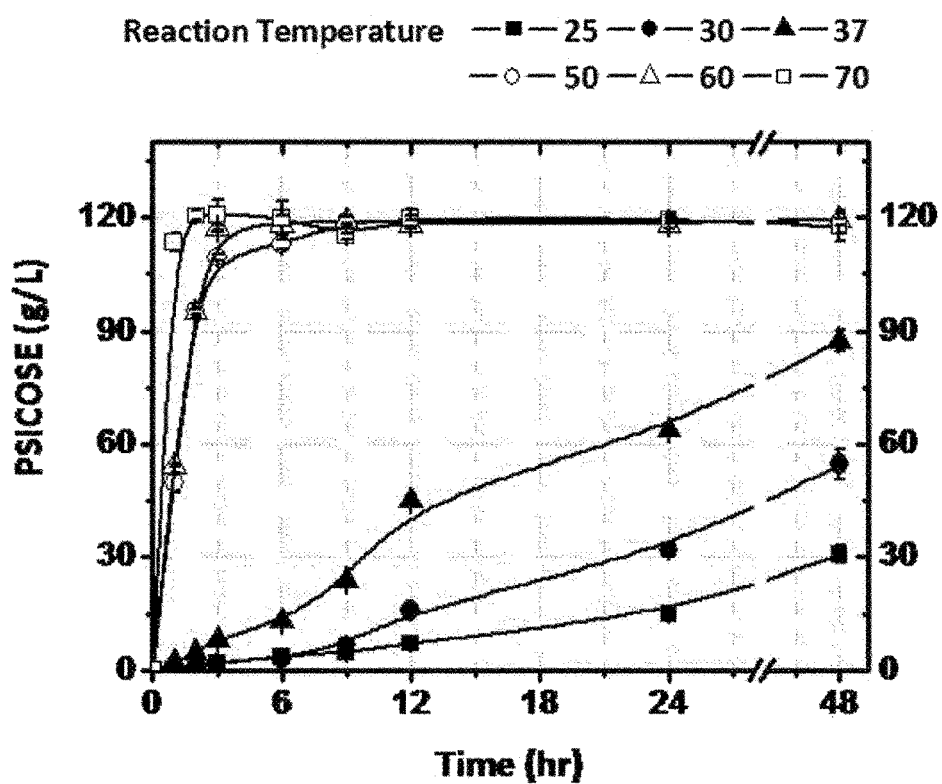
FIG. 1 shows the psicose production amount from fructose, which is a substrate, measured according to a reaction temperature of a resting cell conversion reaction from a *Corynebacterium glutamicum* transformant into which a psicose-3-epimerase is introduced.

Measurement results are shown in FIG. 1. Referring to FIG. 1, a pSGT208cT-dpe shuttle vector-introduced *Corynebacterium glutamicum* ATCC13032 strain was subjected to a conversion reaction in a medium containing 40% fructose, which showed that, as reaction temperature increased, a production rate for psicose considerably increased, and a production amount also increased. Particularly, in experimental groups reacted at 50, 60 and 70° C., psicose-3-epimerase reached equilibrium within approximately 3 hours, and approximately 120 g/L of psicose was produced. Such a result can show that the conversion rate of a psicose-3-epimerase from fructose to psicose and the production amount were dependent on a temperature.

Starting from 50° C., the production amount drastically increased, and the temperature was considerably higher than that required for a conventional enzyme reaction, and it was determined that the reaction patterns between an enzyme and a substrate vary at the corresponding temperature.

2. Change in Production Rate and Production Amount of Psicose According to Temperature in Production of Psicose from Fructose Using *E. coli*

According to the method described in Example 1 in Korean Patent No. 10-1106253, an *E. coli* MG1655 (ΔpfkA, als2) strain was prepared by transforming a pTrc99A vector with an *Agrobacterium tumefaciens*-derived psicose-3-epimerase-introduced pTPE plasmid.

To block a psicose degradation pathway, *E. coli* MG1655 from which pfkA (SEQ ID NO: 11) and als2 (SEQ ID NOs: 14, 15, 16, 17, 18 and 19) genes were deleted were used.

To ensure a high concentration of cells, the *E. coli* MG1655 transformant prepared as described above was seeded into 5 ml LB medium (Difco) containing 100 µg/ml of ampicillin for seed culture at 37° C. and 250 rpm, and then seeded into a 2YT medium containing 10 g/L of glucose and 100 µg/ml of ampicillin for main culture. For the main culture, the transformants were cultured in a 500 ml Erlenmeyer flask with markings to have a volume of 100 ml at 37° C. and 180 rpm for 12 hours, thereby leading to a sufficient cell mass and sufficient expression of a protein.

The obtained culture solution was centrifuged to remove the supernatant and recover the cells, and the cells were resuspended in *E. coli* minimal medium M9 (per liter, 11.3 g M9 minimal salts (Difco), 0.1 mL 1M $CaCl_2$, 2 mL 1M $MgSO_4$, 1 mL 100 mM $MnSO_45H_2O$) containing 40% (w/v) fructose as a substrate to have a cell concentration of 40 at $OD_{600}$, followed by a resting cell conversion reaction at 37, 60 or 70° C. and 180 rpm under respective conditions. Concentrations of fructose and psicose were analyzed according to the method described in Example 1. Measurement results are shown in FIG. 2.

Figure 2:
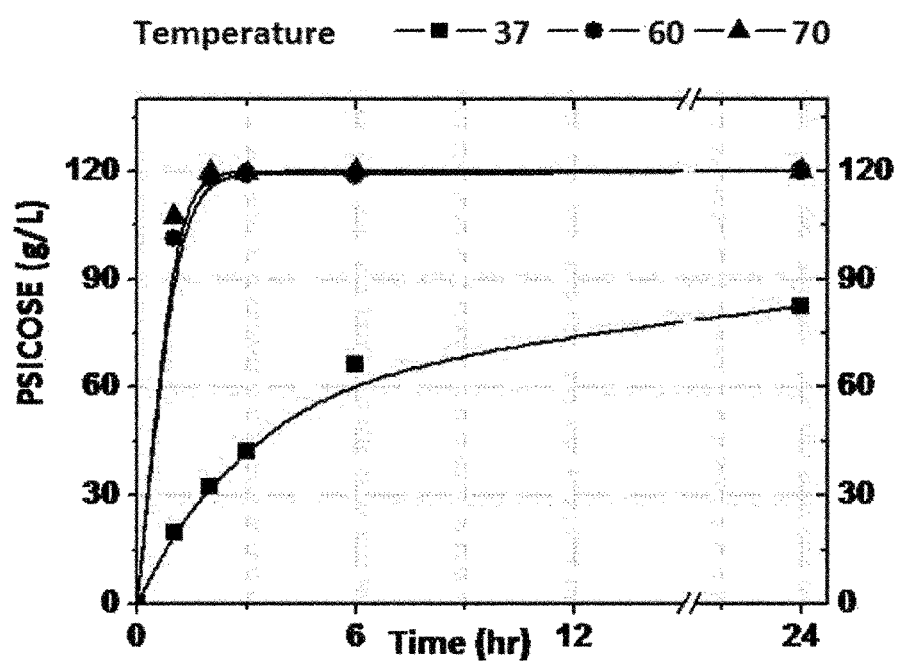
FIG. 2 shows the psicose production amount from fructose, which is a substrate, measured according to a reaction temperature of a resting cell conversion reaction from an *E. coli* MG1655 transformant into which a psicose-3-epimerase is introduced.

Referring to FIG. 2, the pTPE vector-introduced *E. coli* MG1655 (ΔpfkA, als2) strains were also subjected to a conversion reaction in a medium containing 40% fructose, which showed that, as the reaction temperature increased, a psicose production rate considerably increased and a production amount also increased. Particularly, in experimental groups reacted at 60 or 70° C., like the experiment using *Corynebacterium*, psicose-3-epimerase reached equilibrium within approximately 2 hours, and approximately 120 g/L of psicose was produced.

Such a result also showed that the psicose conversion rate of psicose-3-epimerase from fructose and the psicose production amount were dependent on a temperature.

According to a resting cell conversion reaction experiment performed for a representative Gram-positive bacteria *Corynebacterium* and a representative Gram-negative bacteria *E. coli* at a high temperature, it can be seen that, since protected from a severe external environment in cells, a saccharide conversion enzyme, psicose-3-epimerase, was not thermally denatured, and psicose was produced at a high rate at a high temperature, rather than in a pure enzyme state. The advantage of such a cell conversion reaction seems to be also applied to most types of microorganisms.

3. Continuous Production from Fructose to Psicose Through Cell Recovery and Reuse in Resting Cell Conversion Reaction of *Corynebacterium glutamicum* Transformant Strain According to the results of Examples 1 and 2, when psicose-3-epimerase was subjected to a conversion reaction in a *Corynebacterium* or *E. coli* transformant at a high temperature of 50° C. or more, the production amount of psicose reached the maximum level within 3 hours, and did not increase any more.

That is, even three hours after the reaction reached equilibrium at which the psicose production is in the maximum level, to confirm how much an activity of the psicose-3-epimerase to convert fructose into psicose, cells used in production of psicose through a resting cell conversion reaction performed for 3 hours in the presence of fructose were recovered, and then reused in the resting cell conversion reaction for producing psicose.

The resting cell conversion reaction by the cell reuse was repeated three times at 60° C. The first resting cell conversion reaction was represented as R0, a resting cell conversion reaction by the first reuse of cells recovered from the above-described reaction solution was represented as R1, and a resting cell conversion reaction by the second reuse thereof was represented as R2, and a resting cell conversion reaction by the third reuse thereof was represented as R3. Culture conditions and an analysis method were the same as described in Example 1. Results are shown in FIG. 3.

Figure 3:
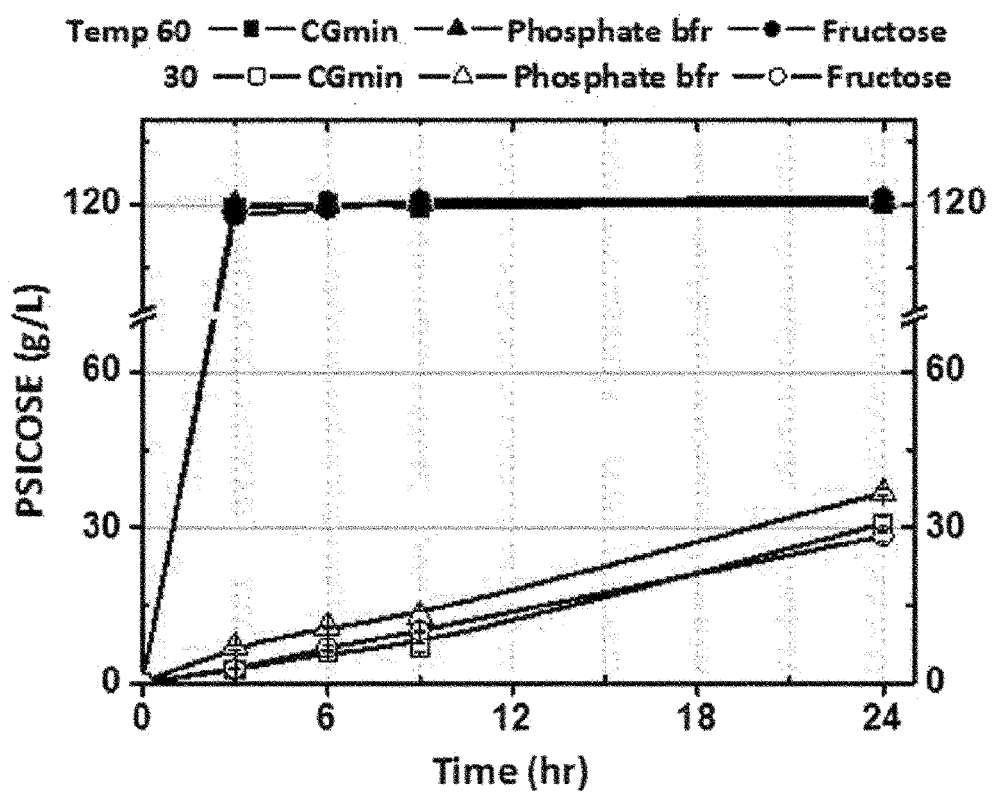
FIG. 3 shows the psicose production amount obtained by recovering bacterial cells after a resting cell conversion reaction for producing psicose is performed at 60° C. for 3 hours using *Corynebacterium glutamicum* and *E. coli* MG1655 transformants into which psicose-3-epimerase is introduced, and then performing a reaction again under the same conditions.

Referring to FIG. 3, bacterial cells can be reused in a saccharide conversion reaction at a high temperature of 60° C. However, as the cells were used multiple times, the enzyme activity seems to be reduced by a certain level. In addition, it can be seen that, for reuse of cells at a high temperature, the Gram-positive *Corynebacterium glutamicum* strain exhibits a higher retained enzyme activity than the Gram-negative *E. coli* MG1655 strain.

4. Production of Psicose from Fructose in Various Resting Cell Conversion Reaction Media In Example 1, for a conversion reaction for producing psicose from fructose in *Corynebacterium glutamicum*, a 40% fructose-contained minimal medium (per liter, 1 g $K_2HPO_4$, 10 g $(NH_4)_2SO_4$, 0.4 g $MgSO_47H_2O$, 20 mg $FeSO_47H_2O$, 20 mg $MnSO_45H_2O$, 50 mg NaCl, 2 g urea, 0.1 mg biotin, 0.1 mg thiamine) was used. A more economic and simple medium can be prepared by minimizing components for a medium used in the conversion reaction, and the productivity of psicose when this medium is used was compared with that when the medium used in Example 1 was used.

Figure 4:
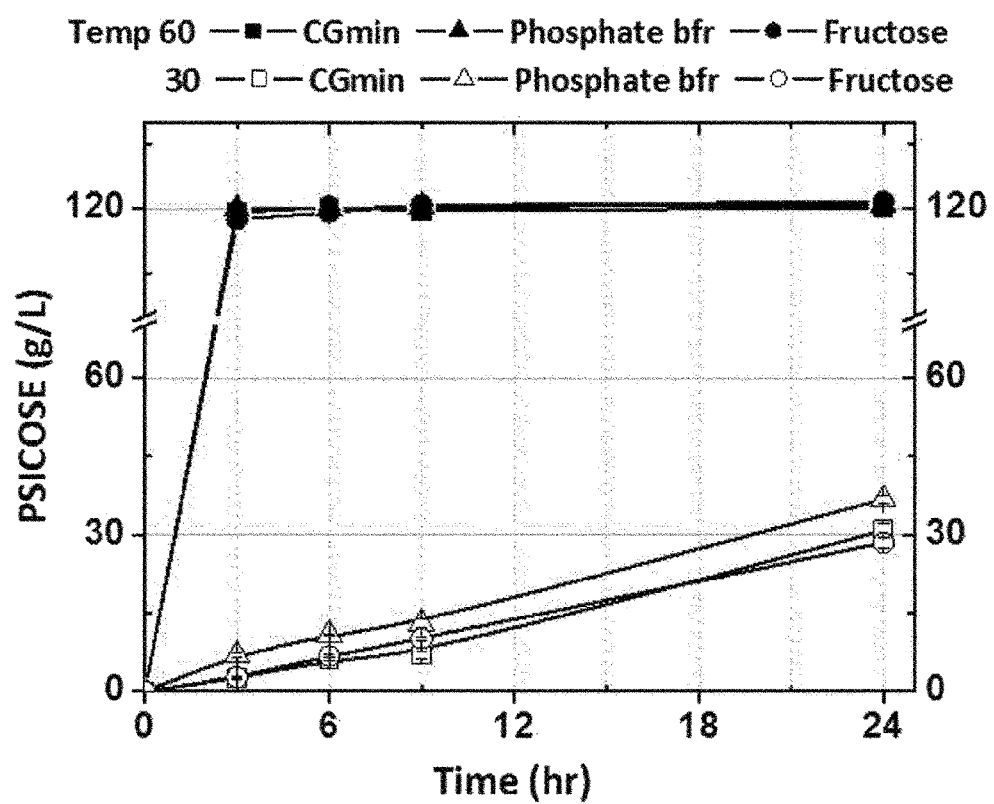
FIG. 4 shows the psicose production amount from fructose according to a composition change of a psicose production reaction medium, which is used in a resting cell conversion reaction of a *Corynebacterium glutamicum* transformant into which a psicose-3-epimerase is introduced.

Referring to FIG. 4, although a phosphate buffer (pH 7) medium containing 40% fructose and 0.1 mM MnSO$_4$, or more simply, a medium containing only 40% fructose and 0.1 mM MnSO$_4$ was used, there is no significant difference in the final psicose production amount. This result was shown at both reaction temperatures of 30° C. and 60° C. When 0.1 mM MnSO$_4$ was not added as a cofactor of psicose-3-epimerase, the production amount was reduced.

In this example, it can be seen that components for the medium used in the resting cell conversion reaction for producing psicose only include fructose as a substrate and MnSO$_4$, which is the cofactor of psicose-3-epimerase.

5. Preparation of Recombinant *Corynebacterium glutamicum* Including Polynucleotides Encoding Amino Acid Sequences of Psicose-3-epimerases Derived from Various Strains The total genome of *Anaerostipes caccae* (*Anaerostipes caccae* DSM 14662; taxid: 411490) was purchased from DSMZ (Germany). The first PCR was performed with the purchased total genome as a template using a primer pair of SEQ ID NOs: 33 and 34 to include a psicose-3-epimerase estimated gene (AP endonuclease; Sequence ID: gb|EDR98778.1|; GI: 167654649; SEQ ID NO: 4). The second PCR was performed using the amplified PCR product as a template and a primer pair of SEQ ID NOs: 35 and 36, which specifically bind to a psicose-3-epimerase gene.

The obtained PCR product was inserted into the same enzyme site of pS208cT-dpe (the vector described in Example 1 of Korean Patent Application No. 10-2013-0060703) using restriction enzymes BamHI and XbaI, thereby constructing a recombinant vector pS208cT-AcDPE.

The constructed pS208cT-AcDPE vector was introduced into wild-type *Corynebacterium glutamicum* ATCC 13032 for transformation, and was used in production of psicose from fructose. The transformation was performed by the method described in the Handbook of *Corynebacterium glutamicum* (Lothar Eggeling et al., ISBN 0-8493-1821-1, 2005 by CRC press).

The obtained recombinant *Corynebacterium glutamicum* strain was stored at −80° C. and then cultured.

A plasmid including a psicose-3-epimerase estimated gene (hypothetical protein CLOBOL_00069; Sequence ID: gb|EDP19602.1|; GI:15844190; SEQ ID NO: 9) of *Clostridium bolteae* (*Clostridium bolteae* ATCC BAA-613; taxid:411902) was obtained from Korea Yakult Co., Ltd. PCR was performed using a primer pair of SEQ ID NOs: 37 and 38, which specifically bind to the psicose-3-epimerase gene.

The obtained PCR product was inserted into the same enzyme site of pS208cT-dpe (the vector described in Example 1 of Korean Patent Application No. 10-2013-0060703) using restriction enzymes KpnI and XbaI, thereby constructing a recombinant vector pS208cT-CbDPE.

The constructed recombinant vector pS208cT-CbDPE was introduced to transform wild-type *Corynebacterium glutamicum* ATCC 13032 by the method described above, and was used in production of psicose from fructose. The recombinant *Corynebacterium glutamicum* strain was stored at −80° C. and cultured.

The total genome of *Clostridium hylemonae* (*Clostridium hylemonae* DSM 15053; taxid:553973) was purchased from DSMZ (Germany). The first PCR was performed with the purchased total genome as a template and a primer pair of SEQ ID NOs: 39 and 40 to include a psicose-3-epimerase estimated gene (dolichol monophosphate mannose synthase; Sequence ID:ref|WP_006442985.1|; GI:225161759; SEQ ID NO: 10). The second PCR was performed with the amplified PCR product as a template and a primer pair of SEQ ID NOs: 41 and 42, which specifically bind to a psicose-3-epimerase gene.

The obtained PCR product was inserted into the same enzyme site of pS208cT-dpe (the vector described in Example 1 of Korean Patent Application No. 10-2013-0060703) using restriction enzymes BamHI and XbaI, thereby constructing a recombinant vector pS208cT-ChDPE.

The constructed pS208cT-ChDPE vector was introduced into wild-type *Corynebacterium glutamicum* ATCC 13032 for transformation, and was used in production of psicose from fructose. The obtained recombinant *Corynebacterium glutamicum* strain was stored at −80° C. and cultured.

6. Production of Psicose from Fructose Using Recombinant *Corynebacterium glutamicum* Strain into which Psicose-3-Epimerases Derived from Various Strains were Introduced The production of psicose from a high concentration of fructose using the *Corynebacterium glutamicum* transformant constructed in Example 5 was confirmed.

The transformant was seeded in a 2YT medium containing 20 μg/ml of kanamycin for seed culture at 30° C. and 250 rpm, and then cultured again in a 2YT medium containing 20 μg/ml of kanamycin for main culture. For the main culture, the transformants were cultured in a 300 ml Erlenmeyer flask with markings to have a volume of 60 ml at 30° C. and 180 rpm for 7 hours, thereby leading to a sufficient cell mass and sufficient expression of a protein.

The obtained culture solution was centrifuged to remove the supernatant and recover the cells, and the cells were subjected to a resting cell conversion reaction at 55° C. using a simple conversion reaction medium containing 20 μg/ml kanamycin, 40% (w/v) fructose as a substrate and 0.1 mM manganese or cobalt known as a main cofactor of psicose-3-epimerase. Concentrations of fructose and psicose were measured in the same manner as described in Example 1. Measurement results are shown in FIG. 5 (AtDPE refers to the conventionally used psicose-3-epimerase of *Agrobacterium tumefaciens*).

Figure 5:
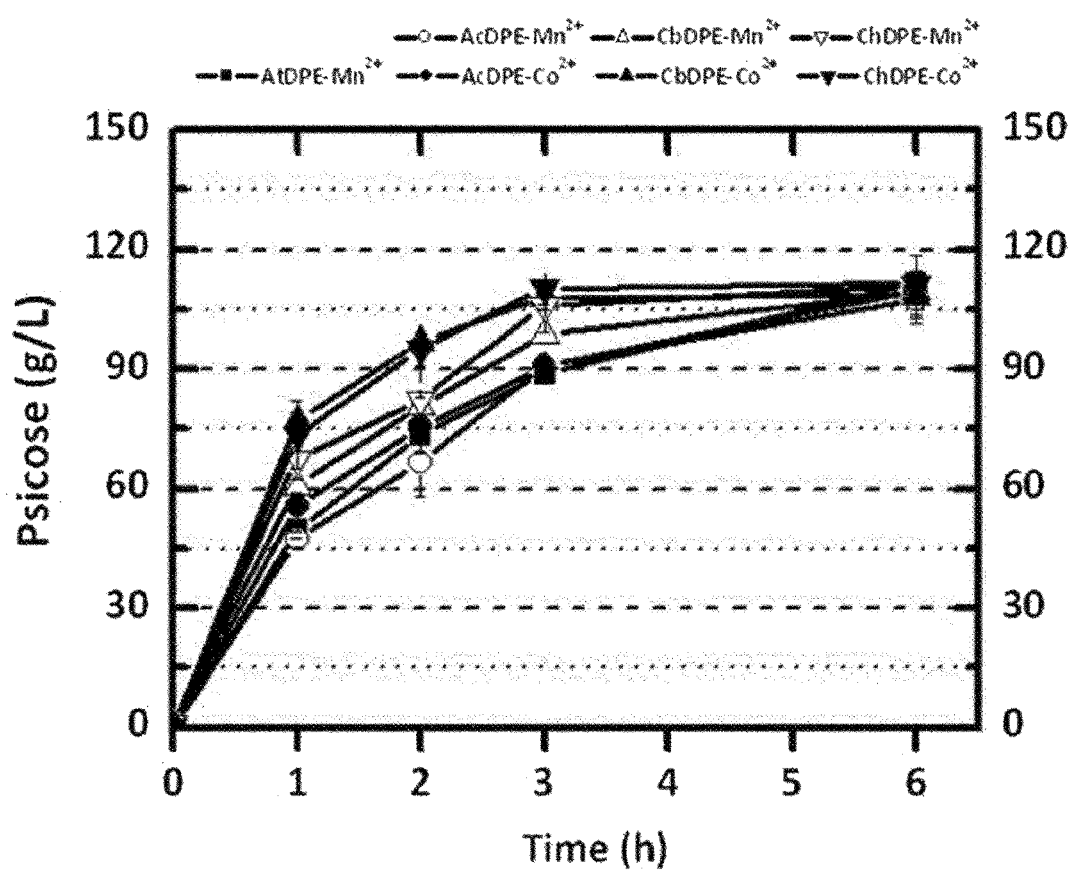
FIG. 5 shows the psicose production amount according to a psicose-3-epimerase-derived strain and the composition of a psicose production reaction medium in a resting cell conversion reaction of a *Corynebacterium glutamicum* transformant into which a psicose-3-epimerase is introduced.

Referring to FIG. 5, when cobalt, rather than manganese, was used as a cofactor, it seems that, in all recombinant strains into which various psicose-3-epimerases were introduced, a production rate of psicose was a little faster.

While it seems that psicose production amounts of recombinant *Corynebacterium glutamicum* into which *Anaerostipes* and *Agrobacterium*-derived psicose-3-epimerases were introduced reached equilibrium within 6 hours, a psicose production amount of recombinant *Corynebacterium glutamicum* into which *Clostridium*-derived psicose-3-epimerase was introduced seems to reach equilibrium within three hours even when manganese was used as a cofactor.

Therefore, when the *Clostridium*-derived psicose-3-epimerase was used, the psicose production from fructose can be confirmed, and it can also be known that the psicose production rate was faster than when the *Agrobacterium*-derived psicose-3-epimerase was used.

7. Maintenance of Continuous Activity to Produce Psicose at High Temperature in Recombinant *Corynebacterium glutamicum* Strains into which Psicose-3-Epimerases Derived from Various Strains were Introduced According to the results obtained in Examples 1 and 2, it was confirmed that when the conversion reaction was performed at a high temperature of 50° C. or more, total psicose production was achieved within three hours. Likewise, since the production of psicose from fructose is fast under such a high temperature condition, for the reuse of bacterial cells, psicose-3-epimerase which is stable at a high temperature for a long time is needed. Therefore, it was confirmed how much psicose-3-epimerases derived from various strains maintained the activity at a high concentration.

The bacterial cells obtained by the method described in Example 1 were suspended in 2YT, and then heat was continuously applied thereto using a shaking incubator at 60° C. for 0, 3, 6, 9, 12, or 24 hours. After heating for each period of time, the bacterial cells were recovered and resuspended in a simple conversion reaction medium containing 20 μg/ml kanamycin, and only 0.1 mM manganese and 40% (w/v) fructose to perform a resting cell conversion reaction at 60° C. for 3 hours. Concentrations of fructose and psicose were measured in the same manner as described in the method of Example 1. Measurement results are shown in FIG. 6.

Figure 6:
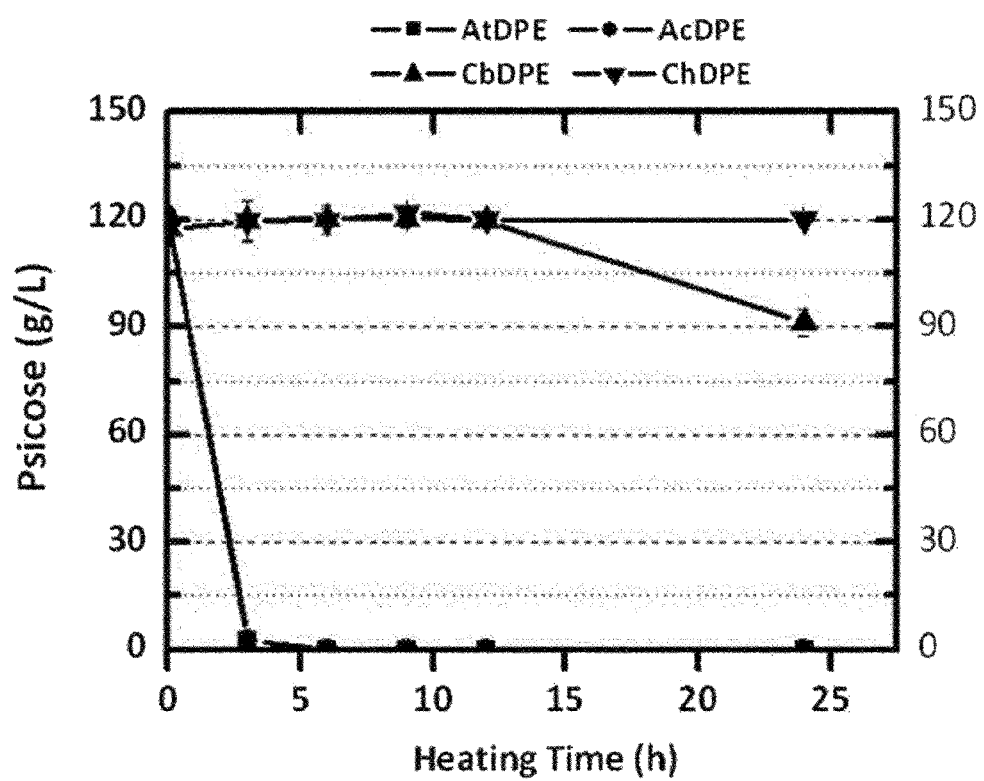
FIG. 6 shows the psicose production amount according to a psicose-3-epimerase-derived strain and a heating time in a resting cell conversion reaction of a *Corynebacterium glutamicum* transformant into which a psicose-3-epimerase is introduced.

Referring to FIG. 6, it is shown that after heating at 60° C. for 3 hours, the recombinant *Corynebacterium glutamicum* into which the conventionally used *Agrobacterium*-derived psicose-3-epimerase and *Anaerostipes*-derived psicose-3-epimerase were introduced rarely produce psicose. Contrarily, the recombinant *Corynebacterium glutamicum* into which *Clostridium*-derived psicose-3-epimerase was introduced seems to maintain psicose production even after heating for 24 hours, and it is considered that the recombinant *Corynebacterium glutamicum* of the present invention is more advantageous for psicose production at a high temperature process than the *Agrobacterium*-derived psicose-3-epimerase.

It has been known that, when the amino acids no. 33 or 213 in the sequence (Reference 1) critical for thermal stability of *Agrobacterium tumefaciens*-derived psicose-3-epimerase was replaced with leucine or cysteine, respectively, the half-lifetime of the enzyme at 50° C. increased 3.3 times or 7.2 times, respectively, or when all of the amino acids were replaced, the half-life of the enzyme at 50° C. increased 29.9 times.

The comparison between the amino acid sequence of the *Agrobacterium tumefaciens*-derived psicose-3-epimerase and the amino acid sequence of the *Clostridium*-derived psicose-3-epimerase was shown in FIG. 7, and referring to this, the *Clostridium*-derived psicose-3-epimerase having a high thermal stability had a sequence corresponding to one or both of the above-described amino acid substitutions.

8. Production of Psicose from Fructose Through Cell Recovery and Reuse in Resting Cell Conversion Reaction of Recombinant *Corynebacterium glutamicum* Transformant Strain into which *Clostridium*-Derived Psicose-3-Epimerase was Introduced In Example 7, it was confirmed that the *Clostridium*-derived psicose-3-epimerase has a high stability at a high temperature, a bacterial cell reuse effect was confirmed after the resting cell conversion reaction at a high temperature of the recombinant *Corynebacterium glutamicum* cells into which *Clostridium hylemonae* psicose-3-epimerase was introduced, among the two recombinant strains into which *Clostridium*-derived psicose-3-epimerase was introduced.

The bacterial cells obtained in the same manner as described in Example 3 were subjected to a resting cell conversion reaction at 60° C. for 3 hours, recovered to perform a resting cell conversion reaction again in the same manner, and then reused total three times (the experiment was performed under the same condition as used in Example 3). The first resting cell conversion reaction was represented as R0, a resting cell conversion reaction by the first reuse of bacterial cells recovered from the above-described reaction solution was represented as R1, and a resting cell conversion reaction by the second reuse thereof was represented as R2, and a resting cell conversion reaction by the third reuse thereof was represented as R3. Results are shown in FIG. 8.

Figure 8:
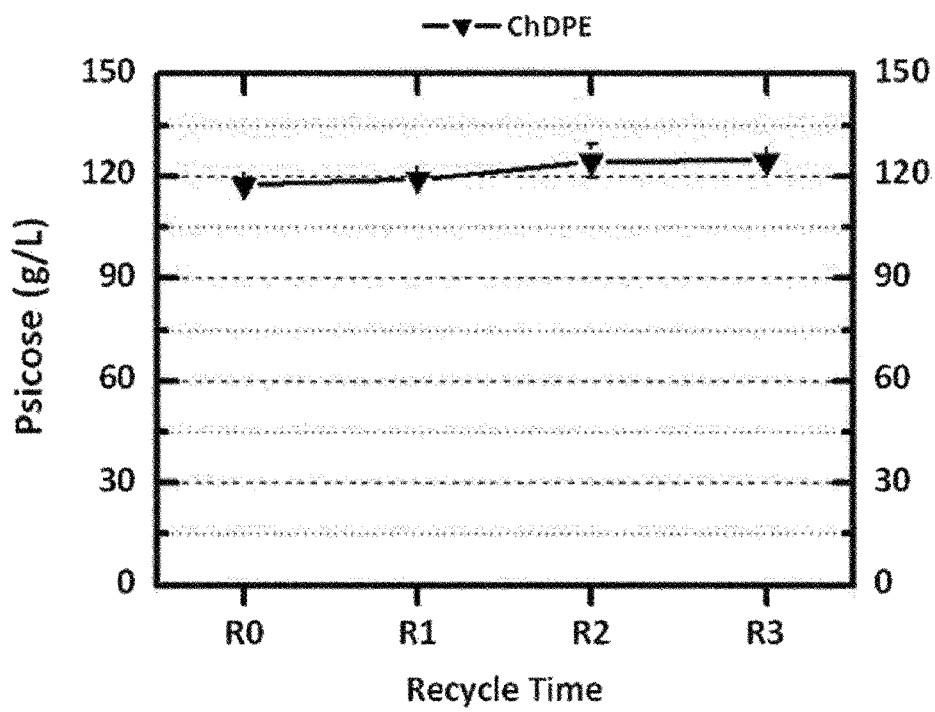
FIG. 8 shows the psicose production amount according to a reuse number of *Corynebacterium glutamicum* into which *Clostridium*-derived psicose-3-epimerase is introduced.

Referring to FIG. 8, it can be seen that, in case of the reuse of bacterial cells several times at a high temperature, the recombinant bacterial cells into which *Clostridium*-derived psicose-3-epimerase was introduced were maintained at a predetermined level without a decrease in psicose production amount. According to the results shown in Example 7, it can be confirmed that the thermal stability of the enzyme itself is very advantageous for the reuse of bacterial cells as well as a continuous saccharide conversion reaction at a high temperature.

9. Development of *Corynebacterium glutamicum* Recombinant Strain for Producing Mannitol from Fructose (1) Development of Recombinant *Corynebacterium* Strain The pSGT208 vector (the vector described in Example 1 of Korean Patent Application No. 10-2013-0060703), which was modified to easily clone an *E. coli-Corynebacterium* shuttle vector, for example, a pCES208 vector was used. A trc promoter was used as a promoter to allow continuous expression by removing a lac operator.

As mannitol producing enzymes, *Leuconostoc pseudomesenteroides* ATCC 12291 (or KCTC 3652), *Leuconostoc mesenteroides*, *Rhodobacter sphaeroides* and *Pseudomonas fluorescens* DSM 50106-derived enzymes were used.

The *Leuconostoc pseudomesenteroides* strain was purchased from KCTC and used as a template following purification of the total genome thereof, and PCR was performed using a primer pair of SEQ ID NOs: 47 and 48 as primers to include mannitol dehydrogenase (mannitol 2-dehydrogenase; MDH; GenBank: AJ486977.1, GI: 28865822, SEQ ID NO: 43, LpMDH).

*Leuconostoc mesenteroides*-derived mannitol dehydrogenase (GenBank: ACT22631.1, GI: 253317413, SEQ ID NO: 44, LmMDH), *Rhodobacter sphaeroides*-derived mannitol dehydrogenase (GenBank: AAC45771.1, GI: 2338764, SEQ ID NO: 45, RsMDH) and *Pseudomonas fluorescens*-derived mannitol dehydrogenase (GenBank: AAC04472.1, GI: 2293418, SEQ ID NO: 46, PfMDH) were synthesized from GenScript.

The obtained PCR product and synthesized gene were inserted into the same restriction site of a pSGT208 vector into which a trc promoter without a lac operator was introduced using restriction enzymes KpnI and BamHI, thereby preparing recombinant vectors pS208cT-LpMDH, pS208cT-LmMD1H, pS208cT-RsMDH and pS208cT-PfMDH.

In addition, an enzyme which can help in continuously regenerating NADH used as a coenzyme of the mannitol dehydrogenase was also introduced. As the enzyme that can help in regenerating NADH, a formate dehydrogenase for regenerating NADH by oxidation from formic acid to carbon dioxide was used. *Mycobacterium vaccae* N10-derived formate dehydrogenase (FDH, GenBank: AB072394.1, GI: 15982576, SEQ ID NO: 49) was used, and a gene was synthesized from GenScript. The synthesized gene was inserted into the same restriction site of the previously-constructed pS208cT-LpMDH, pS208cT-LmMDH, pS208cT-RsMDH or pS208cT-PfMDH vector using the restriction enzymes BamHI and XbaI, thereby preparing recombinant vectors pS208cT-LpMDH-FDH, pS208cT-LmMDH-FDH, pS208cT-RsMDH-FDH or pS208cT-PfMDH-FDH, respectively.

The prepared pS208cT-LpMDH-FDH, pS208cT-LmMDH-FDH, pS208cT-RsMDH-FDH or pS208cT-PfMDH-FDH vector was introduced into wild-type *Corynebacterium glutamicum* ATCC 13032 (*Corynebacterium glutamicum* ATCC 13032), and transformation was performed by the method described in Handbook of *Corynebacterium glutamicum* (Lothar Eggeling et al., ISBN 0-8493-1821-1, 2005 by CRC press). The transformed recombinant *Corynebacterium* strain was stored at −80° C. before use.

(2) Experiment for Producing Mannitol Using Recombinant Strain

For mannitol production, a resting cell conversion reaction using a high concentration of bacterial cells was used. To ensure the high concentration of bacterial cells, after the prepared *Corynebacterium glutamicum* recombinant strain was seeded in a 2YT medium containing 20 μg/ml of kanamycin and cultured at 30° C. and 250 rpm for seed culture, a 5 to 10% (v/v) seed culture solution was seeded in a 2YT medium containing 20 μg/ml of kanamycin and 0.5% (v/v) glucose to perform main culture for inducing a sufficient cell mass and protein expression at 30° C. and 180 rpm.

A large quantity of the bacterial cells obtained by the main culture were used in a conversion reaction after the removal of the medium. The resting cell conversion reaction was carried out for 48 hours under the condition of 30° C. and 250 rpm after the bacterial cells were suspended in a 100 mM sodium phosphate (pH 6.5) buffer solution containing 10% (v/v) fructose and 555 mM formic acid to have a concentration of 40 at $OD_{600}$. Concentrations of fructose and mannitol were measured using HPLC. For HPLC, SCL-10A (Shimadzu, Japan) equipped with a Kromasil $5NH_2$ column (4.6 mm×250 mm) was used, and separation was performed by adding 80% acetonitrile as a mobile phase at 1.5 mL/min and 40° C., and analysis was performed using a reflective index (RI) detector. Measurement results are shown in FIG. 9.

Referring to FIG. 9, while there was no significant difference in mannitol production amounts according to the mannitol dehydrogenases, when the *Leuconostoc pseudomesenteroides*-derived mannitol dehydrogenase was used, 48 hours after the conversion reaction, approximately 26 g/L of mannitol was produced from 100 g/L of fructose, resulting in the largest mannitol production amount. Accordingly, for a subsequent mannitol conversion reaction, the *Leuconostoc pseudomesenteroides*-derived mannitol dehydrogenase was continuously used. While not shown in the example, compared to before the formate dehydrogenase was introduced, it was confirmed that the mannitol production amount was increased approximately 86 times, and NADH regeneration was effectively performed using the formate dehydrogenase.

10. Mannitol Production Using Mixed Saccharide of Psicose and Fructose

As described above, psicose and fructose have very similar physical properties. Accordingly, when the mannitol dehydrogenase is any enzyme which does not have a high specificity to a substrate, psicose as well as fructose may also be recognized as substrates and reduced. Therefore, it was examined whether a strategy for converting only fructose of the mixed saccharide of the psicose and the fructose into mannitol and easily isolating the fructose from the psicose can be applied.

Only a substrate was converted into the mixed saccharide of the psicose and the fructose using the constructed recombinant *Corynebacterium* strain, and then the mixed saccharide was used in an experiment in the same manner under the same experimental conditions used in Example 9. The mixed saccharide includes the fructose and the psicose at a ratio of 7:3 (v/v), obtained after the psicose conversion reaction from the fructose, and a concentration of the mixed saccharide was 10% (v/v) as shown in Example 9. Results are shown in FIGS. 10(A) and 10(B).

FIG. 10(A) shows a concentration of remaining psicose, which has not been used as a substrate, and during the conversion reaction for 48 hours, the initial concentration of approximately 30 g/L was maintained without a change, and it was confirmed that the psicose was rarely used. FIG. 10(B) shows an amount of mannitol produced from 70 g/L of fructose constituting 100 g/L of the mixed saccharide, and during the conversion reaction for 48 hours at a conversion temperature of 30° C., approximately 20 g/L of mannitol was produced. Accordingly, it can be confirmed that, in a mixed saccharide substrate solution in which a mannitol dehydrogenase was present with psicose and fructose, only fructose can be selectively used as a substrate. Therefore, it was confirmed that the idea of the present invention in which fructose remaining after the psicose conversion reaction from the fructose is converted into mannitol to easily isolate the psicose can be successfully applied.

11. Comparison of Mannitol Production Using Various Conversion Media

To find the optimal pH condition for enhancing mannitol productivity, mannitol production amounts according to pH were compared. Since it has been known that the mannitol conversion reaction is carried out in a weak acidic condition, a buffer solution which can keep pH in a weak acidic level was selected. In addition, it was also examined whether the mannitol production was efficiently performed when a conversion medium composed of only water without a buffer solution was used.

The mannitol productivity when water (W) without a buffer solution, a sodium acetate buffer solution (SA) with a pH 5, and a PIPES buffer solution (P) with a pH of 6 were used was compared with that when the conventionally used sodium phosphate buffer solution (SP) with a pH of 6.5 was used. Not shown in the example, a convention temperature was 45° C., rather than 30° C. at which the faster conversion reaction was shown, and a conversion medium included 10% (v/v) fructose as a substrate and 555 mM formic acid in water or a buffer solution, as described above, and when a buffer solution was used, a concentration of the buffer solution was 100 mM. Except these, the experiment was carried out under the same conditions as used in Example 9, and with an increased conversion rate, the conversion reaction was carried out only for 24 hours. Results are shown in FIGS. 11(A) and 11(B).

Referring to FIG. 11(A), when PIPES with a pH of 6 was used, approximately 29 g/L of mannitol was produced, and thus the highest mannitol production amount was obtained. In addition, when a conversion medium composed of water was used, there was no difference in mannitol production amount obtained using the conventionally used sodium phosphate buffer solution with a pH of 6.5 as a conversion medium, and therefore it can be confirmed that even with water as a conversion medium, instead of the buffer solution, mannitol can be efficiently produced.

According to the comparison of the mannitol production amounts obtained when different conversion media were used as shown in FIG. 11(A) and pH changes in the conversion reaction of FIG. 11(B), when the pH of the conversion medium was maintained in a range of 6.5 to 7, it seems that mannitol is actively produced. Therefore, it is considered that the optimal pH for the mannitol production under the present conditions was in a range of 6.5 to 7, and this is considered as an eclectic pH between the weakly acidic mannitol production environment with an optimal pH of 5 and the weakly alkaline formate dehydrogenase with an optimal pH of 7.5.

12. Comparison of Mannitol Production Amounts Depending on Open and Closed Reaction Vessels In the previous example, a mannitol conversion reaction was performed in a closed environment using a conical tube. However, to confirm that the reaction was influenced by dissolving $CO_2$ produced in the dehydrogenation of formic acid in the conversion reaction medium without exhaustion, an experiment was performed using a test tube allowing free access of a gas. The experiment was carried out under the same experimental conditions using water as a conversion medium as previously described in Example 11. Experimental results are shown in FIGS. 12(A) and 12(B).

FIG. 12(A) shows mannitol production amounts obtained in a conical tube, which is a closed vessel reaction condition, and a test tube, which is an open vessel reaction condition. It can be confirmed that mannitol production was produced approximately 9 times smaller than that under the open environment using the test tube. However, referring to the result of measuring pH of FIG. 12(B), 24 hours after a mannitol conversion reaction, it can be seen that the pH under an open environment was 9.2, which is much higher than the pH, which was 7.2, under a closed environment. It is assumed that this is because $CO_2$ is not exhausted but dissolved in the medium in the form of carbonic acid under the closed environment to interrupt an increase in pH and the action of a formate dehydrogenase.

The action of a formate dehydrogenase has an effect of increasing a pH of the medium through the consumption of formic acid. However, it is considered that under an open environment, $CO_2$ is well exhausted and the action of a formate dehydrogenase becomes active, and thus the pH is highly increased. Under such a high pH condition, the action of a mannitol dehydrogenase is inhibited, and thus a mannitol production amount is reduced.

Therefore, given that the action of a formate dehydrogenase is a reaction which provides NADH required for the action of a mannitol dehydrogenase, only if the increase in pH at more than a level in which a reaction of the mannitol dehydrogenase is inhibited is prevented under an open environment in which the reaction of a formate dehydrogenase is active, it was assumed that high mannitol productivity can be obtained.

13. Mannitol Production Using Weakly Acidic Conversion Medium in Open Environment As confirmed in the above-described Example 12, when a test tube was used, NADH was sufficiently provided by the active action of a formate dehydrogenase. Therefore, in addition to the open environment, to be suitable for mannitol production, mannitol production was carried out by compensating pH to be weakly acidic. A PIPES (pH 6) buffer solution was added to a conversion medium to have a final concentration of 300 mM, resulting in pH compensation, and a conversion temperature was 45° C. Results are shown in FIG. 13.

Referring to FIG. 13, when a medium composed of only a substrate and water was used without pH compensation, mannitol production was low as 3.6 g/L after 12 hours of the conversion reaction, but when the pH was compensated with a PIPES buffer solution after 24 hours of the conversion reaction, it can be confirmed that 51 g/L, which was the half of 100 g/L fructose, of the substrate was converted into mannitol. It is considered that this is caused by a synergistic effect of improvement in NADH regeneration rate of the formate dehydrogenase in the open environment and improvement in mannitol production rate of the mannitol dehydrogenase due to the pH compensation by the use of the PIPES buffer solution.

14. Improvement in Uptake of Substrate by Introduction of Fructose Transport Protein (1) Development of Recombinant *Corynebacterium* Strain A mannitol production amount was to be improved by increasing an uptake amount of fructose, which is a substrate in cells using a glucose transport protein (GLF) well known to uptake the fructose. The glucose transport protein was *Zymomonas mobilis* (*Zymomonas mobilis* subsp. *mobilis* ZM4 or an ATCC 31821)-derived enzyme, and purchased from KCTC (KCTC 1534). PCR for the glucose transport protein of *Zymomonas mobilis* (GenBank: AAG29864.1; GI: 11095424; SEQ ID NO: 50) was performed using a purified genome as a template and a primer pair of SEQ ID NOs: 51 and 52 as primers. The obtained PCR product was inserted into the same restriction site of pJC1-1-cT-Cmp vector using restriction enzymes BamHI and XbaI, thereby constructing recombinant vector pJC1-1-cT-GLF-Cmp.

The expression vector (pJC1-1-cT-Cmp) used in the construction was prepared by modifying pJC1, which was an *E. coli-Corynebacterium* shuttle vector, and a pJC1-1 vector was constructed by introducing a promoter variable region and an MCS region of a pSGT208 vector and additionally introducing a terminator region of *Corynebacterium*. A pJC1-1-cT vector was constructed by substituting a lac promoter region with a lac operator of the pJC1-1 vector with a trc promoter, and to be used in expression with the pSGT208 vector used in the previous example, a kanamycin-resistant gene was substituted with a chloramphenicol-resistant gene, thereby finally constructing a pJC1-1-cT-Cmp vector.

The previously manufactured pJC1-1-cT-GLF-Cmp recombinant vector was introduced into *Corynebacterium glutamicum* ATCC 13032 transformed with pS208cT-Lp-MDH-FDH, and the recombinant *Corynebacterium* strain was stored at −80° C.

(2) Experiment for Mannitol Production Using Recombinant Strain

An experiment for mannitol production was performed using the previously constructed recombinant *Corynebacterium* strain and a PIPES buffer solution conversion medium under the same conditions used in Example 13, and a chloramphenicol concentration was 5 μg/mL. Results are shown in FIG. 14.

Referring to FIG. 14, when a glucose transport protein was not introduced, 24 hours after the conversion reaction, 51 g/L of mannitol was produced, but when a glucose transport protein was introduced to improve the uptake of fructose, with the 24-hour conversion reaction, 95 g/L of mannitol was produced, and thus almost 100% of a conversion ratio from the fructose was shown.

Accordingly, psicose was able to be easily separated from mannitol by converting fructose that is not easily separated from psicose into mannitol, and a mixed saccharide of psicose and mannitol itself was able to serve as an expensive functional saccharide.

15. Increase in Psicose Content Through Mannitol Crystallization in Mannitol Conversion Reaction Solution (1) Crystallization of Mannitol Through Ethanol Addition Conventionally used fructose and psicose are difficult to be separated and purified since they have similar physical properties. However, since mannitol has a large difference in solubilities between fructose and psicose, separation and purification can be easily performed. In a psicose production process, fructose, which is a substrate, is converted into psicose at a conversion ratio of approximately 30%. Therefore, when 400 g/L of fructose is used, in a reaction solution after the reaction was completed, approximately 280 g/L of fructose is mixed with approximately 120 g/L of psicose.

A mannitol conversion reaction from remaining fructose was performed in the reaction solution using the recombinant *Corynebacterium* strain (pS208cT-MDH-FDH) of Example 13, thereby obtaining a final reaction solution in which fructose (140 g/L), mannitol (140 g/L) and psicose (120 g/L) are mixed. 500 μL of. The mixed saccharide solution of fructose (140 g/L), mannitol (140 g/L) and psicose (120 g/L) was dispensed into an Eppendorf tube and 100 to 900 μL of ethanol was added to separate mannitol which has a low solubility by crystallization.

Following the addition of ethanol, the tube was stayed at room temperature (25° C.) for 1 hour, and centrifuged (13,000 rpm, 10 min) to separate the crystallized mannitol from the solution. A saccharide concentration in the solution obtained through centrifugation was assessed by HPCL under the conditions used in Example 9. Results are shown in FIG. 15.

Referring to FIG. 15, it can be confirmed that the fructose and psicose concentrations in the mannitol conversion reaction solution are maintained during the mannitol crystallization, but only the mannitol concentration is considerably reduced. Therefore, the solution with an increased psicose content may be easily obtained by separating only mannitol through ethanol addition.

(2) Mannitol Crystallization Through Evaporation 100 mL of the mixed saccharide solution (fructose 140 g/L, mannitol 140 g/L, psicose 120 g/L) for the mannitol conversion reaction was added to a beaker, and boiled in water while stirring. Due to evaporation of the mixed saccharide solution, a concentration of the total solution increases, and a volume thereof decreases. Here, when the volume of the solution was gradually reduced to 100 mL, 75 mL and 50 mL due to the evaporation, 1 mL of the solution was cooled at room temperature (25° C.) to crystallize mannitol. After the cooled solution was centrifuged (13,000 rpm, 10 min), the supernatant was subjected to HPLC under the conditions as used in Example 9 to measure saccharide concentrations. Results are shown in FIG. 16.

Referring to FIG. 16, it can be confirmed that the fructose and psicose concentrations in the early mixed saccharide solution were concentrated and increased, but the mannitol concentration was reduced. Therefore, when the fructose is converted into mannitol, the psicose ratio in the mixed saccharide may be increased by a simple method for increasing a temperature.

16. Psicose Separation from Mixed Saccharide Using HPLC

Resolution patterns of mixed saccharides in a reaction solution before and after a mannitol conversion reaction were observed under the HPLC analysis conditions of Example 1. The analyses were performed with a reaction solution for psicose production (psicose 120 g/L, fructose 280 g/L; FIG. 17(A)), a 50% mannitol conversion reaction solution (psicose 120 g/L, fructose 140 g/L, mannitol 140 g/L; FIG. 17(B)), and a 100% mannitol conversion reaction solution (psicose 120 g/L, mannitol 280 g/L; FIG. 17(C)).

Referring to FIG. 17(A), it can be confirmed that the psicose and the fructose have a wide overlapping peak area due to similar retention time. Referring to FIG. 17(B), it is shown that as the fructose is converted 50% into mannitol which has a longer retention time, the overlapping region between the psicose and the fructose is reduced. Referring to FIG. 17(C), when the fructose is all converted into mannitol, it can be confirmed that the HPCL peaks of the psicose and the mannitol are completely separated.

A column used for HPLC in this experiment is a laboratory-level column. Compared to the laboratory-level column, an industrial HPLC column has a larger capacity, can directly separate a high concentration of solution without dilution, but has a lower resolution. Thus, when the industrial HPLC column is used, the overlapping area of the psicose and the fructose will be more obviously shown. Therefore, to efficiently separate psicose from fructose with the industrial HPLC column, it is necessary to convert remaining fructose into mannitol.

---

The invention claimed is:

1. A method for obtaining psicose from a mixture of fructose and psicose, comprising:
   adding a mannitol dehydrogenase to a mixture of fructose and psicose to convert fructose into mannitol; and
   separating the mannitol from the psicose.

2. The method of claim 1, wherein the mannitol dehydrogenase is a mannitol-2-dehydrogenase that is from *Leuconostoc pseudomesenteroides* ATCC 12291 and has the amino acid sequence of SEQ ID NO: 43, a mannitol-2-dehydrogenase that is from *Leuconostoc mesenteroides* and has the amino acid sequence of SEQ ID NO: 44, a mannitol-2-dehydrogenase that is from *Rhodobacter sphaeroides* and has the amino acid sequence of SEQ ID NO: 45, or a mannitol-2-dehydrogenase that is from *Pseudomonas fluorescens* DSM 50106 and that has the amino acid sequence of SEQ ID NO: 46.

3. The method of claim 1, wherein the conversion of the fructose into mannitol is performed in the presence of NADH sources.

4. The method of claim 3, wherein the NADH sources are formic acid and a formate dehydrogenase.

5. The method of claim 1, wherein the conversion of the fructose into mannitol is performed by a microorganism including a gene encoding a mannitol dehydrogenase.

6. The method of claim 5, wherein the microorganism is a microorganism of the genus Corynebacterium.

7. The method of claim 5, wherein the conversion of the fructose into mannitol is performed in a medium containing formic acid, and the microorganism further includes a gene encoding a formate dehydrogenase.

8. The method of claim 7, wherein the formate dehydrogenase is from *Mycobacterium vaccae* N10 and has the amino acid sequence of SEQ ID NO: 49.

9. The method of claim 7, wherein the conversion of the fructose into mannitol is performed in a medium containing a buffer solution in an open reaction system.

10. The method of claim 5, wherein the microorganism further includes a gene encoding a glucose transport protein.

11. The method of claim 10, wherein the glucose transport protein is from *Zymomonas mobilis* and has the sequence of SEQ ID NO: 50.

12. The method of claim 1, wherein the separation of the mannitol is performed by mannitol crystallization according to a difference in solubility between the mannitol and the psicose in a solvent.

13. The method of claim 1, further comprising:
preparing the mixture of fructose and psicose by a reaction between the fructose as a substrate and an epimerase thereof.

14. The method of claim 13, wherein the preparation of the mixture of fructose and psicose is performed in a microorganism at 40 to 90° C.

15. The method of claim 1, wherein the separation of mannitol is performed by liquid chromatography.

16. A method for preparing psicose, comprising:
converting fructose into psicose;
adding a mannitol dehydrogenase to convert unreacted fructose into mannitol.

17. The method of claim 16, further comprising:
separating psicose from the mannitol.

* * * * *